(12) United States Patent
Fischer et al.

(10) Patent No.: US 11,311,473 B2
(45) Date of Patent: *Apr. 26, 2022

(54) USE OF A BIO-BASED POLYMER IN A COSMETIC, DERMATOLOGICAL OR PHARMACEUTICAL COMPOSITION

(71) Applicant: Clariant International Ltd., Muttenz (CH)

(72) Inventors: Dirk Fischer, Hahnheim (DE); Christoph Kayser, Mainz (DE); Gundula Starkulla, Mainz (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/468,659

(22) PCT Filed: Dec. 4, 2017

(86) PCT No.: PCT/EP2017/081417
§ 371 (c)(1),
(2) Date: Jun. 11, 2019

(87) PCT Pub. No.: WO2018/108611
PCT Pub. Date: Jun. 21, 2018

(65) Prior Publication Data
US 2020/0078287 A1 Mar. 12, 2020

(30) Foreign Application Priority Data
Dec. 12, 2016 (EP) .................... 16203549

(51) Int. Cl.
| | |
|---|---|
| A61Q 5/00 | (2006.01) |
| A61Q 19/00 | (2006.01) |
| A61K 8/81 | (2006.01) |
| A61K 8/04 | (2006.01) |
| A61K 8/06 | (2006.01) |
| A61K 47/32 | (2006.01) |

(52) U.S. Cl.
CPC ............ *A61K 8/8158* (2013.01); *A61K 8/042* (2013.01); *A61K 8/062* (2013.01); *A61K 47/32* (2013.01); *A61Q 5/00* (2013.01); *A61Q 19/00* (2013.01); *A61K 2800/10* (2013.01); *A61K 2800/48* (2013.01)

(58) Field of Classification Search
None
See application file for complete search history.

(56) References Cited
U.S. PATENT DOCUMENTS

| | | |
|---|---|---|
| 2,614,989 A | 10/1952 | Hunter |
| 2,809,971 A | 10/1957 | Bernstein |
| 2,865,876 A | 12/1958 | Scott, Jr. |
| 2,904,580 A | 9/1959 | Idol, Jr. |
| 2,905,565 A | 9/1959 | Dietz |
| 3,052,628 A | 9/1962 | Stanberry, Jr. |
| 3,236,733 A | 2/1966 | Karsten |
| 3,509,113 A | 4/1970 | Monagle |
| 3,544,597 A | 12/1970 | Killam |
| 3,753,196 A | 8/1973 | Kurtz |
| 3,761,418 A | 9/1973 | Parran |
| 3,937,721 A | 2/1976 | Schroeck |
| 3,960,918 A | 6/1976 | Schroeck |
| 4,015,991 A | 4/1977 | Persinski |
| 4,138,430 A | 2/1979 | Stiles |
| 4,323,683 A | 4/1982 | Bolich, Jr. |
| 4,342,653 A | 8/1982 | Halverson |
| 4,345,080 A | 8/1982 | Bolich, Jr. |
| 4,379,753 A | 4/1983 | Bolich, Jr. |
| 4,470,982 A | 9/1984 | Winkler |
| 4,487,864 A | 12/1984 | Bermudez |

(Continued)

FOREIGN PATENT DOCUMENTS

| | | |
|---|---|---|
| CN | 101066940 A | 11/2007 |
| CN | 101636381 A | 1/2010 |

(Continued)

OTHER PUBLICATIONS

Adhikary et al, Synthesis, characterization, and application of amylopectin-graft-poly(AM-co-AMPS), Journal of Applied Polymer Science (2012), 126(S1), 6 pages.
Anonymous, "Bio-based material-Wkipedia, the free encyclopedia", (Mar. 12, 2015), URL: https://en.wikipedia.org/wiki/Bio-based_material, (Sep. 1, 2016), XP055299147.

(Continued)

*Primary Examiner* — Jyothsna A Venkat
(74) *Attorney, Agent, or Firm* — Tod A. Waldrop

(57) ABSTRACT

The present invention relates to the use of a polymer in a cosmetic, dermatological or pharmaceutical composition, wherein the polymer is crosslinked or non-crosslinked, characterized in that the polymer comprises at least 9.49 mol-% of repeating units (a) according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B

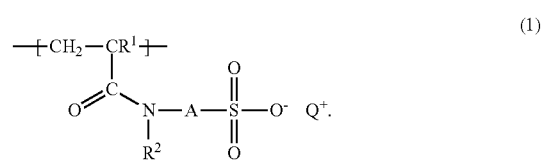

(1)

8 Claims, 3 Drawing Sheets

(56) References Cited

U.S. PATENT DOCUMENTS

| | | | |
|---|---|---|---|
| 4,555,269 A | 11/1985 | Rao | |
| 4,655,943 A | 4/1987 | Elmquist | |
| 4,669,920 A | 6/1987 | Dymond | |
| 4,703,801 A | 11/1987 | Fry | |
| 4,722,958 A | 2/1988 | Sauer | |
| 4,800,071 A | 1/1989 | Kaesler | |
| 4,931,489 A | 6/1990 | Kucera | |
| 5,025,040 A | 6/1991 | Crema | |
| 5,104,646 A | 4/1992 | Bolich, Jr. | |
| 5,194,639 A | 3/1993 | Connor | |
| 5,331,021 A | 7/1994 | Ahmed | |
| 5,472,051 A | 12/1995 | Brothers | |
| 5,510,049 A | 4/1996 | Connor | |
| 5,792,828 A | 8/1998 | Quinn | |
| 6,277,900 B1 | 8/2001 | Oswald | |
| 6,297,337 B1 | 10/2001 | Marchant | |
| 6,437,068 B2 | 8/2002 | Loffler | |
| 6,683,144 B2 | 1/2004 | Loeffler | |
| 6,891,009 B2 | 5/2005 | Loeffler | |
| 7,208,556 B2 | 4/2007 | Loeffler | |
| 8,420,214 B2 | 4/2013 | Kavanagh | |
| 8,629,224 B2 | 1/2014 | Loeffler | |
| 9,399,692 B1 | 7/2016 | Jiang | |
| 9,434,793 B1 | 9/2016 | Kane | |
| 9,611,419 B1 | 4/2017 | Ferrell, Jr. | |
| 11,142,494 B2 * | 10/2021 | Kayser | C07C 309/15 |
| 2003/0064044 A1 | 4/2003 | Chen | |
| 2004/0228809 A1 | 11/2004 | Birkel | |
| 2005/0003984 A1 | 1/2005 | Himmrich | |
| 2006/0019835 A1 | 1/2006 | Kayser | |
| 2007/0100102 A1 | 5/2007 | Fenchl | |
| 2008/0226577 A1 | 9/2008 | L Alloret | |
| 2010/0048850 A1 | 2/2010 | Dubois | |
| 2010/0274048 A1 | 10/2010 | Wakayama | |
| 2010/0278763 A1 | 11/2010 | Loeffler | |
| 2010/0311904 A1 | 12/2010 | Chambers | |
| 2010/0331904 A1 | 12/2010 | Warren | |
| 2011/0110878 A1 | 5/2011 | Knappe | |
| 2011/0136718 A1 | 6/2011 | Rodrigues | |
| 2011/0318515 A1 | 12/2011 | Dubois | |
| 2012/0039819 A1 | 2/2012 | Nakatani | |
| 2012/0100084 A1 | 4/2012 | Peter | |
| 2012/0138299 A1 | 6/2012 | Joseph | |
| 2013/0043384 A1 | 2/2013 | Matsumoto | |
| 2013/0129652 A1 | 5/2013 | Blin | |
| 2014/0051819 A1 | 2/2014 | Davidson | |
| 2014/0086854 A1 | 3/2014 | Klug | |
| 2014/0127147 A1 | 5/2014 | Klug | |
| 2014/0128513 A1 | 5/2014 | Carlson | |
| 2014/0154758 A1 | 6/2014 | Dubois | |
| 2014/0256880 A1 | 9/2014 | Rodrigues | |
| 2015/0239803 A1 | 8/2015 | Sun | |
| 2015/0329877 A1 | 11/2015 | Bockrath | |
| 2016/0177002 A1 | 6/2016 | Palchik | |
| 2016/0185948 A1 | 6/2016 | Kaneumi | |
| 2016/0190641 A1 | 6/2016 | Lee | |
| 2016/0194416 A1 | 7/2016 | Fukuhara | |
| 2016/0194423 A1 | 7/2016 | Michitaka | |
| 2016/0200670 A1 | 7/2016 | Reb | |
| 2016/0200952 A1 | 7/2016 | Takahara | |
| 2016/0211521 A1 | 7/2016 | Iwayasu | |
| 2016/0214896 A1 | 7/2016 | Cadix | |
| 2016/0222580 A1 | 8/2016 | Shimada | |
| 2016/0236982 A1 | 8/2016 | Menceloglu | |
| 2016/0244594 A1 | 8/2016 | Langlotz | |
| 2016/0244629 A1 | 8/2016 | Xu | |
| 2016/0271988 A1 | 9/2016 | Oharuda | |
| 2016/0272676 A1 | 9/2016 | Kozlov | |
| 2016/0288045 A1 | 10/2016 | Kramer | |
| 2016/0298110 A1 | 10/2016 | Mcgall | |
| 2016/0333199 A1 | 11/2016 | Akkerman | |
| 2016/0333215 A1 | 11/2016 | Kawai | |
| 2016/0340456 A1 | 11/2016 | Mori | |
| 2016/0340540 A1 | 11/2016 | Brust | |
| 2016/0340541 A1 | 11/2016 | Lele | |
| 2016/0340617 A1 | 11/2016 | Orizet | |
| 2016/0346188 A1 | 12/2016 | Singh | |
| 2016/0346395 A1 | 12/2016 | Reineke | |
| 2016/0354771 A1 | 12/2016 | Inomata | |
| 2016/0355624 A1 | 12/2016 | Chen | |
| 2016/0355735 A1 | 12/2016 | Motooka | |
| 2016/0355736 A1 | 12/2016 | Motooka | |
| 2016/0359156 A1 | 12/2016 | Ohkubo | |
| 2016/0367468 A1 | 12/2016 | Graham | |
| 2016/0369025 A1 | 12/2016 | Yukawa | |
| 2017/0001188 A1 | 1/2017 | Choi | |
| 2017/0001382 A1 | 1/2017 | Stepper | |
| 2017/0002152 A1 | 1/2017 | Fonnum | |
| 2017/0009111 A1 | 1/2017 | Bauer | |
| 2017/0015693 A1 | 1/2017 | Carlson | |
| 2017/0022451 A1 | 1/2017 | Tamareselvy | |
| 2017/0029305 A1 | 2/2017 | Gill | |
| 2017/0029548 A1 | 2/2017 | Kawai | |
| 2017/0030015 A1 | 2/2017 | Amin | |
| 2017/0031243 A1 | 2/2017 | Hatakeyama | |
| 2017/0037170 A1 | 2/2017 | Gonzalez | |
| 2017/0037206 A1 | 2/2017 | Antheunis | |
| 2017/0037286 A1 | 2/2017 | Lee | |
| 2017/0038500 A1 | 2/2017 | Benz | |
| 2017/0044287 A1 | 2/2017 | Yahagi | |
| 2017/0045819 A1 | 2/2017 | Karasawa | |
| 2017/0059990 A1 | 3/2017 | Tsuchimura | |
| 2017/0073446 A1 | 3/2017 | Corten | |
| 2017/0106013 A1 | 4/2017 | Piergallini | |
| 2017/0121567 A1 | 5/2017 | Kawasaki | |
| 2017/0123106 A1 | 5/2017 | Chien | |
| 2017/0123229 A1 | 5/2017 | Chien | |
| 2017/0129812 A1 | 5/2017 | Langlotz | |
| 2017/0130076 A1 | 5/2017 | Most | |
| 2017/0135941 A1 | 5/2017 | Green | |
| 2017/0145244 A1 | 5/2017 | Yang | |
| 2017/0158951 A1 | 6/2017 | Liang | |
| 2017/0166776 A1 | 6/2017 | Derocher | |
| 2017/0174901 A1 | 6/2017 | Okumura | |
| 2017/0174905 A1 | 6/2017 | Bohling | |
| 2017/0175335 A1 | 6/2017 | Daniels | |
| 2017/0198189 A1 | 7/2017 | Panamarathupalayam | |
| 2017/0210864 A1 | 7/2017 | Zhao | |
| 2017/0210937 A1 | 7/2017 | Okazaki | |
| 2017/0214047 A1 | 7/2017 | Naito | |
| 2017/0225404 A1 | 8/2017 | Naruse | |
| 2017/0226050 A1 | 8/2017 | Voronov | |
| 2017/0240799 A1 | 8/2017 | Wei | |
| 2017/0242174 A1 | 8/2017 | Ito | |
| 2017/0244095 A1 | 8/2017 | Sonobe | |
| 2017/0247487 A1 | 8/2017 | Hemmi | |
| 2017/0247489 A1 | 8/2017 | Tekobo | |
| 2017/0253683 A1 | 9/2017 | Fujiwara | |
| 2017/0275408 A1 | 9/2017 | Yang | |
| 2017/0275447 A1 | 9/2017 | Junk | |
| 2017/0275813 A1 | 9/2017 | Isobe | |
| 2017/0283537 A1 | 10/2017 | Hatton | |
| 2017/0291971 A1 | 10/2017 | Serrano | |
| 2017/0298155 A1 | 10/2017 | Takafuji | |
| 2017/0299779 A1 | 10/2017 | Mita | |
| 2017/0305855 A1 | 10/2017 | Klun | |
| 2017/0306060 A1 | 10/2017 | Fujita | |
| 2017/0306195 A1 | 10/2017 | Lachapell | |
| 2017/0313801 A1 | 11/2017 | Takeo | |
| 2017/0320985 A1 | 11/2017 | Al-Ghamdi | |
| 2017/0321050 A1 | 11/2017 | Elanany | |
| 2017/0327679 A1 | 11/2017 | Ghosh | |
| 2017/0334778 A1 | 11/2017 | Vilinska | |
| 2017/0342220 A1 | 11/2017 | Iijima | |
| 2017/0348219 A1 | 12/2017 | Uyama | |
| 2017/0349679 A1 | 12/2017 | Yashiki | |
| 2017/0355873 A1 | 12/2017 | Wu | |
| 2017/0361297 A1 | 12/2017 | Yamanaka | |
| 2017/0363956 A1 | 12/2017 | Mizuguchi | |
| 2017/0369697 A1 | 12/2017 | Yahagi | |
| 2017/0369698 A1 | 12/2017 | Suzuki | |
| 2018/0002553 A1 | 1/2018 | Harada | |
| 2018/0002563 A1 | 1/2018 | Taylor | |
| 2018/0008936 A1 | 1/2018 | Martinez | |

(56) References Cited

U.S. PATENT DOCUMENTS

| | | | |
|---|---|---|---|
| 2018/0016739 A1 | 1/2018 | Coppens | |
| 2018/0036689 A1 | 2/2018 | Inoue | |
| 2018/0037753 A1 | 2/2018 | Dombrowski | |
| 2018/0052152 A1 | 2/2018 | Sacha | |
| 2018/0057629 A1 | 3/2018 | Letondor | |
| 2018/0072932 A1 | 3/2018 | Kaneko | |
| 2018/0079158 A1 | 3/2018 | Qiu | |
| 2018/0080119 A1 | 3/2018 | Strand | |
| 2018/0086936 A1 | 3/2018 | Steiner | |
| 2018/0086966 A1 | 3/2018 | Favero | |
| 2018/0093113 A1 | 4/2018 | Schade | |
| 2018/0111900 A1 | 4/2018 | Miller | |
| 2018/0118970 A1 | 5/2018 | Kaur | |
| 2018/0118978 A1 | 5/2018 | Yabu | |
| 2018/0133662 A1 | 5/2018 | Kang | |
| 2018/0133986 A1 | 5/2018 | Harada | |
| 2018/0148578 A1 | 5/2018 | Ohta | |
| 2018/0148635 A1 | 5/2018 | Shen | |
| 2018/0155478 A1 | 6/2018 | Kayser | |
| 2018/0163078 A1 | 6/2018 | Sukhishvili | |
| 2018/0169296 A1 | 6/2018 | Benz | |
| 2018/0171051 A1 | 6/2018 | Junk | |
| 2018/0171203 A1 | 6/2018 | Cadix | |
| 2018/0171207 A1 | 6/2018 | Fischer | |
| 2018/0171208 A1 | 6/2018 | Fischer | |
| 2018/0179412 A1 | 6/2018 | Bitler | |
| 2018/0186993 A1 | 7/2018 | Tanida | |
| 2018/0194882 A1 | 7/2018 | Chambrol | |
| 2018/0194948 A1 | 7/2018 | Fan | |
| 2018/0194969 A1 | 7/2018 | An | |
| 2018/0201713 A1 | 7/2018 | Iwasaki | |
| 2018/0206484 A1 | 7/2018 | Bittner | |
| 2018/0215925 A1 | 8/2018 | Hatanaka | |
| 2018/0217294 A1 | 8/2018 | Hyuugaji | |
| 2018/0229023 A1 | 8/2018 | Hatakeyama | |
| 2018/0229024 A1 | 8/2018 | Hatakeyama | |
| 2018/0230256 A1 | 8/2018 | Yamamuro | |
| 2018/0237561 A1 | 8/2018 | Hatakeyama | |
| 2018/0237567 A1 | 8/2018 | Klee | |
| 2018/0240564 A1 | 8/2018 | Hatakeyama | |
| 2018/0244609 A1 | 8/2018 | Favero | |
| 2018/0244911 A1 | 8/2018 | Iso | |
| 2018/0258297 A1 | 9/2018 | Kitou | |
| 2018/0273743 A1 | 9/2018 | Sumerlin | |
| 2018/0273761 A1 | 9/2018 | Yoshimura | |
| 2018/0273774 A1 | 9/2018 | Brown | |
| 2018/0290377 A1 | 10/2018 | Talken | |
| 2018/0291219 A1 | 10/2018 | Kiyosada | |
| 2018/0312739 A1 | 11/2018 | Panamarathupalayam | |
| 2018/0321589 A1 | 11/2018 | Tsuchimura | |
| 2018/0325789 A1 | 11/2018 | Takemoto | |
| 2018/0327585 A1 | 11/2018 | Adkins | |
| 2018/0340098 A1 | 11/2018 | Tanabe | |
| 2018/0344615 A1 | 12/2018 | Gamez-Garcia | |
| 2018/0346626 A1 | 12/2018 | Ying | |
| 2018/0346634 A1 | 12/2018 | Rodriguez-Emmenegger | |
| 2018/0346804 A1 | 12/2018 | Blazewicz | |
| 2018/0348405 A1 | 12/2018 | Chien | |
| 2018/0351149 A1 | 12/2018 | Akiike | |
| 2018/0353650 A1 | 12/2018 | Bose | |
| 2018/0356561 A1 | 12/2018 | Hyugaji | |
| 2018/0362689 A1 | 12/2018 | Jimenez Garcia | |
| 2018/0362833 A1 | 12/2018 | Jackson | |
| 2019/0058195 A1 | 2/2019 | Hanasaki | |
| 2019/0202737 A1 | 7/2019 | Hesselbarth | |
| 2019/0241509 A1 | 8/2019 | Kayser | |
| 2019/0338060 A1* | 11/2019 | Fischer | C08F 222/1006 |
| 2019/0359735 A1 | 11/2019 | Fischer | |
| 2020/0009041 A1* | 1/2020 | Fischer | C08F 220/58 |
| 2020/0010598 A1 | 1/2020 | Fischer | |
| 2020/0017618 A1 | 1/2020 | Fischer | |
| 2020/0017619 A1 | 1/2020 | Fischer | |
| 2020/0078287 A1 | 3/2020 | Fischer | |
| 2020/0095356 A1* | 3/2020 | Fischer | A61K 8/735 |
| 2020/0270506 A1 | 8/2020 | Fischer | |

FOREIGN PATENT DOCUMENTS

| | | | |
|---|---|---|---|
| CN | 102351744 A | 2/2012 | |
| CN | 102361894 A | 2/2012 | |
| CN | 102952044 A | 3/2013 | |
| CN | 103492437 A | 1/2014 | |
| CN | 103819614 | 5/2014 | |
| CN | 104204080 A | 12/2014 | |
| CN | 104884628 A | 9/2015 | |
| CN | 105694403 A | 6/2016 | |
| DE | 2655891 | 6/1977 | |
| EP | 0116671 | 8/1984 | |
| EP | 0157055 | 10/1985 | |
| EP | 0217608 | 4/1987 | |
| EP | 0244981 | 11/1987 | |
| EP | 0550637 | 7/1993 | |
| EP | 0750899 | 1/1997 | |
| EP | 0816403 | 1/1998 | |
| EP | 1045869 | 10/2000 | |
| EP | 1084696 | 3/2001 | |
| EP | 1351654 A1 | 10/2003 | |
| EP | 2105127 | 9/2009 | |
| EP | 2166060 | 3/2010 | |
| JP | 2008084852 A | 4/2008 | |
| JP | 2009149536 A | 7/2009 | |
| JP | 2010519191 A | 6/2010 | |
| JP | 2011506703 A | 3/2011 | |
| JP | 2012087256 A | 5/2012 | |
| JP | 2012521448 A | 9/2012 | |
| JP | 2014500334 | 1/2014 | |
| JP | 2014055232 A | 3/2014 | |
| JP | 2014511423 A | 5/2014 | |
| WO | 9206154 | 4/1992 | |
| WO | 9507340 | 3/1995 | |
| WO | 9800094 | 1/1998 | |
| WO | 9924549 | 5/1999 | |
| WO | 9926991 | 6/1999 | |
| WO | 9966017 | 12/1999 | |
| WO | 0226925 | 4/2002 | |
| WO | 2009063120 A1 | 5/2009 | |
| WO | 2009072480 A | 6/2009 | |
| WO | 2010092875 A1 | 8/2010 | |
| WO | 2011089709 | 7/2011 | |
| WO | 2012084977 | 6/2012 | |
| WO | 2012084977 A1 | 6/2012 | |
| WO | 2012113671 | 8/2012 | |
| WO | 2013017262 | 2/2013 | |
| WO | 2013113938 A1 | 8/2013 | |
| WO | 2013120636 A1 | 8/2013 | |
| WO | 2013178668 | 12/2013 | |
| WO | 2013178700 | 12/2013 | |
| WO | 2014004616 | 1/2014 | |
| WO | 2014086780 | 6/2014 | |
| WO | 2014088034 | 6/2014 | |
| WO | 2015034948 | 3/2015 | |
| WO | 2016042011 | 3/2016 | |
| WO | WO-2017220512 A1 * | 12/2017 | C07C 309/15 |

OTHER PUBLICATIONS

ASTM International, ASTM D6866-12, Standard Test Methods for Determining the Biobased Content of Solid, Liquid, and Gaseous Samples Using Radiocarbon Analysis (2012) (Year: 2012).

Babu, R. P. et al., "Current progress on bio-based polymers and their future trends", Progress in Biomaterials 2013, 2(8), 1-16. (Year: 2013).

Bernd Tieke, "Makromolekulare Chemie Chapter 3", ISBN 10:3527313796, 2005.

Bernd Tieke, "Makromolekulare Chemie: Eine Einführung", Wiley-VCH, 2. vollständig überarbeitete und erweiterte Auflage (3. Nachdruck 2010) ISBN-13: 978 3-527-31379-2, p. 259-261.

Bianca et al., "Fermentative production of isobutene", Appl Microbiol Biotechnol (2012) 93:1377-1387.

CTFA Cosmetic Ingredient Dictionary, Second Edition, 1977, 3 pages.

CTFA Cosmetic Ingredient Handbook, Second Edition, 1992, 2 pages.

De Jong et al, "Product developments in the bio-based chemicals arena", Biofuels, Bioprod. Bioref. 6:606-624 (2012).

(56) References Cited

OTHER PUBLICATIONS

Dräger-Röhrchen & CMS-Handbuch, 17. Auflage, Mar. 2015, 9 pages.
EP1351654B1—Google English Translation (Year: 2003), 19 pages.
George Odian, "Principles of Polymerization", Third Edition, Wiley-Interscience, New York, in chapter 1-4, p. 19 to 24, ISBN 0-471-61020-8, Aug. 1992.
International Cosmetic Ingredient Dictionary, Fifth Edition, 1993.
International Preliminary Report on Patentability for PCT/EP2017/064977, dated Dec. 25, 2018, 7 pages.
International Search Report for App. No. PCT/EP2017/081415, dated Jan. 16, 2018, 3 pages.
International Search Report for App. No. PCT/EP2017/081417, dated Apr. 4, 2018, 2 pages.
International Search Report for App. No. PCT/EP2017/081667, dated Jan. 23, 2018, 3 pages.
International Search Report for App. No. PCT/EP2017/081681, dated Apr. 11, 2018, 3 pages.
International Search Report for PCT/EP2017/06477, dated Aug. 29, 2017, 2 pages.
International Search Report for PCT/EP2017/081665, dated Jan. 23, 2018, 2 pages.
International Search Report for PCT/EP2017/081666, dated Jan. 23, 2018, 2 pages.
Kourosh Kabiri et al: "Chitosan-modified nanoclay-poly(AMPS) nanocomposite hydrogels with improved gel strength", Polymer International, vol. 58, No. 11, Sep. 10, 2009 (Sep. 10, 2009), pp. 1252-1259, XP055379190.
Le Notre et al, Green Chemistry, Biobased synthesis of acrylonitrile from glutamic acid, 2011, 13, pp. 807-809, (Year: 2011).
M. A. Bañares, M. O. Guerrero-Pérez, "Appl. Catal. B: Environmental", 148-149 (2013) 601-603.
M. O. Guerrero-Pérez, M. A. Bañares, "New Reaction: Conversion of Glycerol into Acrylonitrile", ChemSusChem 1 (2008) 511-513.
M. O. Guerrero-Péreza and M. A. Bañares, "Metrics of acrylonitrile: From biomass vs. petrochemical route", Catalysis Today 239 (2015) 25-30.
Machine Translation of AOI Keigo, et al, Bio-based Polymers Seni Gakkaishi, 2010, vol. 66 No. 4, p. 124-128.
Machine Translation of Netsu Sokutei, 2012, 39(4), p. 143-150.
Masao Kunioka, "Measurement Methods of Biobased Carbon Content for Biomass-Based Chemicals and Plastics", Radioisotopes, 62, 901-925 (2013).
Mithilesh Yadav et al: "Superabsorbent nanocomposite (alginate-g-PAMPS/MMT): Synthesis, characterization and swelling behavior", Carbohydrate Polymers, Applied Science Publishers, Ltd. Barking, GB, vol. 90, No. 1, May 4, 2012 (May 4, 2012), pp. 165-173, XP028432003.
Pourjavadi et al, "Modified Carrageenan. 4. Synthesis and Swelling Behavior of Crosslinked KC-g-AMPS Superabsorbent Hydrogel with Antisalt and pH-Responsiveness Properties", Journal of Applied Polymer Science, vol. 98, 255-263 (2005).
Rana, V. et al, "Carbohydrate Polymers", 83 (2011) 1031-1047.
Renae Canterbery Pepe et al., International Cosmetic Ingredient Dictionary and Handbook, 9th Edition, 2002, vol. 4, Published by The Cosmetic, Toiletry, and Fragrance Association, 3 pages.
Srivastava et al, "Graft copolymerization of 2-Acrylamideo-2-methyl-1-propane sulphonic acid onto xanthan gum by ascorbic/bromate redox pair," PMSE Preprints (2004), 90, pp. 291-292.
Srivastava et al, Modification of natural polymer via free radical graft copolymerization of 2 acrylamideo-2-methyl-1-propane sulfonic acid in aqueous media and study of swelling and metal ion sorption behaviour, Journal of Applied Polymer Science (2009), 114(3), 1426-1434.
Le Notre et al., "Supporting Information, Biobased synthesis of acrylonitrile from glutamic acid", Green Chemistry, 2011,13(4), pp. 807-809.
Tateo, F. et al. "Determination of gamma-butyrolactone (GBL) in foods by SBSE-TD/GC/MS". Journal of Food Composition and Analysis 2003, 16, 721-727. (Year: 2003).
Teodorescu, M. et al. "Poly(vinylpyrrolidone)—A Versatile Polymer for Biomedical and Beyond Medical Applications". Polymer-Plastics Technology and Engineering 2015, 54(9), pp. 923-943.
Zhang, Q. et al. "Enhancing the Acetylene Yield from Methane by Decoupling Oxidation and Pyrolysis Reactions: A Comparison with the Partial Oxidation Process". Industrial & Engineering Chemistry Research 2016, 55, 8383-8394 (Year: 2016).

\* cited by examiner

USE OF A BIO-BASED POLYMER IN A COSMETIC, DERMATOLOGICAL OR PHARMACEUTICAL COMPOSITION

FIELD OF THE INVENTION

The present invention relates to the use of a polymer in a cosmetic, dermatological or pharmaceutical composition, wherein the polymer is crosslinked or non-crosslinked, characterized in that the polymer comprises at least 9.49 mol-% of repeating units (a) according to Formula (1), wherein at least 10 wt.-%, preferably at least 20 wt.-% of the repeating units according to Formula (1) comprise from 28 wt.-% to 100 wt.-% bio-based carbon content.

BACKGROUND OF THE INVENTION

Many materials employed for use as thickeners or rheology modifiers are traditionally derived from crude oil. Environmental, economic and sustainability questions are restricting the use of products derived from this limited resource: synthetic surfactants, for example, have been blamed for environmental incidents, particularly vis-à-vis aquatic problems in rivers and lakes. Therefore, there is a desire to identify more sustainable and biodegradable, yet gentle and effective materials. Indeed, consumers are very interested in "natural" products including products with a high percentage of "natural" compounds and/or compounds that are derived from renewable materials. Consumers perceive compounds derived from natural materials to be gentler and more environmentally friendly. Recent industrial developments in "bio-based" chemicals are summarised, for example, in de Jong et al, "Product developments in the bio-based chemicals arena", Biofuels, Bioprod. Bioref. 6:606-624 (2012).

Recently, classical monomers such as ethylene, acrylic acid or methyl methacrylate have been disclosed as being produced with renewable raw materials. US 2014/0154758 (Arkema) discloses the preparation of methyl methacrylate wherein the method comprises the use of acetone cyanohydrin as a raw material, said acetone cyanohydrin being obtained by condensing cyanohydric acid in acetone, and the methyl methacrylate is prepared using a process involving the addition of methanol. Acetone and methanol can be sourced from renewable feedstock. DE 2655891 (DU PONT) discloses the oxidation from 1-propanol to acrylates. U.S. Pat. No. 4,138,430 (DU PONT) discloses the ammoxidation of 1-propanol to form acrylonitrile.

Different synthetic routes for the synthesis of bio-based acrylonitrile are described by M. Olga Guerrero-Péreza and Miguel A. Bañares in Catalysis Today 239 (2015) 25-30. The process for the direct production of acrylonitrile from glycerol was described recently by M. O. Guerrero-Pérez, M. A. Bañares, ChemSusChem 1 (2008) 511 and by M. A. Bañares, M. O. Guerrero-Pérez, Appl. Catal. B (2013), as well as in US 20100048850A1 (Arkema) and WO 2009063120A1 (CONSEJO SUPERIOR DE INVESTIGACIONES CIENTÍFICAS).

Bio-based propylene can directly been used in the so-called SOHIO process to form acrylonitrile. U.S. Pat. No. 2,904,580 (STANDARD OIL CO) describes the ammoxidation of propylene according to the so-called SOHIO process.

WO 2014086780 (Global Bioenergies) discloses a fermentation method for several olefins including propene and isobutene. Propene can be used as a raw material for the ammoxidation to acrylonitrile. Isobutene is an important raw material for polyisobutene rubbers and other downstream products such as tert.-butanol, iso-octanol, branched alkanes or branched alcohols. WO 2016/042011 (Global Bioenergies) describes an enzymatic method for the production of isobutene from 3-methylcrotonyl-CoA. WO 2014/004616 (Gevo Inc) discloses the synthesis of isobutanol by recombinant yeast microorganisms. The catalytic dehydration leads to isobutene.

WO 2015/034948 (MYRIANT CORP) describes the synthesis of bio-based acrylic acid by dehydration of 1,3-propandiol and subsequent oxidation of the allylic alcohol.

Nevertheless, the availability of more renewable polymers suitable for use as components in cosmetic, dermatological or pharmaceutical composition e.g. as thickening agents, is highly limited. Furthermore, there is a need for components that can be used as thickening agents and rheology modifiers, where such components that are not only more renewable, but also provide excellent performance in cosmetic, dermatological or pharmaceutical composition. There is a need, therefore, for providing polymers that can provide the excellent performance of modern polymers yet from more sustainable sources.

SUMMARY OF THE INVENTION

In a first aspect, the present invention relates to the use of a polymer in a cosmetic, dermatological or pharmaceutical composition, wherein the polymer is crosslinked or non-crosslinked, characterized in that the polymer comprises at least 9.49 mol-% of repeating units (a) according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

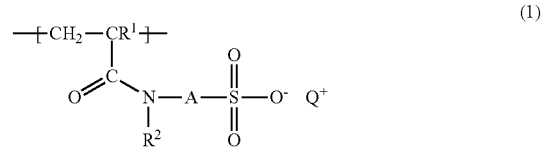

wherein
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof.

Other aspects relate to compositions, methods, uses, and processes related to the polymer disclosed in the first aspect.

DETAILED DESCRIPTION OF THE INVENTION

Definitions and General

Figure 1:
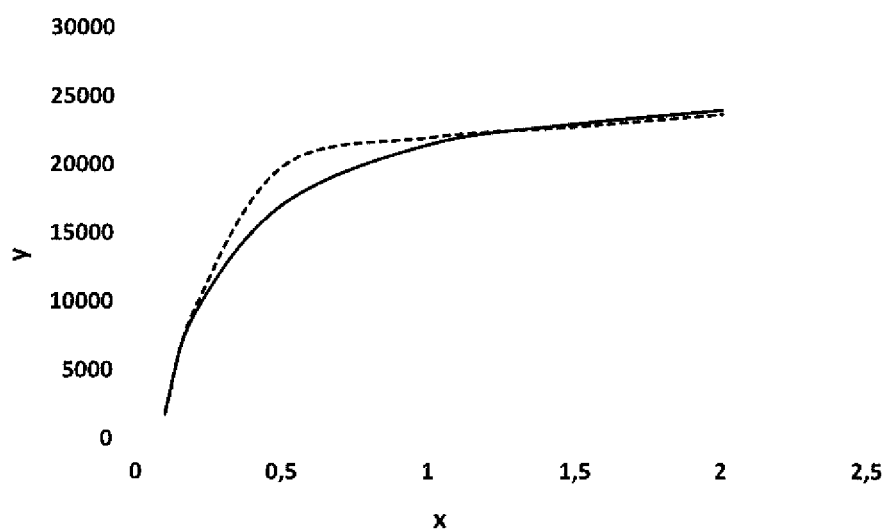
FIG. 1: Viscosity dependence on polymer concentration; measured in deionized water (Brookfield RVDV-1, 20° C., 20 rpm). The x-axis shows the concentration of polymer in wt.-%. The y-axis shows the viscosity in mPa·s. Polymer B1/16 (according to the invention; solid line) and a comparative polymer B1/16 # are compared (broken line).

In this document, including in all embodiments of all aspects of the present invention, the following definitions apply unless specifically stated otherwise. All percentages are by weight (w/w) of the total composition. "wt.-%" means percentage by weight; "vol.-%" means percentage by volume; "mol.-%" means percentage by mole. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The following acronyms are used herein: ACDMT=acryloyldimethyltaurate; AM=acrylamide; AN=acrylonitrile; tBAM=tert.-butyl acrylamide; IBSA=isobutene sulfonic acid; IBDSA=2-methylidene-1,3-propylenedisulfonic acid. Unless otherwise stated, "viscosity" herein is measured at 20° C. viscosity in centipoise (cP) or mPa·s using a Brookfield viscometer model LV, RVT DV-II or LVT DV-II with 10-90% torque at 20 rpm.

"Molecular weight" or "M.Wt." "$M_w$", "$M_w$" or "MW" and grammatical equivalents mean the weight average molecular weight, unless otherwise stated. Also relevant for the determination of the molecular weight distribution is the number average molecular weight "Mn", "$M_n$" and grammatical equivalents, and the polydispersity "D" or "PD".

The weight average molecular weight can be measured by gel permeation chromatography (GPC), also referred to as size exclusion chromatography (SEC). The molecular weight of polymers and its measurement is described in the textbook "Principles of Polymerization" by Georg Odian, third edition, Wiley-Interscience, New York, in chapter 1-4, page 19 to 24, ISBN 0-471-61020-8. The process to determine the weight average molecular weight is described in detail in chapter 3 of Makromolekulare Chemie: Eine Einführung" by Bernd Tieke, Wiley-VCH, 2. vollständig üiberarbeitete und erweiterte Auflage (3. Nachdruck 2010) ISBN-13: 978-3-527-31379-2, page 259-261.

Determination of molecular weight and distribution of ACDMT samples by GPC was determines under the following conditions.

Column: PSS Suprema 30,000 Å 10 µm, 300 mm×8 mm
Detector: RID
Oven temperature: 23° C.
Flow: 1 ml/min
Injection volume: 20 µl
Eluent: 0.07 mol/l disodium hydrogen phosphate in water
Calibration method: Conventional poly(styrene sulfonate) sodium salt calibration Sample preparation: Weigh approx. 10 mg sample in 10 ml 0.07 mol/l disodium hydrogen phosphate in water and shake for 15 min.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than 1%, or less than 0.8%, or less than 0.5%, or less than 0.3%, or about 0%, by total weight of the composition or formulation.

"Monomer" means a discrete, non-polymerised chemical moiety capable of undergoing polymerisation in the presence of an initiator or any suitable reaction that creates a macromolecule e.g. such as polycondensation, polyaddition, radical, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Fuming sulfuric acid" herein means a solution of sulfur trioxide in sulfuric acid. Fuming sulfuric acid is also known as oleum and is identified by the CAS number 8014-95-7, and can be described by the formula $H_2SO_4.xSO_3$ where x is the molar free sulfur trioxide content.

The "biobased content" is reported in ASTM D6866-12, Method B (see section 3.3.9 of ASTM D6866-12). "Biobased carbon content", "biobased content", "biogenic carbon content", "bio-based content", "biomass-derived carbon" herein refer to the same thing and are all measured in wt.-%. Herein, the term 'bio-based carbon content' is used. ASTM D6866-12, Method B lab results report the percentage of bio-based carbon content relative to total carbon, and not to total mass of the sample or molecular weight. A comment on bio-based carbon content calculation: Presently ASTM D6866-12, Method B (see section 9 of ASTM D6866-12) requires the percent modern carbon value (pMC) reported to be multiplied by a correction factor of 0.95 to account for excess carbon-14 in the atmosphere due to nuclear weapons testing. However, a revision is pending for ASTM D6866-12, Method B to update the correction factor to 0.98 due to ongoing decrease in excess atmospheric $^{14}CO_2$. For the purposes of accuracy, the new correction factor of 0.98 is often reported in the field e.g. by suppliers. Generally, results below ~20% bio-based carbon will not be affected. However, results close to 100% will be ~2-3% bio-based carbon higher using the 0.98 factor vs 0.95. Results between ~20-90% will increase by 0-3%. Hence the term "bio-based carbon content" as used herein is defined by the equation:

Bio-based carbon content=pMC*0.95(%)

A review on measurement methods of bio-based carbon content for biomass-based chemicals and plastics is given by Massao Kunioka in *Radioisotopes*, 62, 901-925 (2013).

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

Explanation of and Benefits Provided by the Invention

Surprisingly, it has now been found that it is possible to synthesise good quality bio-based ACDMT at acceptable yields. This bio-based ACDMT can be used for synthesising a polymer for use in the cosmetic or dermatological composition according to the present invention.

Indeed, when considering genetically engineered microbes for use in creating bio-based ACDMT, currently no such microbes are commercially available. ACDMT itself is not similar to any other products that typical microbes would produce naturally. Furthermore, there are few natural microbial pathways capable of converting sulfonic acid groups. Therefore, the person skilled in the art naturally has a bias in his mind that it would be difficult to produce bio-based ACDMT in view of its more synthetic-type chemical moieties. The person skilled in the art may, however, consider that the reaction of acrylic acid with taurine as bio-based materials could form the corresponding acryl-amido taurate compound, which is a similar structure as compared to ACDMT. However, the reactants would preferentiality react to form a Michael adduct, rather than an acryl-amido taurate compound. Hence, it would be known to the person skilled in the art that synthesising bio-based ACDMT is no trivial matter.

Bianca et al (Appl Microbiol Biotechnol (2012) 93:1377-1387) states that a high level of impurities are produced when bio-based isobutene is synthesised (⅔ carbon dioxide). WO 2014086780A2 on pages 5 and 6 mentions various by-products and impurities that may result from when the bio-based isobutene is synthesised. Indeed, on page 14 of WO 2014086780A2 it states "The fermentation off-gas (i.e. a gas stream originating from the fermenter) typically comprises the hydrocarbon as the desired product and the intermediate together with additional gaseous components. Generally, the total content of the desired product, such as isobutene, and the intermediate, such as acetone, in the fermentation off-gas is in a range of 3 to 30 vol.-%, preferably 3 to 20 vol.-%.". In other words, it is known in the art that a very low yield results when known bio-based isobutene synthesis processes are employed, as well as that a significant level of by-products is produced. Indeed, normally at least 98%, typically at least 99.5% purity of isobutene is used in conventional synthesis techniques. Surprisingly, it is possible to produce bio-based ACDMT despite using bio-based components that are typically impure in view of the microbes that produce the bio-based component creating by-products as a result of their natural enzymatic action. International patent application PCT/EP2017/064977 (claiming priority from European patent application 16175218.3 filed on 20 Jun. 2016) in the name of Clariant International Ltd, the disclosure of which is incorporated herein by reference, discloses the synthesis of bio-based acryloyldimethyltaurate, which can be used as a monomer for the polymer according to the present invention.

Furthermore it has surprisingly been found that polymers containing such novel bio-based components can be synthesised. Such polymers may be, for example, crosslinked copolymers.

The present invention relates inter alia to a cosmetic or dermatological composition comprising polymers comprising at least one unit from bio-based ACDMT or similar compounds. The bio-based ACDMT is characterized in that at least one portion of the carbons thereof is biologically sourced and, more specifically, in that it can contain between 38 wt.-% and 100 wt.-% bio-based carbon content in relation to total carbon weight according to the ASTM D6866-12, Method B standard. The preparation method of ACDMT typically comprises the use of acrylonitrile, isobutene and a mixture of sulfuric acid and fuming sulfuric acid comprising sulfur trioxide. Preferably, at least one of the raw materials, acrylonitrile or isobutene, are of bio-based origin. The bio-based ACDMT is suitable to make polymers comprising a bio-based carbon content stemming from its bio-based ACDMT share. The present invention provides the use of such polymers in a cosmetic, dermatological or pharmaceutical composition and the compositions themselves.

ACDMT (see Formula [3]) consists of seven carbon atoms. Preferably a minimum of three, preferably four and most preferred all seven carbon atoms of the ACDMT molecule can become renewable, bio-based carbon atoms. In this way, a high proportion of bio-based and/or biodegradable (polymer) products made from the bio-based monomer ACDMT are recyclable and part of the natural carbon cycle. If these kinds of products are incinerated or biodegraded, the quantity of carbon dioxide that is emitted corresponds to the quantity fixed by photosynthesis during biomass growth.

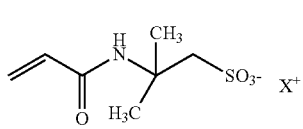

(3)

To date several high performance water soluble or water swellable polymers such as Fluid Loss Additives for the construction and (oil and gas) well construction industry as well as rheology modifiers, comprise ACDMT. Independent from the excellent performance in their applications, such polymers have so-far all been made from petrochemical based, fossil hydrocarbon based ACDMT. The present invention provides new polymers comprising units from bio-based ACDMT or similar compounds (see Formula (1)), thus giving access to the use of such polymers in a cosmetic, dermatological or pharmaceutical composition and the compositions themselves. Such new compositions having the excellent performance benefits that compositions absent of bio-based polymers are already known for.

The details of the invention and its aspects are provided hereinafter.

First Aspect

The first aspect relates to the use of a polymer in a cosmetic, dermatological or pharmaceutical composition, wherein the polymer is crosslinked or non-crosslinked, characterized in that the polymer comprises at least 9.49 mol-% of repeating units (a) according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

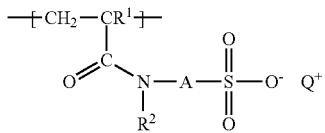

(1)

wherein
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$ or combinations thereof.

For brevity, cosmetic, dermatological or pharmaceutical composition is referred to simply as "composition" herein.

In at least one embodiment, the composition is for treating keratinous material, preferably for treating hair and/or skin. In at least one embodiment, the use of the polymer according to the first aspect is as a thickening agent or rheology modifier in a cosmetic, dermatological or pharmaceutical composition.

In at least one embodiment, the composition comprises a cosmetically acceptable component. Suitable cosmetically acceptable components are mentioned in the second aspect—such cosmetically acceptable components are compatible and combinable with the first aspect. In at least one embodiment, the cosmetically acceptable component is selected from the group consisting of surfactants, auxiliaries, hair conditioning agents, hairstyling polymers, and combinations thereof. Surfactants, auxiliaries, hair conditioning agents and hairstyling polymers are disclosed in the second aspect—such cosmetically acceptable components are compatible and combinable with the first aspect.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

The first aspect relates to the use of a polymer in a composition as defined herein. In at least one embodiment, the composition comprises at least 0.1 wt.-%, or at least 0.2 wt.-%, or at least 0.3 wt.-%, or at least 0.4 wt.-%, or at least 0.5 wt.-%, or at least 0.6 wt.-%, or at least 0.7 wt.-%, or at least 0.8 wt.-%, or at least 0.9 wt.-%, or at least 1.0 wt.-%, or at least 1.1 wt.-%, or at least 1.2 wt.-%, or at least 1.3 wt.-%, or at least 1.4 wt.-%, or at least 1.5 wt.-%, or at least 1.6 wt.-%, or at least 1.5 wt.-%, or at least 1.6 wt.-%, or at least 1.7 wt.-%, or at least 1.8 wt.-%, or at least 1.9 wt.-%, or at least 2.0 wt.-% of the polymer.

In at least one embodiment, the polymer is a crosslinked or non-crosslinked homopolymer. In at least one embodiment, the polymer is a crosslinked or non-crosslinked copolymer. In at least one embodiment, the polymer has a weight average molecular weight of at least 700 g/mol, preferably from 700 g/mol to 10 million g/mol.

In at least one embodiment, the polymer is a derived natural cosmetic ingredient. According to ISO 16128-1:2016 (E) a polymer is a derived natural cosmetic ingredient if it is of greater than 50% natural origin by renewable carbon content. The degree of natural origin can be quantified by renewable carbon content according to analytical procedure ASTM 6866-12, Method B.

Units (a)

In at least one embodiment, the polymer comprises from 9.49 mol-% to 98 mol-%, preferably from 27.5 mol-% to 97.4 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method.

In at least one embodiment, the polymer comprises from 40 to 98 mol-%, preferably from 55 mol-% to 98 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method.

In at least one embodiment, the polymer comprises from 90 mol-% to 99.9 mol-%, preferably from 95 mol-% to 99.5 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method.

In at least one embodiment, the polymer comprises at least 99 mol-%, preferably about 100 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method. In at least one embodiment, the polymer comprises at least 99 mol-%, preferably about 100 mol-% of repeating units (a) according to Formula (1) wherein at least 50 wt.-%, preferably at least 80 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method.

In at least one embodiment, the polymer comprises at least one repeating unit according to Formula (1) wherein $R^1$ and $R^2$ are independently selected from H, methyl or ethyl; A is a linear or branched $C_1$-$C_{12}$-alkyl group; and $Q^+$ is $H^+$, $NH_4^+$, $Li^+$, $Na^+$, $K^+$, ½ $Ca^{++}$, ½ $Mg^{++}$, ½ $Zn^{++}$, ⅓ $Al^{+++}$, or combinations thereof, preferably wherein $Q^+$ is $Na^+$ or $NH_4^+$. $NH_4^+$ is preferred because it is more soluble the favored solvent used in the polymer synthesis. $Na^+$ is preferred because of reduced likelihood of unpreferred gases being produced during synthesis and also due to economic advantages.

In at least one embodiment, $Q^+$ is $NH_4^+$. In at least one embodiment, $Q^+$ is selected from the group monoalkylammonium, dialkylammonium, trialkylammonium and/or tetraalkylammonium salts, in which the alkyl substituents of the amines may independently of one another be ($C_1$ to $C_{22}$)-alkyl radicals or ($C_2$ to $C_{10}$)-hydroxyalkyl radicals.

In at least one embodiment, the polymer comprises at least one repeating unit according to Formula (1). In at least one embodiment, the polymer comprises two or more different repeating units according to Formula (1), such as repeating units according to Formula (1) having different $Q^+$ counterions.

In at least one embodiment, the repeating units according to Formula (1) have a degree of neutralisation of between 0 mol-% and 100 mol-%. In at least one embodiment, the repeating units according to Formula (1) have a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80 mol-%, more preferably more than 90 mol-%, even more preferably more than 95 mol-%. The degree of neutralisation is important in view of the molecular weight of the polymer and the yield of polymer produced.

The repeating units according to Formula (1) comprise from 28 wt.-% to 100 wt.-% bio-based carbon content, relative to the total mass of carbon in the repeating unit according to Formula (1), measured according to standard ASTM D6866-12, Method B. In at least one embodiment, the repeating unit comprises from 35 wt.-%, preferably from 40 wt.-%, more preferably from 54 wt.-%, even more preferably from 57 wt.-% to 100 wt.-%, most preferably about 100 wt.-%, by mass of bio-based carbon content, relative to the total mass of carbon in the repeating unit according to Formula (1), measured according to standard ASTM D6866-12, Method B.

In at least one embodiment, the repeating units according to Formula (1) result from the incorporation of a monomer selected from the group consisting of acryloyldimethyltaurates, acryloyl-1,1-dimethyl-2-methyltaurates (ACDMT), acryloyltaurates, acryloyl-N-methyltaurates, and combinations thereof. Preferably the repeating units according to Formula (1) result from the incorporation of acryloyldimethyltaurate.

In at least one embodiment, the polymer comprises from 55 mol-% to 98 mol-% of repeating units according to Formula (1) wherein at least 30 wt.-%, preferably at least 50 wt.-%, more preferably at least 70 wt.-% of the repeating units comprises from 28 wt.-% to 100 wt.-% bio-based carbon content, relative to the total mass of carbon in the repeating unit according to Formula (1), measured according to standard ASTM D6866-12, Method B.

Preferably the repeating units according to Formula (1) are formed by polymerization of a compound according to Formula (3). More preferably the compound according to Formula (3) is ACDMT.

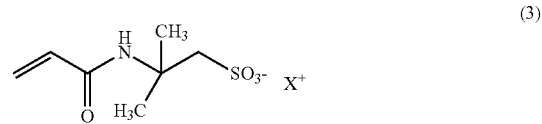

(3)

wherein X is a proton.

In at least one embodiment, the compound according to Formula (3) comprises from 28 wt.-% to 100 wt.-% bio-based carbon content, relative to the total mass of carbon in the compound, measured according to standard ASTM D6866-12, Method B. In at least one embodiment, the compound comprises from 35 wt.-%, preferably from 40 wt.-%, more preferably from 54 wt.-%, even more preferably from 57 wt.-% to 100 wt.-%, most preferably about 100 wt.-%, by mass of bio-based carbon content, relative to the total mass of carbon in the compound, measured according to standard ASTM D6866-12, Method B. Preferably the compound according to Formula (3) is ACDMT.

The bio-based carbon content, relative to the total mass of carbon in the compound or unit, is measured according to standard ASTM D6866-12, Method B. More details on the analytical procedure for determination of bio-based carbon content: the provided sample material does not undergo any pre-treatment procedure and is converted to graphite as is using the following procedure: Depending on the estimated amount of carbon content, typically a few milligrams of sample material is combusted in an elemental analyzer (EA). The resulting gas mixture is cleaned and $CO_2$ is automatically separated by the EA using the purge and trap technology. The remaining $CO_2$ is transferred into a custom-made graphitization system, converted into carbon (graphite) catalytically using $H_2$ and an iron-powder catalyst. The $^{14}C$ determination of the graphite is performed at the Klaus-Tschira-Archaeometrie-Center using an accelerator mass-spectrometer (AMS) of the type MICADAS (developed at the ETH Zurich, Switzerland).

Units (b)

In at least one embodiment, the polymer comprises crosslinking or branching units (b), wherein the crosslinking or branching units result from the incorporation of a monomer comprising at least two olefinically unsaturated double bonds. In at least one embodiment, the polymer comprises from 0.01 mol-% to 5 mol-%, preferably 0.01 mol-% to 4 mol-%, more preferably from 0.01 mol-% to 2 mol-% of crosslinking or branching units.

In at least one embodiment, the crosslinking or branching units comprise least one oxygen, nitrogen, and sulfur or phosphorus atom. In at least one embodiment, the crosslinking or branching units result from monomers having a molecular weight of less than 500 g/mol. In at least one embodiment, the units (b) are bifunctional or trifunctional crosslinking agents.

In at least one embodiment, the polymer comprises two or more different crosslinking or branching units. In at least one embodiment, the crosslinking or branching units result from the incorporation of a monomer according to Formula (2):

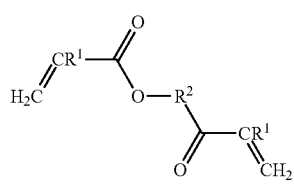

(2)

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms, —$(CH_2—CH_2—O)_n$—
n is a integer from 1 to 100.

A monomer according to Formula (2) has the advantage that the polymer can be predicted as being more brush-like. However, brush-like polymers show different properties, versus linear ones. For example, depending on the different comonomer units the solubility can be in- or decreased.

In at least one embodiment, the crosslinking or branching units result from the incorporation of a monomer according to Formula (4)

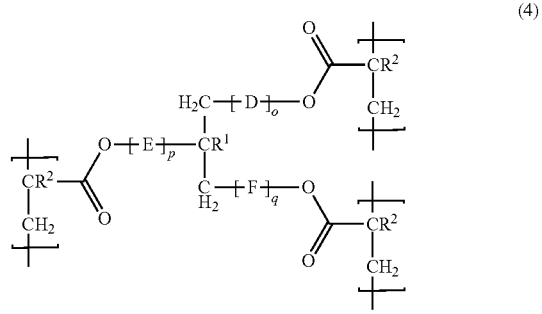

(4)

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms;
D, E, and F are independently methyleneoxy (—$CH_2O$), ethyleneoxy (—$CH_2$—$CH_2$—O—), propyleneoxy (—CH($CH_3$)—$CH_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and
o, p, and q each independently are an integer from 1 to 50.

A monomer according to Formula (4) has the advantage that a polymer can be predicted as being highly branched.

In at least one embodiment, the crosslinking or branching units result from the incorporation of a monomer selected from the group consisting of methylenebisacrylamide; methylenebismethacrylamide; esters of unsaturated monocarboxylic and polycarboxylic acids with polyols, preferably di-acrylates and tri-acrylatees and -methacrylates (e.g. glycerol propoxylate triacrylate [GPTA]), more preferably butanediol and ethylene glycol diacrylate and poly ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. The choice of crosslinking or branching units is important in view of the flexibility of the crosslinks between the main chains of the polymer which affects the final performance of the polymer.

In at least one embodiment, the crosslinking or branching units result from the incorporation of a crosslinker selected from the group consisting of trimethylolpropane triacrylatee (TMPTA) and/or glycerol propoxylate triacrylate (GPTA). Particularly preferred as crosslinkers for the polymers of the invention are glycerol propoxylate triacrylate (GPTA), trimethylolpropane triacrylate (TMPTA), pentaerythritol diacrylate mono stearate (PEAS), hexanediol diacrylate (HDDA), poly ethylene glycol diacrylate (PEG-DA) and hexanediol dimethacrylate (HDDMA). Especially preferred is glycerol propoxylate triacrylatee (GPTA) and trimethylolpropane triacrylatee (TMPTA).

Units (c)

In at least one embodiment, the polymer at least one repeating neutral structural unit (c). In at least one embodiment, the polymer comprises (c) from 0.99 mol-% to 59.99 mol-%, preferably from 1.99 mol-% to 44.99 mol-% of repeating neutral structural units; wherein the repeating neutral units comprises up to 100 wt.-% bio-based carbon content, relative to the total mass of carbon in the repeating unit, measured according to standard ASTM D6866-12, Method B.

In at least one embodiment, the polymer comprises at least one repeating neutral structural unit selected from the group consisting of N-vinylformamide, N-vinylacetamide, N-methyl-N-vinylformamide, N-methyl-N-vinylacetamide, N-vinyl-2-pyrrolidone, N-vinylcaprolactam, vinylacetate, N,N-dimethylacrylamide, N-isopropylacrylamide, acrylamide, methylacrylate, behenylpolyethoxy-(25)-methacrylate, laurylpoly-ethoxy-(7)-methacrylate, cetylpolyethoxy-(10)-methacrylate, stearylpoly-ethoxy-(8)-methacrylate, methoxypoly-ethoxy-(12)-methacrylate, and combinations thereof.

Units (d)

In at least one embodiment, the polymer comprises at least one repeating anionic structural unit. In at least one embodiment, the polymer comprises from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units are different from units (a) and wherein the repeating anionic structural units comprises up to 100 wt.-% bio-based carbon content, relative to the total mass of carbon in the repeating unit, measured according to standard ASTM D6866-12, Method B.

In at least one embodiment, the repeating anionic structural unit results from the incorporation of monomers according to formula (A):

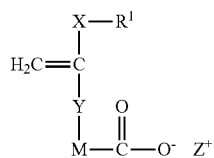

(A)

wherein $R^1$ and $R^3$ are H, methyl or ethyl, or $C(O)O^-Z^+$;

X, Y are selected from a covalent bond, O, $CH_2$, C(O)O, OC(O), $C(O)NR^3$ or $NR^3C(O)$;

M are selected from a covalent bond, $-[C(O)O-CH_2-CH_2]_n-$, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1 to 5; and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or $K^+$.

In at least one embodiment, the polymer comprises at least one repeating anionic structural unit selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, 2-propylacrylic acid or 2-propylacrylate, 2-ethylacrylic acid or 2-ethylacrylate, and their respective alkali or alkaline earth metal salts. In at least one embodiment, the polymer comprises at least one repeating anionic structural unit selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, and their respective alkali or alkaline earth metal salts. These repeating anionic structural units are preferred because they can easily be synthesised from bio-based sources.

Optional Units

In at least one embodiment, the polymer comprises at least one optional unit. In at least one embodiment, the optional unit results from the incorporation of a monomer selected from the group consisting of unsaturated carboxylic acids and their anhydrides and salts, and also their esters with aliphatic, olefinic, cycloaliphatic, arylaliphatic or aromatic alcohols having a carbon number of from 1 to 22. In at least one embodiment, the optional unit results from the incorporation of at least one monomer selected from the group consisting of functionalised (meth)acrylic acid esters, acrylic or methacrylic acid amides, polyglycol acrylic or methacrylic acid esters, polyglycol acrylic or methacrylic acid amides, dipropyleneglycolacrylic or methacrylic acid esters, dipropylenglycolacrylic or methacrylic acid amides, ethoxylated fatty alcohol acrylates or -methacrylates, propoxylated fatty alcohol acrylates or linear or cyclic N-vinylamides or N-methylvinyl amides.

In at least one embodiment, the optional unit results from the incorporation of monomers according to formula (A):

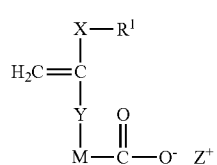

(A)

wherein:

X, Y are selected from a covalent bond, O, $CH_2$, C(O)O, OC(O), $C(O)NR^3$ or $NR^3C(O)$;

$R^1$ and $R^3$ are H, methyl or ethyl, or $C(O)O^-Z^+$;

M is selected from a covalent bond, $-[C(O)O-CH_2-CH_2]_n-$, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1-5, and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or $K^+$.

In at least one embodiment, the optional unit results from the incorporation of a monomer according to formula (A) wherein X is a covalent bond or is $CH_2$. In at least one embodiment, the optional unit results from the incorporation of a monomer according to formula (A) wherein Y is a covalent bond, $CH_2$, C(O)O, or $C(O)NR^3$. In at least one embodiment, the optional unit results from the incorporation of a monomer according to formula (A) wherein M is a covalent bond, —[C(O)O—$CH_2$—$CH_2$]$_n$—, a linear or branched alkylene group with 1 to 6 carbon atoms. In at least one embodiment, the optional unit results from the incorporation of a monomer according to formula (A) wherein $R^1$ is H, methyl or ethyl; X is a covalent bond or is $CH_2$; Y is a covalent bond, $CH_2$, C(O)O, or $C(O)NR^3$; $R^3$ is H, methyl or ethyl; M is a covalent bond, —[C(O)O—$CH_2$—$CH_2$]$_n$—, a linear or branched alkylene group with 1 to 6 carbon atoms; $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, or combinations thereof.

In at least one embodiment, the optional unit results from the incorporation of a monomer selected from the group consisting of N-vinylformamide, N-vinylacetamide, N methyl-N-vinylformamide, N-methyl-N-vinylacetamide, N-vinyl-2-pyrrolidone (NVP), N vinylcaprolactam, vinylacetate, methylvinylether, ethylvinylether, methylallylether, ethylmethallylether, styrol, acetoxystyrol, methylmethallylether, ethylallylether, tert-butylacrylamide, N, N-diethylacrylamide, N,N-dimethylacrylamide, N,N-dimethylmethacrylamide, N,N-dipropylacrylamide, N-isopropylacrylamide, N-propylacrylamide, acrylamide, methacrylamide, methylacrylate, methymethacrylate, tert-butylacrylate, tert-butylmethacrylate, n-butylacrylate, n-butylmethacrylate, laurylacrylate, laurylmethacrylate, behenylacrylate, behenylmethacrylate, cetylacrylate, cetylmethacrylate, stearylacrylate, stearylmethacrylate, tridecylacrylate, tridecylmethacrylate, polyethoxy-(5)-methacrylate, polyethoxy-(5)-acrylate, polyethoxy-(10)-methacrylate, polyethoxy-(10)-acrylate, behenylpolyethoxy-(7)-methacrylate, behenylpolyethoxy-(7)-acrylate, behenylpolyethoxy-(8)-methacrylate, behenylpoly-ethoxy-(8)-acrylate, behenylpolyethoxy-(12)-methacrylate, behenylpoly-ethoxy-(12)-acrylate, behenylpolyethoxy-(16)-methacrylate, behenylpolyethoxy-(16)-acrylate, behenylpolyethoxy-(25)-methacrylate, behenylpolyethoxy-(25)-acrylate, laurylpoly-ethoxy-(7)-methacrylate, laurylpolyethoxy-(7)-acrylate, laurylpolyethoxy-(8)-methacrylate, laurylpolyethoxy-(8)-acrylate, laurylpolyethoxy-(12)-methacrylate, laurylpolyethoxy-(12)-acrylate, laurylpolyethoxy-(16)-methacrylate, laurylpoly-ethoxy-(16)-acrylate, laurylpolyethoxy-(22)-methacrylate, lauryl polyethoxy-(22)-acrylate, laurylpolyethoxy-(23)-methacrylate, laurylpolyethoxy-(23)-acrylate, cetylpolyethoxy-(2)-methacrylate, cetylpolyethoxy-(2)-acrylate, cetylpolyethoxy-(7)-methacrylate, cetylpolyethoxy-(7)-acrylate, cetylpolyethoxy-(10)-methacrylate, cetylpolyethoxy-(10)-acrylate, cetylpolyethoxy-(12)-methacrylate, cetylpolyethoxy-(12)-acrylate cetylpoly-ethoxy-(16)-methacrylate, cetylpolyethoxy-(16)-acrylate cetyl polyethoxy-(20)-methacrylate, cetylpolyethoxy-(20)-acrylate, cetylpolyethoxy-(25)-methacrylate, cetylpolyethoxy-(25)-acrylate, cetylpolyethoxy-(25)-methacrylate, cetylpolyethoxy-(25)-acrylate, stearylpolyethoxy-(7)-methacrylate, stearylpolyethoxy-(7)-acrylate, stearylpoly-ethoxy-(8)-methacrylate, stearyl polyethoxy-(8)-acrylate, stearylpolyethoxy-(12)-methacrylate, stearylpolyethoxy-(12)-acrylate, stearylpolyethoxy-(16)-methacrylate, stearylpolyethoxy-(16)-acrylate, stearylpolyethoxy-(22)-methacrylate, stearyl poly-ethoxy-(22)-acrylate, stearylpolyethoxy-(23)-methacrylate, stearylpolyethoxy-(23)-acrylate, stearylpolyethoxy-(25)-methacrylate, stearylpolyethoxy-(25)-acrylate, tridecyl polyethoxy-(7)-methacrylate, tridecylpolyethoxy-(7)-acrylate, tridecylpolythoxy-(10)-methacrylate, tridecylpolyethoxy-(10)-acrylate, tridecylpolyethoxy-(12)-methacrylate, tridecylpolyethoxy-(12)-acrylate, tridecylpolyethoxy-(16)-methacrylate, tridecylpolyethoxy-(16)-acrylate, tridecylpolyethoxy-(22)-methacrylate, tridecylpoly-ethoxy-(22)-acrylate, tridecylpolyethoxy-(23)-methacrylate, tridecylpolyethoxy-(23)-acrylate, tridecylpoly-ethoxy-(25)-methacrylate, tridecylpolyethoxy-(25)-acrylate, methoxy-polyethoxy-(7)-methacrylate, methoxy-polyethoxy-(7)-acrylate, methoxypoly-ethoxy-(12)-methacrylate, methoxypolyethoxy-(12)-acrylate, methoxypolyethoxy-(16)-methacrylate, methoxypolyethoxy-(16)-acrylate, methoxypolyethoxy-(25)-methacrylate, methoxy-polyethoxy-(25)-acrylate, acrylic acid, ammonium acrylate, sodium acrylate, potassium acrylate, lithium acrylate, zinc acrylate, calcium acrylate, magnesium acrylate, zirconium acrylate, methacrylic acid, ammonium methacrylate, sodium methacrylate, potassium methacrylate, lithium methacrylate, calcium methacrylate, magnesium methacrylate, zirconium methacrylate, zinc methacrylate, 2-carboxyethylacrylate, ammonium 2-carboxyethylacrylate, sodium 2-carboxyethylacrylate, potassium 2-carboxyethylacrylate, lithium 2 carboxyethylacrylate, zinc 2-carboxyethylacrylate, calcium 2-carboxyethylacrylate, magnesium 2-carboxyethylacrylate, zirconium 2-carboxyethylacrylate, 2-carboxyethylacrylate-oligomere, ammonium 2-carboxyethylacrylate-oligomers, sodium 2-carboxyethylacrylate-oligomers, potassium 2-carboxyethylacrylate-oligomers, lithium 2 carboxyethylacrylate-oligomers, zinc 2-carboxyethylacrylate-oligomers, calcium 2-carboxyethylacrylate-oligomers, magnesium 2-carboxyethylacrylate-oligomers, zirconium 2-carboxyethylacrylate-oligomers, itaconic acid, sodium itaconate, potassium itaconate, lithium itaconate, calcium itaconate, magnesium itaconate, zirconium itaconate, zinc itaconate, 2-ethylacryl acid, ammonium 2-ethylacrylate, sodium 2-ethylacrylate, potassium 2-ethylacrylate, lithium 2-ethylacrylate, calcium 2-ethylacrylate, magnesium 2-ethylacrylate, zirconium 2-ethylacrylate, zinc 2-ethylacrylate, 2-propylacryl acid, ammonium 2-propylacrylate, sodium 2-propylacrylate, potassium 2-propylacrylate, lithium 2-propylacrylate, calcium 2-propylacrylate, magnesium 2-propylacrylate, magnesium 2-propylacrylate, zirconium 2-propylacrylate, zinc 2-propylacrylate, glycerin propoxylate triacrylate (GPTA), trimethylolpropane triacrylate (TMPTA), pentaerythritoldiacrylate monostearate (PEAS), polyethyleneglycol diacrylate, hexanediol diacrylate (HDDA), hexanediol dimethacrylate (HDDMA), and combinations thereof.

In a preferred embodiment, the optional unit results from the incorporation of a monomer selected from the group consisting of glycerine propoxylate triacrylate (GPTA) and trimethylolpropantriacrylate (TMPTA).

In a preferred embodiment, the optional unit results from the incorporation of a monomer selected from the group consisting of N-vinylformamide, N-vinylacetamide, N-methyl-N-vinylacetamide, N-vinyl-2-pyrrolidone (NVP), N,N-diethylacrylamide, acrylamide, methacrylamide, methylacrylate, methylmethylacrylate, tert-Butylacrylate, acrylic acid, methacrylic acid, 2-carboxyethylacrylate, 2-carboxyethylacrylate oligomers, itaconic acid glycerine propoxylate triacrylate (GPTA), trimethylolpropane triacrylate (TMPTA), pentaerythritol diacrylate monostearate (PEAS) and polyethyleneglycol diacrylate.

In at least one embodiment, the optional unit results from the incorporation of a monomer selected from the group consisting of acrylic acid, methacrylic acid, styrenesulfonic acid, maleic acid, fumaric acid, crotonic acid, itaconic acid, and senecic acid. In at least one embodiment, the optional unit results from monomers selected from the group consisting of open-chain N-vinyl amides, preferably N-vinylformamide (VIFA), N-vinylmethylformamide, N-vinylmethylacetamide (VIMA) and N-vinylacetamides; cyclic N-vinyl amides (N-vinyl lactams) with a ring size of 3 to 9, preferably N-vinylpyrrolidones (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacryl amide, hydroxypropylmethacrylamide, and mono[2-(methacryloyloxy)ethyl]succinate; N,N-dimethylaminomethacrylate; diethylaminomethylmethacrylate; acrylamideo- and methacrylamideoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; tetrafluoroethylene; and combinations thereof.

Example Embodiments of the First Aspect

In a preferred embodiment, the first aspect relates to the use of a polymer in a cosmetic, dermatological or pharmaceutical composition, wherein the polymer is crosslinked or non-crosslinked, characterized in that the polymer comprises:
a) from 90 mol-% to 99.9 mol-%, preferably from 95 mol-% to 99.5 mol-% of repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

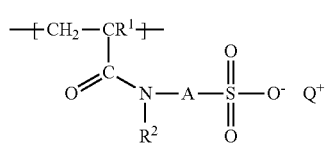
(1)

wherein:
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$ or combinations thereof; and
(b) optionally from 0.01 mol-% to 10 mol-%, preferably from 0.01 mol-% to 5 mol-% of crosslinking or branching units, wherein the crosslinking or branching units result from the incorporation of a monomer comprising at least two olefinically unsaturated double bonds.

In at least one embodiment, the polymer comprises from 96 mol-% to 99.7 mol-%, preferably from 97 mol-% to 99.5 mol-% units (a) and from 0.3 mol-% to 4 mol-%, preferably from 0.5 mol-% to 3 mol-% units (b). In at least one embodiment, the polymer comprises units (a) and (b), such that the sum thereof is at least 99 mol-%, by total weight of the polymer.

In a preferred embodiment, the first aspect relates to the use of a polymer in a cosmetic, dermatological or pharmaceutical composition, wherein the polymer is crosslinked or non-crosslinked, characterized in that the polymer comprises:
a) from 40 mol-% to 98 mol-%, preferably from 55 mol-% to 98 mol-% repeating units according to Formula (1) wherein at least 10 wt.-%, preferably at least 20 wt.-% of the repeating units comprises from 28 wt.-% to 100 wt.-% bio-based carbon content, relative to the total mass of carbon in the repeating unit according to Formula (1), measured according to standard ASTM D6866-12, Method B;

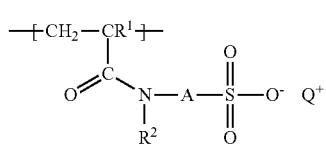
(1)

wherein:
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof;
(b) optionally from 0.01 mol-% to 5 mol-%, preferably from 0.01 mol-% to 3 mol-% crosslinking or branching units, wherein the crosslinking or branching units result from the incorporation of a monomer comprising at least two olefinically unsaturated double bonds; and (c) optionally from 0.99 mol-% to 59.99 mol-%, preferably from 1.99 mol-% to 44.99 mol-% of repeating neutral structural units wherein at least 10 wt.-%, preferably at least 20 wt.-% of the neutral structural units comprises from 0 wt.-% to 100 wt.-% bio-based carbon content, relative to the total mass of carbon in the repeating unit, measured according to standard ASTM D6866-12, Method B.

In at least one embodiment, the polymer comprises from 45 mol-% to 97 mol-%, preferably from 65 mol-% to 96 mol-% units (a), from 0.25 mol-% to 4 mol-%, preferably from 0.3 mol-% to 3 mol-% units (b), from 2 mol-% to 54.7 mol-%%, preferably from 2.5 mol-% to 34.5 mol-% units (c). In at least one embodiment, the polymer comprises units (a), (b) and (c) such that the sum thereof is at least 99 mol-%, by total weight of the polymer.

In at least one embodiment, the polymer comprises from 70 mol-% to 98 mol-%, preferably from 73 mol-% to 96 mol-% units (a), from 0.6 mol-% to 2.5 mol-%, preferably from 0.75 mol-% to 2 mol-% units (b), from 1.4 mol-% to 54.7 mol-%, preferably from 2.5 mol-% to 34.5 mol-% units (c). In at least one embodiment, the polymer comprises units (a), (b) and (c) such that the sum thereof is at least 99 mol-%, by total weight of the polymer.

In a preferred embodiment, the first aspect relates to the use of a polymer in a cosmetic, dermatological or pharmaceutical composition, wherein the polymer is crosslinked or non-crosslinked, characterized in that the polymer comprises:

a) from 9.49 mol-% to 98 mol-%, preferably from 27.5 mol-% to 97.4 mol-% repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

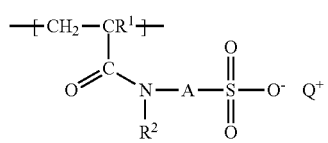

(1)

wherein:

$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions [$NHR^5R^6R^7$] wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or Q is $Li^+$, $Na^+$, $K^+$, ½ $Ca^{++}$, ½ $Mg^{++}$, ½ $Zn^{++}$, ⅓ $Al^{+++}$, or combinations thereof;

(b) optionally from 0.01 mol-% to 5 mol-%, preferably from 0.01 mol-% to 4 mol-% crosslinking or branching units, wherein the crosslinking or branching units result from the incorporation of a monomer comprising at least two olefinically unsaturated double bonds;

(c) optionally from 0.01 mol-% to 88.52 mol-%, preferably from 0.05 mol-% to 72.4 mol-% of repeating neutral structural units, preferably wherein at least 10 wt.-%, preferably at least 20 wt.-% of the repeating neutral structural units comprises from 0 wt.-% to 100 wt.-% bio-based carbon content, relative to the total mass of carbon in the repeating neutral structural unit, measured according to standard ASTM D6866-12, Method B;

(d) optionally from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units are different from units (a) and preferably wherein at least 10 wt.-%, preferably at least 20 wt.-% of the repeating anionic structural units comprise from 0 wt.-% to 100 wt.-% bio-based carbon content, relative to the total mass of carbon in the repeating anionic structural unit, measured according to standard ASTM D6866-12, Method B.

In at least one embodiment, the polymer comprises from 37 mol-% to 96.4 mol-%, preferably from 43 mol-% to 95.3 mol-% units (a), from 0.1 mol-% to 3 mol-%, preferably from 0.2 mol-% to 2 mol-% units (b), from 0.1 mol-% to 59.3 mol-%, preferably from 0.5 mol-% to 52.8 mol-% units (c), and from 3.5 mol-% to 16 mol-%, preferably from 4 mol-% to 14 mol-% units (d). In at least one embodiment, the polymer comprises units (a), (b), (c) and (d) such that the sum thereof is at least 99 mol-%, by total weight of the polymer.

In at least one embodiment, the polymer comprises from 70 mol-% to 94.5 mol-%, units (a), from 0.35 mol-% to 1.5 mol-%, units (b), from 0.65 mol-% to 25.65 mol-% units (c), and from 4.5 mol-% to 12 mol-% units (d). In at least one embodiment, the polymer comprises units (a), (b), (c) and (d) such that the sum thereof is at least 99 mol-%, by total weight of the polymer.

In a preferred embodiment, the first aspect relates to the use of the cosmetic, dermatological or pharmaceutical composition according to the second aspect.

Second Aspect

A second aspect relates to a cosmetic, dermatological or pharmaceutical composition comprising:
(I) a polymer;
(II) a cosmetically acceptable component;
wherein the polymer is crosslinked or non-crosslinked, characterized in that the polymer comprises at least 9.49 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method B;

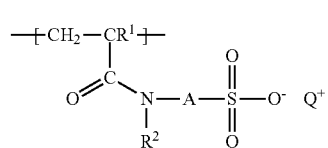

(1)

wherein:
R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof.

In at least one embodiment, the polymer is the polymer according to the first aspect.

The cosmetic, dermatological or pharmaceutical composition—or for brevity herein "composition", comprises a cosmetically acceptable component. In at least one embodiment, the cosmetically acceptable component is selected from the group consisting of surfactants, auxiliaries, hair conditioning agents, hairstyling polymers, and combinations thereof.

Surfactant

In at least one embodiment, the composition comprises a surfactant. In at least one embodiment, the composition comprises a surfactant system comprising a plurality of different surfactants. In at least one embodiment, the surfactant system comprises a surfactant selected from the group consisting of anionic surfactants, cationic surfactants, non-ionic surfactants, zwitterionic surfactants and/or amphoteric surfactants. In at least one embodiment, the surfactant is selected from the group consisting of anionic surfactants, cationic surfactants, non-ionic surfactants, zwitterionic surfactants and/or amphoteric surfactants.

In at least one embodiment, the composition comprises a total amount of surfactant of from 0.01 wt.-% to 70 wt.-%, from 0.1 wt.-% to 40 wt.-%, from 1 wt.-% to 30 wt.-%, from 2 wt.-% to 20 wt.-%.

In at least one embodiment, the composition comprises an anionic surfactant. In at least one embodiment, the composition comprises an anionic surfactant as cosmetically acceptable component (II). In at least one embodiment, the anionic surfactant is selected from the group consisting of (C$_{10}$-C$_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkyl-phenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, acylglutamates, and mixtures thereof. The anionic surfactants (and their mixtures) can be used in the form of their water-soluble or water-dispersible salts, examples being the sodium, potassium, magnesium, ammonium, mono-, di-, and triethanolammonium, and analogous alkylammonium salts. In at least one embodiment, the anionic surfactant is the salt of an anionic surfactant comprising 12 to 14 carbon atoms. In at least one embodiment, the anionic surfactant is selected from the group consisting of sodium lauryl sulfate, sodium laureth sulfate, sodium tridecyl sulfate, sodium trideceth sulfate, sodium myristyl sulfate, sodium myreth sulfate, and mixtures thereof. Typical anionic surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecyl benzene sulphonate, triethanolamine dodecylbenzene sulphonate, sodium cocoyl isethionate, sodium lauryl isethionate, lauryl ether carboxylic acid and sodium N-lauryl sarcosinate. Preferred anionic surfactants are selected from sodium lauryl sulphate and sodium lauryl ether sulphate(n) EO, (where n is from 1 to 3); more preferably sodium lauryl ether sulphate(n)EO, (where n is from 1 to 3); most preferably sodium lauryl ether sulphate(n)EO where n=1. Preferably the level of alkyl ether sulphate is from 0.5 wt.-% to 25 wt.-% of the total composition, more preferably from 3 wt.-% to 18 wt.-%, most preferably from 6 wt.-% to 15 wt.-% of the total composition.

The total amount of anionic surfactant in the composition may range from 0.5 wt.-% to 45 wt.-%, more preferably from 1.5 wt.-% to 20 wt.-%.

In at least one embodiment, the composition comprises a fatty acyl isethionate. In at least one embodiment, the composition comprises fatty acyl isethionate at a level of from 1 to 10 wt.-%, more preferably from 2 to 8 wt.-%, most preferably from 2.5 to 7.5 wt.-%. A preferred fatty acyl isethionate product comprises fatty acyl isethionate surfactant at a level of from 40 to 80 wt.-% of the product, as well as free fatty acid and/or fatty acid salt at a level of from 15 to 50 wt.-%. Preferably, greater than 20 wt.-% and less than 45 wt.-%, more preferably greater than 25 wt.-% and less than 45 wt.-% of the fatty acyl isethionate are of chain length greater than or equal to C6; and greater than 50 wt.-%, preferably greater than 60 wt.-% of the free fatty acid/soap is of chain length C6 to C20. In addition, the composition may contain isethionates salts which are present typically at levels less than 5 wt.-%, and traces (less than 2 wt.-%) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) preferably should have more than 20 wt.-%, preferably more than 25 wt.-%, but no more than 45 wt.-%, preferably 35 wt.-% (on basis of fatty acyl isethionates reaction product) of fatty acyl group with 16 or greater carbon atoms to provide both excellent lather and mildness of the resulting fatty acyl isethionate product. These longer chain fatty acyl isethionate surfactants and fatty acids, i.e. fatty acyl group and fatty acid with 16 or more carbons, can typically form insoluble surfactant/fatty acid crystals in water at ambient temperatures.

In at least one embodiment, the composition comprises an acylglycinate surfactant. In at least one embodiment, the acylglycinate surfactant conforms to the formula (Y):

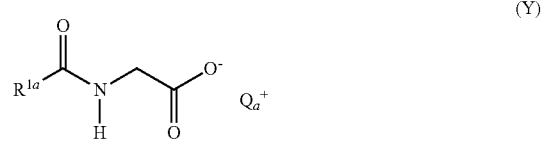

(Y)

wherein
R$^{1a}$ is a linear or branched, saturated alkanoyl group having 6 to 30, preferably 8 to 22, particularly preferably 8 to 18, carbon atoms or is a linear or branched, mono- or polyunsaturated alkenoyl group having 6 to 30, preferably 8 to 22 and particularly preferably 12 to 18 carbon atoms, and $Qa^+$ is a cation. In at least one embodiment, $Qa^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof. Optionally $R^{1a}$ is independently from one another, are $(C_1$-$C_{22})$-alkyl radicals or $(C_2$-$C_{10})$-hydroxyalkyl radicals. In at least one embodiment, the acylglycinate surfactant is selected from sodium cocoylglycinate and potassium cocoylglycinate.

In at least one embodiment, the composition comprises a glutamate surfactant corresponding to formula (Z) or a salt thereof:

wherein
R' is $HOOC$—$CH_2$—$CH_2$— or $M^+$-$OOC$—$CH_2$—$CH_2$— wherein $M^+$ is a cation; and wherein R is a linear or branched, saturated alkanoyl group having 6 to 30, preferably 8 to 22, more preferably 8 to 18, carbon atoms or is a linear or branched, mono- or polyunsaturated alkenoyl group having 6 to 30, preferably 8 to 22 and more preferably 12 to 18 carbon atoms. In at least one embodiment, $M^+$ is a metal cation. In at least one embodiment, $M^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof. In at least one embodiment, the glutamate surfactant is selected from sodium cocoyl glutamate and potassium cocoyl glutamate.

In at least one embodiment, the composition comprises a non-ionic surfactant. The non-ionic surfactants may be present in the range 0 to 5 wt.-%. The non-ionic surfactants that can be included in the compositions herein include condensation products of aliphatic primary or secondary linear or branched chain alcohols or phenols with alkylene oxides, usually ethylene oxide and generally having from 6 to 30 ethylene oxide groups. Alkyl ethoxylates are particularly preferred. Most preferred are alky ethoxylates having the formula R—$(OCH_2CH_2)_n$OH, where R is an alkyl chain of C12 to C15, and n is 5 to 9. Other suitable nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APGs). Typically, APG is one which comprises an alkyl group connected (optionally via a bridging group) to a block of one or more glycosyl groups.

In at least one embodiment, the non-ionic surfactant has an HLB (Hydrophilic Lipophilic Balance) of greater than 12. Optionally, the non-ionic surfactant is selected from the group consisting of ethoxylated or ethoxylated/propoxylated fatty alcohols with a fatty chain comprising from 12 to 22 carbon atoms, ethoxylated sterols, such as stearyl- or lauryl alcohol (EO-7), PEG-16 soya sterol or PEG-10 soya sterol, polyoxyethylene polyoxypropylene block polymers (poloxamers), and mixtures thereof.

In at least one embodiment, the non-ionic surfactant is selected from the group consisting of ethoxylated fatty alcohols, fatty acids, fatty acid glycerides or alkylphenols, in particular addition products of from 2 to 30 mol of ethylene oxide and/or 1 to 5 mol of propylene oxide onto C8- to C22-fatty alcohols, onto C12- to C22-fatty acids or onto alkyl phenols having 8 to 15 carbon atoms in the alkyl group, C12- to C22-fatty acid mono- and diesters of addition products of from 1 to 30 mol of ethylene oxide onto glycerol, addition products of from 5 to 60 mol of ethylene oxide onto castor oil or onto hydrogenated castor oil, fatty acid sugar esters, in particular esters of sucrose and one or two C8- to C22-fatty acids, INCI: Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate, esters of sorbitan and one, two or three C8- to C22-fatty acids and a degree of ethoxylation of from 4 to 20, polyglyceryl fatty acid esters, in particular of one, two or more C8- to C22-fatty acids and polyglycerol having preferably 2 to 20 glyceryl units, alkyl glucosides, alkyl oligoglucosides and alkyl polyglucosides having C8 to C22-alkyl groups, e.g. decylglucoside or laurylglucoside, and mixtures thereof.

In at least one embodiment, the non-ionic surfactant is selected from the group consisting of fatty alcohol ethoxylates (alkylpolyethylene glycols), alkylphenol polyethylene glycols, alkylmercaptan polyethylene glycols, fatty amine ethoxylates (alkylaminopolyethylene glycols), fatty acid ethoxylates (acylpolyethylene glycols), polypropylene glycol ethoxylates (Pluronics®), fatty acid alkylol amides, (fatty acid amide polyethylene glycols), N-alkyl-, N-alkoxy-polyhydroxy-fatty acid amide, sucrose esters, sorbitol esters, polyglycol ethers, and mixtures thereof.

In at least one embodiment, the composition comprises a fatty N-methyl-N-glucamide surfactant. In at least one embodiment, the fatty N-methyl-N-glucamide surfactant conforms to the formula (X):

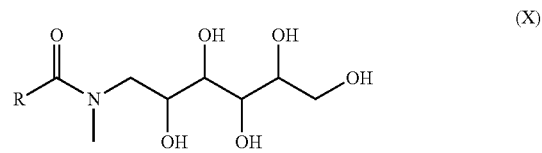

wherein
R is a linear or branched alkyl or alkenyl group having from 3 to 30 carbon atoms. In at least one embodiment, R is an alkyl group having from 3 to 30 carbon atoms. In at least one embodiment, R is a saturated aliphatic hydrocarbon group which can be linear or branched and can have from 3 to 20 carbon atoms in the hydrocarbon chain, preferably linear or branched. Branched means that a lower alkyl group such as methyl, ethyl or propyl is present as substituent on a linear alkyl chain. Suitable fatty N-methyl-N-glucamide surfactants are described in WO2013/178700 and EP0550637, which are incorporated herein by reference. In at least one embodiment, the fatty N-methyl-N-glucamide surfactant is selected from those conforming to formula (X), wherein R is C12 alkyl or C14 alkyl. In at least one embodiment, the fatty N-methyl-N-glucamide surfactant is selected from those conforming to formula (X), wherein R is C16 alkyl or C18 alkyl.

Amphoteric or zwitterionic surfactant(s) can be included in the composition in an amount ranging from 0.5 wt.-% to about 8 wt.-%, preferably from 1 wt.-% to 4 wt.-% of the total composition.

In at least one embodiment, the amphoteric surfactants are selected from the group consisting of N—$(C_{12}$-$C_{18})$-alkyl- β-aminopropionates and N—($C_{12}$-$C_{18}$)-alkyl-β-iminodipropionates as alkali metal salts and mono-, di-, and trialkylammonium salts; N-acylaminoalkyl-N,N-dimethylacetobetaine, preferably N—($C_8$-$C_{18}$)-acylaminopropyl-N,N-dimethylacetobetaine, ($C_{12}$-$C_{18}$)-alkyl-dimethyl-sulfopropylbetaine, amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., ($C_{12}$-$C_{18}$)-alkyl-dimethyl-amine oxide, fatty acid amidoalkyldimethylamine oxide, and mixtures thereof.

In at least one embodiment, the composition comprises a betaine surfactant. Optionally, the betaine surfactant is selected from C8- to C18-alkylbetaines. In at least one embodiment, the betaine surfactant is selected from the group consisting of cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and laurylbis(2-hydroxypropyl)alphacarboxyethylbetaine and combinations thereof. Optionally, the betaine surfactant is selected from C8- to C18-sulfobetaines. In at least one embodiment, the betaine surfactant is selected from the group consisting of cocodimethylsulfopropylbetaine, stearyldimethylsulfopropylbetaine, lauryldimethyl-sulfoethylbetaine, laurylbis(2-hydroxyethyl)sulfopropylbetaine, and combinations thereof. Optionally, the betaine surfactant is selected from carboxyl derivatives of imidazole, the C8- to C18-alkyldimethylammonium acetates, the C8- to C18-alkyldimethylcarbonylmethylammonium salts, and the C8- to C18-fatty acid alkylamidobetaines, and mixtures thereof. Optionally, the C8- to C18-fatty acid alkylamidobetaine is selected from coconut fatty acid amidopropylbetaine, N-coconut fatty acid amidoethyl-N-[2-(carboxymethoxy)ethyl]glycerol (CTFA name: Cocoamphocarboxyglycinate), and mixtures thereof. A particularly preferred amphoteric or zwitterionic surfactant is cocamidopropyl betaine. Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

Auxiliary

In at least one embodiment, the composition comprises at least one additive common in cosmetology, pharmacy, and dermatology, which are hereinafter called auxiliaries. In at least one embodiment, the composition comprises an auxiliary. In at least one embodiment, the auxiliary is cosmetically acceptable. In at least one embodiment, the auxiliary is selected from the group consisting of oily substances, waxes, emulsifiers, coemulsifiers, solubilizers, cationic polymers, film formers, superfatting agents, refatting agents, foam stabilizers, stabilizers, active biogenic substances, preservatives, preservation boosting ingredients, anti-fungal substance, anti-dandruff agents, dyes or pigments, particulate substances, opacifiers, abrasives, absorbents, anticaking agents, bulking agents, pearlizing agents, direct dyes, perfumes or fragrances, carriers, solvents or diluents, propellants, functional acids, active ingredients, skin-brightening agents, self-tanning agents, exfoliants, enzymes, anti-acne agents, deodorants and anti-perspirants, viscosity modifiers, thickening and gelling agents, pH adjusting agents, buffering agents, anti-oxidants, chelants, astringents, sunscreens, sun protection agents, UV filters, skin conditioning agents, emollients, humectants, occlusive agents, pediculocides, anti-foaming agents, flavouring agents, electrolytes, oxidizing agents and reducing agents. In at least one embodiment, the cosmetically acceptable component is an auxiliary or mixture of auxiliaries.

In at least one embodiment, the composition comprises an oily substance or wax. Preferably the oily substance or wax is selected from the group consisting of silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babassu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, argan oil, abyssinian oil, and coconut oil; synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$-$C_{13}$) fatty acids with linear ($C_6$-$C_{20}$) fatty alcohols; esters of branched ($C_6$-$C_{13}$) carboxylic acids with linear ($C_6$-$C_{20}$) fatty alcohols, esters of linear ($C_6$-$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$-$C_{10}$) fatty acids; esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

In at least one embodiment, the composition comprises an oily substance, which is any fatty substance which is liquid at room temperature (25° C.). In a preferred embodiment, the oily substance is selected from the group consisting of sweet almond oil, caprylic/capric triglycerides, dimethicone, mineral oil, squalane, castor oil, isopropyl isostearate, jojoba oil, dicaprylyl carbonate, isohexadecane, C12-15 alkyl benzoate, and combinations thereof. In at least one embodiment, the composition comprises from 0.001 wt % to 60 wt %, preferably from 0.05 wt % to 50 wt %, even more preferably from 0.1 wt % to 40 wt % of at least one oily substance.

In a preferred embodiment, the wax is selected from the group consisting of carnauba wax, beeswax, candelilla wax, synthetic wax, polyethylene, paraffin wax, microcrystalline wax, hydrogenated vegetable oil, hydrogenated castor oil, rice bran wax, cetyl dimethicone, bis-PEG-18 methyl ether dimethyl silane, and combinations thereof. In at least one embodiment, the composition comprises from 0.001 wt % to 30 wt %, preferably from 0.05 wt % to 20 wt %, even more preferably from 0.1 wt % to 10 wt % of at least one wax.

In at least one embodiment, the composition comprises an emulsifier, coemulsifier or solubilizer. Non-ionic, anionic, cationic or amphoteric surface active compounds can be used as emulsifiers, coemulsifiers and solubilizers.

As nonionogenic surface active compounds, consideration may preferably be given to: addition products of 0 to 30 mol ethylene oxide and/or 0 to 5 mol propylene oxide on linear fatty alcohols with 8 to 22 carbon atoms, on fatty acids with 12 to 22 carbon atoms, on alkyl phenols with 8 to 15 carbon atoms in the alkyl group and on sorbitan or sorbitol esters; ($C_{12}$-$C_{18}$)-fatty acid mono- and diesters of addition products of 0 to 30 mol ethylene oxide on glycerol; glycerol mono- and diesters and sorbitan mono- and diesters of saturated and unsaturated fatty acids with 6 to 22 carbon atoms and optionally their ethylene oxide addition products; addition products of 15 to 60 mol ethylene oxide on castor oil and/or hardened castor oil; polyol and especially polyglycerol polyricinoleate, e.g. polyglycerol polyricinoleate and polyglycerol poly-12-hydroxystearate. Ethoxylated fatty amines, fatty acid amides, fatty acid alkanolamides and mixtures of compounds from several of these classes of substances are also preferably suitable. Polymeric ethers formed by block polymerization of ethylene or propylene oxide known as poloxamers are also suitable.

Suitable ionogenic coemulsifiers are e.g. anionic emulsifiers, such as mono-, di- or triphosphoric acid esters, soaps (e.g. sodium stearate), fatty alcohol sulfates as well as cationic emulsifiers such as mono-, di- and tri-alkyl quats and polymeric derivatives thereof. Amphoteric emulsifiers that are available are preferably alkyl aminoalkyl carboxylic acids, betaines, sulfobetaines and imidazoline derivatives.

Fatty alcohol ethoxylates are used especially preferably. Fatty acid ethoxylates are also preferred. Sodium laureth-11-carboxylate can be used advantageously as ethoxylated alkyl ether carboxylic acid or salts thereof. Polyethylene glycol (60) evening primrose glycerides can be used advantageously as ethoxylated triglycerides.

In at least one embodiment, the composition comprises from 0.1 wt % to 20 wt %, preferably from 0.5 wt % to 10 wt %, even more preferably from 1.0 wt % to 5.0 wt % of at least one emulsifier, coemulsifier and/or solubilizer.

In at least one embodiment, the composition comprises a cationic polymer. Suitable cationic polymers include those known under the INCI designation "polyquaternium", especially polyquaternium-31, polyquaternium-16, polyquaternium-24, Polyquaternium-7, polyquaternium-22, polyquaternium-39, polyquaternium-28, polyquaternium-2, polyquaternium-10, polyquaternium-1, and also polyquaternium-37 & mineral oil & PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

In at least one embodiment, the composition comprises a film former. Film formers are materials which produce a continuous film on skin, hair, or nails such as synthetic or natural polymers and their derivatives. The compositions according to the invention can contain film formers, which are, depending on the intended use, selected from salts of phenylbenzimidazole sulfonic acid, water-soluble polyurethanes, for example C10-polycarbamyl polyglyceryl ester, polyvinyl alcohol, polyvinylpyrrolidone (PVP) copolymers, vinylpyrrolidone/vinyl acetate copolymer or PVP/eicosene copolymers, vinylpyrrolidone/alkene copolymers, for example VP/eicosene copolymer or VP/hexadecene copolymer, PVM/MA copolymer or esters thereof, maleinized polypropylene polymers, water-soluble acrylic acid polymers/copolymers or esters or salts thereof, for example partial-ester copolymers of acrylic/methacrylic acid, polyalkylsilsesquioxanes, polyacrylamide, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate.

In at least one embodiment, the composition comprises a superfatting agent and/or a refatting agent. As superfatting agents it is possible to use substances such as, for example, lanolin, polyethoxylated lanolin derivatives, lecithin, lecithin derivatives, non-ethoxylated and polyethoxylated or acylated lanolin and lecithin derivatives, polyol fatty acid esters such as glyceryl oleate, mono-, di- and triglycerides and/or fatty acid alkanolamides, can preferably be used as overfatting agents or refatting agents. These compounds can also simultaneously serve as foam stabilizers. In a preferred embodiment, the superfatting agent and/or a refatting agent is selected from the group consisting of, lanolin, glyceryl ricinoleate, PEG-8 glyceryl laurate, glyceryl oleate, cocamide MEA, PEG-75 lanolin, and combinations thereof.

In at least one embodiment, the composition comprises a stabiliser. As stabiliser it is possible to use metal salts of fatty acids, such as magnesium, aluminum and/or zinc stearate, for example. In a preferred embodiment, the stabilizer is selected from the group consisting of, aluminum stearate, aluminum isostearates/myristates, magnesium stearate, magnesium cocoate, zinc palmitate, zinc stearate, and combinations thereof.

In at least one embodiment, the composition comprises a biogenic substance.

In at least one embodiment, the composition comprises a preservative, preservation boosting ingredient, anti-fungal agent, and/or anti-dandruff agent. In at least one embodiment, the preservative is selected from the group consisting of benzyl alcohol, piroctone olamine, phenoxyethanol, parabens, pentanediol, benzoic acid/sodium benzoate, sorbic acid/potassium sorbate, and combinations thereof. Other organic acids can also be used to provide antimicrobial protection. In at least one embodiment, the preservation boosting ingredient is selected from the group consisting of anisic acid, lactic acid, sorbitan caprylate, ethylhexylglycerin, caprylyl glycol, octanediol, and mixtures thereof. A suitable preservation boosting ingredient is also disclosed in International patent application PCT/EP2017/065927 (claiming priority from European patent application 16176830.4 filed on 29 June 2016) by Clariant International Ltd (see in particular claim 1 therein), which is incorporated herein by reference. In at least one embodiment, the composition comprises 0.01 to 5.0 wt %, particularly preferably from 0.05 wt % to 1.0 wt % of at least one preservative. Suitable preservatives include the substances listed in the International Cosmetic Ingredient Dictionary and Handbook, 9th Edition with the function "preservatives". In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition comprises a preservative selected from the group consisting of cetyltrimethyl ammonium chloride, cetylpyridinium chloride, benzethonium chloride, diisobutylethoxyethyldimethyl benzylammonium chloride, sodium N-lauryl sarcosinate, sodium-N-palmethyl sarcosinate, lauroyl sarcosine, N-myristoylglycine, potassium-N-laurylsarcosine, trimethylammonium chloride, sodium aluminium chlorohydroxylactate, triethylcitrate, tricetylmethylammonium chloride, 2,4,4'-trichloro-2'-hydroxydiphenylether (Triclosan), phenoxyethanol, 1,5-pentandiol, 1,6-hexandiol, 3,4,4'-trichlorocarbanilide (Triclocarban), diaminoalkylamide, L-lysine hexadecylamide, heavy metal citrate salts, salicylate, piroctose, zinc salts, pyrithione and its heavy metal salts, zinc pyrithione, zinc phenol sulfate, farnesol, ketoconazol, oxiconazol, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, selenium disulfide, piroctone olamine (Octopirox®), methylchloroisothiazolinone, methyl isothiazolinone, methyldibromo glutaronitrile, silver chloride (AgCl), diazolidinyl urea, imidazolidinyl urea, dehydroacetic acid, undecylenic acid, chlorphenesin, proprionic acid, salicylic acid, chloroxylenol, sodium salts of diethylhexylsulfosuccinate, sodiumbenzoate, phenoxyethanol, (RS)-1-(4-chlorophenoxy)-1-imidazol-1-yl-3,3-dimethylbutan-2-one (climbazole), benzyl alcohol, phenoxyisopropanol, parabens such as butyl-, ethyl-, methyl- and propylparaben and their salts, 2-Bromo-2-nitropropane-1,3-diol, polyaminopropyl biguanide, phenoxyisopropanol, iodopropynyl butylcarbamate, benzalkonium chloride, benzethonium chloride, pentandiol, 1,2-octanediol, ethylhexylglycerin, sorbic acid, benzoic acid, lactic acid, imidazolidinyl urea, diazolidinyl urea, dimethylol dimethyl hydantoin (DMDMH), chlorhexidine, sodium salts of hydroxymethyl glycinate, hydroxyethylglycine of sorbic acid, and combinations thereof. In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition is substantially free of parabens.

In at least one embodiment, the composition comprises from 0.1 wt % to 5.0 wt % antimicrobial agents. In at least one embodiment, the antimicrobial agent is chlorhexidine.

In at least one embodiment, the composition comprises an anti-fungal substance. In at least one embodiment, the anti-fungal substance is selected from the group consisting of ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, zinc pyrithione, piroctone olamine (Octopirox®), (RS)-1-(4-chlorophenoxy)-1-imidazol-1-yl-3,3-dimethylbutan-2-one (climbazole), and combinations thereof. In at least one embodiment, the composition comprises a total amount of anti-fungal substance in the composition of from 0.1 wt % to 1.0 wt %. In at least one embodiment, the composition comprises pyridinethione anti-dandruff particulates, for example 1-hydroxy-2-pyridinethione salts, are highly preferred particulate anti-dandruff agents. The concentration of pyridinethione anti-dandruff particulate may ranges from 0.1% to 4.0%, by weight of the formulation, preferably from 0.1% to 3.0%, more preferably from 0.3% to 2.0%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form. Salts formed from other cations, such as sodium, may also be suitable.

In at least one embodiment, the composition comprises a dye or pigment. In at least one embodiment, the composition comprises at least one dye or pigment. Suitable dyes and pigments are disclosed in WO02013/017262A1 in the table spanning pages 36 to 43. In at least one embodiment, the composition comprises a total amount of from 0.01 wt % to 25 wt %, preferably from 0.1 wt % to 15 wt %, even more preferably from 0.5 wt % to 10 wt % of at least one pigment. In at least one embodiment, the inorganic pigment is selected from the group consisting of chalk, ochre, umber, green earth, burnt sienna, graphite, and combinations thereof. The pigments may be white pigments, such as, for example, titanium dioxide or zinc oxide, black pigments, such as, for example, iron oxide black, colored pigments, such as, for example, ultramarine or iron oxide red, lustre pigments, metal effect pigments, pearlescent pigments, and fluorescent or phosphorescent pigments, where preferably at least one pigment is a colored, nonwhite pigment.

In at least one embodiment, the composition comprises a particulate substance. In at least one embodiment, the composition comprises at least one particulate substance. Suitable substances are, for example, substances which are solid at room temperature (25° C.) and are in the form of particles. Suitable substances are, for example, substances which serve as opacifiers, abrasives, absorbents, anti-caking agents, bulking agents or performance fillers. In at least one embodiment, the particulate substance is selected from the group consisting of silica, silicates (e.g. sepiolite, montmorillonite, bentonite, kaolin, hectorite), aluminates, clay earths, mica, talc, starch, perlite, charcoal, pulp powder, seed powder, insoluble salts, in particular insoluble inorganic metal salts, metal oxides (e.g. titanium dioxide), minerals and insoluble polymer particles, such as polyamide derivatives (e.g. nylon-12, nylon-6, polyamide-5), silicones (e.g. polymethylsilsesquioxane), polyesters (e.g. polyester-12), polyethylene and polymethyl methacrylates.

In at least one embodiment, the composition comprises pearlizing agents. In at least one embodiment, the composition comprises at least one pearlizing agent. In at least one embodiment, the particulate substance is selected from the group consisting of, fatty acid monoalkanolamides, fatty acid dialkanolamides, monoesters or diesters of alkylene glycols, especially ethylene glycol and/or propylene glycol or oligomers thereof, with higher fatty acids, e.g. palmitic acid, stearic acid and behenic acid, monoesters or polyesters of glycerol with carboxylic acids, fatty acids and metal salts thereof, ketosulfones or mixtures of the aforementioned compounds.

In at least one embodiment, the composition comprises a direct dye. In at least one embodiment, the composition comprises at least one direct dye. Preferred among the direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxy-ethyl)amino-2-nitro-4-[di(2-hydroxyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl)azo]-7-(trimethylammonio)-2-naphthol chloride (C.I. 12250;

Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio)phenyl]azo}pyrazol-5-one chloride (C.I. 12719; Basic Yellow No. 57) and 2,6-diamino-3-[(pyridin-3-yl)azo]pyridine as well as the salts thereof.

In at least one embodiment, the composition comprises a perfume or fragrance ingredient. Individual fragrance compounds, e.g. the synthetic products of the type of esters, ethers, aldehydes, ketones, alcohols and hydrocarbons can be used as fragrance or perfume oils. Fragrance compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allylcyclohexyl propionate, styrallyl propionate and benzyl salicylate. Perfume oils can also contain mixtures of natural odoriferous substances that can be obtained from vegetable or animal sources. Essential oils of lower volatility, which are used mostly as flavor components, are also suitable as perfume oils.

In at least one embodiment, the composition comprises a carrier, solvent or diluent. In at least one embodiment, the composition comprises a solvent, wherein the solvent comprises water and/or alcohol. Solvent is useful for providing the compounds used in present invention in liquid form. In at least one embodiment, the solvent is cosmetically acceptable. In at least one embodiment, the composition comprises at least 10 wt % water. Water is useful for economic reasons but also because it is cosmetically acceptable. Optionally the composition comprises water-miscible or water-soluble solvents such as lower alkyl alcohols. In at least one embodiment, the composition comprises C1-C5 alkyl monohydric alcohols, preferably C2-C3 alkyl alcohols. The alcohols which may be present are in particular lower monohydric or polyhydric alcohols having 1 to 4 carbon atoms customarily used for cosmetic purposes, such as preferably ethanol and isopropanol. Optionally, the composition comprises a water-soluble polyhydric alcohol. In at least one embodiment, the water-soluble polyhydric alcohols are polyhydric alcohols having two or more hydroxyl groups in the molecule. In a preferred embodiment, the composition comprises a solvent selected from the group consisting of water, glycols, ethanol, and combinations thereof. In a preferred embodiment, the composition comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof. Natural solvents can also be used. In at least one embodiment, the composition comprises a solvent selected from the group consisting of plant oil, honey, plant-derived sugar compositions, and mixtures thereof. In at least one embodiment, the composition comprises from 0.5 wt % to 90 wt %, preferably from 1.0 wt % to 80 wt %, even more preferably from 5.0 wt % to 70 wt % of at least one carrier, solvent and/or diluent.

In at least one embodiment, the composition comprises a propellant. In at least one embodiment, the propellant is selected from compressed gas propellants and liquefied gas propellants. In at least one embodiment, the compressed gas propellants are selected from the group consisting of air, nitrogen ($N_2$), nitrous oxide ($N_2O$), carbon dioxide ($CO_2$), and mixtures thereof. In at least one embodiment, the liquefied gas propellants are selected from the group consisting of dimethylether (DME), 1,1-difluoroethane (HFC-152a), 1,1,1,2-tetrafluoroethane (HFC-134a), pentane, n-butane, iso-butane, propane, trans-1,3,3,3-tetrafluoropropene (HF0-1234ze), and mixtures thereof.

In at least one embodiment, the composition comprises a functional acid or an active ingredient. Functional acids and active ingredients are substances used to impart a clinical functionality to the skin or hair upon application. Functional acids and active ingredients are for example used as exfoliants, skin-brightening agents, self-tanning agents, anti-acne agents and anti-ageing agents.

In at least one embodiment, the composition comprises a deodorant or an anti-perspirants. In at least one embodiment, the composition comprises a deodorising agent. In at least one embodiment, the deodorising agent is selected from the group consisting of allantoin, bisabolol, and combinations thereof. The composition may comprise an antiperspirant. As antiperspirant it is possible to use aluminium chloride, aluminum chloride hydroxide, aluminum chloride dihydroxide, aluminum chlorohydrex polyethylene glycol complex, magnesium zirconium complexes or aluminum zirconium chloride hydroxide, for example.

In at least one embodiment, the composition comprises at least one viscosity modifier or thickening and/or gelling agent. The desired viscosity and rheology profile of the compositions can be adjusted by adding further thickeners and gelling agents. The viscosity-modifying substance is preferably a thickening polymer. In at least one embodiment, the thickening polymer selected from the group consisting of: copolymers of at least one first monomer type, which is chosen from acrylic acid and methacrylic acid, and at least one second monomer type, which is chosen from esters of acrylic acid and ethoxylated fatty alcohol, crosslinked polyacrylic acid, crosslinked copolymers of at least one first monomer type, which is chosen from acrylic acid and methacrylic acid, and at least one second monomer type, which is chosen from esters of acrylic acid with C10- to C30-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated C10- to C30-alcohol and a third monomer type, chosen from C1-to C4-aminoalkyl acrylates; copolymers of two or more monomers chosen from acrylic acid, methacrylic acid, acrylic esters and methacrylic esters; copolymers of vinylpyrrolidone and ammonium acryloyldimethyltaurate; copolymers of ammonium acryloyldimethyltaurate and monomers chosen from esters of methacrylic acid and ethoxylated fatty alcohols, hydroxyethylcellulose, hydroxypropylcellulose, hydroxypropylguar, glyceryl polyacrylate, glyceryl polymethacrylate, copolymers of at least one C2-, C3- or C4-alkylene and styrene, polyurethanes, hydroxypropyl starch phosphate, polyacrylamide, copolymer of maleic anhydride and methyl vinyl ether crosslinked with decadiene, carob seed flour, gums such as guar gum, karaya gum, xanthan gum or dehydroxanthan gum, carrageenan, hydrolyzed corn starch; copolymers of polyethylene oxide, fatty alcohols and saturated methylenediphenyl diisocyanate (e.g. PEG-150/stearyl alcohol/SMDI copolymer), and mixtures thereof. In a preferred embodiment, the viscosity modifier or thickening and/or gelling agent is selected from the group consisting of carbomers, acrylates copolymers, xanthan gum, hydroxyethylcellulose, laureth-2, and combinations thereof.

In at least one embodiment, the composition comprises an alkalizing agent or pH adjusting agent. In at least one embodiment, ammonia or caustic soda is suitable, but water-soluble, physiologically tolerable salts of organic and inorganic bases can also be considered. Optionally, the pH adjusting agent is selected from ammonium hydrogen carbonate, ammonia, monoethanolamine, ammonium hydroxide, ammonium carbonate. In at least one embodiment, the alkalizing agents is selected from the group consisting of 2-amino-2-methyl-1-propanol, 2-amino-2-methyl-1,3-propanediol, 2-amino-2-ethyl-1,3-propanediol, tris(hydroxylmethyl)-aminomethane, 2-amino-1-butanole, tris-(2-hydroxypropyl)-amine, 2,2-iminobisethanol, lysine, iminourea (guanidine carbonate), tetrahydro-1,4-oxazine, 2-amino-5-guanidin-valeric acid, 2-aminoethansulfonic acid, diethanolamine, triethanolamine, N-methyl ethanolamine, isopropanolamine, diisopropanolamine, triisopropanolamine, glucamine, sodium hydroxide, potassium hydroxide, lithium hydroxide and magnesium oxide, and mixtures thereof. To establish an acidic pH value, an acid can be included.

In at least one embodiment, the composition/formulation comprises an anti-oxidant. In at least one embodiment, the anti-oxidant is selected from the group consisting of amino acids, peptides, sugars, imidazoles, carotinoids, carotenes, chlorogenic acid, lipoic acid, thiols, thiol glycosyl esters, thiol N-acetyl esters, thiol methyl esters, thiol ethyl esters, thiol propyl esters, thiol amyl esters, thiol butyl esters, thiol lauryl esters, thiol palmitoyl esters, thiol oleyl esters, thiol linoleyl esters, thiol cholesteryl esters, thiol glyceryl esters, dilaurylthiodipropionate, distearylthiodipropionate, thiodipropionic acid, metal chelators, hydroxy acids, fatty acids, folic acids, vitamin C, tocopherol, vitamin A, stilbenes, derivatives and combinations thereof.

In at least one embodiment, the composition/formulation comprises a chelant. In at least one embodiment, the chelant is selected from the group consisting of EDTA, caprylyhdroxamic acid, oxalate derivatives, disodium hydroxyethyl-iminodiacetate, galacturonic acid and derivatives, glucuronic acid and derivatives, lauroyl ethylenediamine triacetic acid, methyl dihydroxybenzoate, trisodium ethylenediamine disuccinate, phytic acid, itaconic acid, propane tricarboxylic acid, citric acid and derivatives (e.g. diammonium citrate, bismuth citrate and acetyl trihexyl citrate 2,6-dicarboxy pyridine), phosphoric and phosphonic acid derivatives (e.g. diethylenetriamine pentamethylene phosphonic acid, disodium azacycloheptane diphosphonate, glycereth-26 phosphate, disodium pyrophosphate, disodium salicylphosphate, aminotrimethylene phosphonic acid, phosphonobutanetricarboxylic acid, potassium trisphosphonomethylamine oxidebeta-alanine diacetic acid or cyclohexanediamine tetraacetic acid). In at least one embodiment, the chelant is selected from the group consisting EDTA, oxalate derivatives, disodium salicylphosphate, and combinations thereof.

In at least one embodiment, the composition comprises an astringent. In at least one embodiment, the astringent is selected from the group consisting of magnesium oxide, aluminium oxide, titanium dioxide, zirconium dioxide, zinc oxide, oxide hydrates, aluminium oxide hydrate (boehmite) and hydroxide, chlorohydrates of calcium, magnesium, aluminium, titanium, zirconium or zinc.

In at least one embodiment, the composition comprises a sun protection agent and/or UV filter. Suitable sun protection agents and UV filters are disclosed in WO02013/017262A1 (published on 7 Feb. 2013), from page 32, line 11 to the end of page 33. The photoprotective substances include, in particular, all of the photoprotective substances specified in EP1084696, which is incorporated herein by reference. In another preferred embodiment of the invention, the compositions according to the invention contain one or more substances selected from inorganic and organic UV filters and especially preferably are in the form of sunscreen compositions.

In at least one embodiment, the composition comprises a skin conditioning agent. Skin conditioning agents such as emollients, humectants and occlusive agents are ingredients which help to maintain the soft and smooth appearance of the skin or which help to improve the condition of dry or damaged skin. In at least one embodiment, the skin conditioning agent is selected from the group consisting of oily substances (description see above), functional acids or active ingredients (description see above), fatty acid N-alkylpolyhydroxyalkyl amides, fatty acids, triglycerides, panthenol, allantoin, bisabolol, glycerol, sorbitol, urea and derivatives thereof, trehalose, erythrulose, pyrrolidone carboxylic acid (PCA) and its salts, polyglucuronic acid, gluconolactone, petrolatum, ubichinon-10 and ubiquinol. In a preferred embodiment, the skin conditioning agent is selected from the group consisting of urea, glycerine, pyrrolidone carboxylic acid (PCA) and its salts, panthenol, petrolatum, and combinations thereof.

In at least one embodiment, the composition comprises an anti-foaming agent. Antifoams are chemicals which reduce the tendency of finished products to generate foam on shaking or agitation. In at least one embodiment, the anti-foaming agent is selected from the group consisting of alcohols (e.g. ethanol, isopropyl alcohol or propyl alcohol), alkoxylated alcohols (e.g. laureth-5 butyl ether), silicon oils and resins (e.g. dimethicone and its derivatives such as cetyl dimethicone, phenyl dimethicone, PEG/PPG-12/18 dimethicone and hydrogen trifluoropropyl dimethicone, trimethylsiloxysilicate/dimethicone crosspolymer or polysilicone-10) and hydrophobic silica derivatives (e.g. silica silylate).

In at least one embodiment, the composition comprises a flavouring agent. In at least one embodiment, the flavouring agent is selected from the group consisting of 1-acetonaphthalene, 1-decen-3-ol, p-methylbenzaldehyde, p-propenylphenyl methyl ether, aspartame, benzaldehyde, bromocinnamal, calcium cyclohexylsulfamate, calcium o-benzolufimide, carvone, cinnamic aldehyde, 3,7-dimethyl-6-octenoic acid, fruit sugar, glucose, glucosyl stevioside, honey, 3-methyl-1-butanol, 4-hydroxy-3-methoxy-1-propenylbenzene, malt sugar, menthol, eucalyptol, thymol, potassium 6-methyl-1,2,2-oxathiazin-4(3H)-one 2,2'-dioxide, isodulcitol, saccharine, stevioside, 1',4,6'-trichloro-galacto-sucrose, sorbitol, saccharose, sodium saccharin, methyl salicylate vanillaldehyde, xylite, xylose and plant extracts.

In at least one embodiment, the composition comprises an electrolyte. In at least one embodiment, the electrolyte is selected from the group consisting of salts preferably ammonium or metal salts, especially preferably halides, for example $CaCl_2$, $MgCl_2$, LiCl, KCl and NaCl, carbonates, hydrogen carbonates, phosphates, sulfates, nitrates, especially preferably sodium chloride, sodium fluoride, sodium monofluorophosphate, stannous fluoride, and/or organic salts.

In at least one embodiment, the composition comprises an oxidizing or reducing agent. In at least one embodiment, the oxidizing or reducing agent is selected from the group consisting of ammonium persulfate, calcium peroxide, hydrogen peroxide, hypochlorous acid, sodium hypochlorite, potassium monopersulfate, sodium carbonate peroxide, ammonium thioglycolate, cysteine, glutathione, hydroquinone, mercaptopropionic acid, superoxide dismutase, thioglycerin, thioglycolic acid, thiolactic acid, sodium sulfite, sodium thioglycolate, potassium thioglycolate, and cysteine.
Hair Conditioning Agent In at least one embodiment, the composition comprises a hair conditioning agent. In at least one embodiment, the hair conditioning agent is a water insoluble, water dispersible, non-volatile, liquid that forms emulsified, liquid particles. In at least one embodiment, the hair conditioning agent is a silicone (e.g., silicone oil, cationic silicone, silicone gum, high refractive silicone, and silicone resin), an organic conditioning oil (e.g., hydrocarbon oils, polyolefins, and fatty esters), or combinations thereof.

In at least one embodiment, the hair conditioning agent is a silicone, and wherein the composition comprises from 0.01% to 10%, or from 0.1% to 5% silicone hair conditioning agent, by total weight of the composition. Suitable silicone hair conditioning agents, and optional suspending agents for the silicone, are described in U.S. Pat. No. 5,104,646. In at least one embodiment, the composition comprises a silicone gum selected from the group consisting of polydimethylsiloxane, (polydimethylsiloxane) (methylvinylsiloxane) copolymer, poly(dimethylsiloxane) (diphenylsiloxane) (methylvinylsiloxane) copolymer, and mixtures thereof. In at least one embodiment, the composition comprises a terminal aminosilicone. "Terminal aminosilicone" as defined herein means silicone comprising one or more amino groups at one or both ends of the silicone backbone.

In at least one embodiment, the composition comprises a high melting point fatty compound. The high melting point fatty compound has a melting point of 25° C. or higher. In at least one embodiment, the high melting point fatty compound is selected from the group consisting of a fatty alcohol, fatty acid, fatty alcohol derivative, fatty acid derivative, and mixtures thereof. Non-limiting examples of the high melting point compounds are found in International Cosmetic Ingredient Dictionary, Fifth Edition, 1993, and CTFA Cosmetic Ingredient Handbook, Second Edition, 1992. The composition may comprise from 0.1% to 40%, or from 1% to 30%, or from 1.5% to 16%, or from 1.5% to 8% of a high melting point fatty compound, by total weight of the composition.

In at least one embodiment, the composition comprises a cationic surfactant. In an embodiment, cationic surfactant is according to Formula (C):

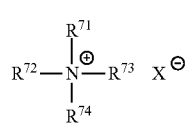

(C)

wherein
at least one of $R^{71}$, $R^{72}$, $R^{73}$ and $R^{74}$ is selected from an aliphatic group of from 8 to 30 carbon atoms, an aromatic, alkoxy, polyoxyalkylene, alkylamido, hydroxyalkyl, aryl, or an alkylaryl group having up to 22 carbon atoms;
the remainder of $R^{71}$, $R^{72}$, $R^{73}$ and $R^{74}$ are independently selected from the group consisting of an aliphatic group consisting of from 1 to 22 carbon atoms, and an aromatic, alkoxy, polyoxyalkylene, alkylamido, hydroxyalkyl, aryl or alkylaryl group having up to 22 carbon atoms;
X is selected from the group consisting of: halogen, acetate, citrate, lactate, glycolate, phosphate, nitrate, sulfonate, sulfate, alkylsulfate, alkyl sulfonate radicals, and combinations thereof.

In at least one embodiment, the cationic surfactant is selected from the group consisting of cetyltrimonium chloride (CTAC), stearyltrimonium chloride (STAC), behentrimonium methosulfate, stearoylamidopropyldimethyl amine (SAPDMA), distearyldimethylammonium chloride, and mixtures thereof.
Hairstyling Polymers In at least one embodiment, the composition comprises a hairstyling polymer. In at least one embodiment, the hairstyling polymer is selected from the group consisting of: amphoteric hairstyling polymers, zwitterionic hairstyling polymers, anionic hairstyling polymers, non-ionic hairstyling polymers, cationic hairstyling polymers, and mixtures thereof. In at least one embodiment, the composition comprises from 0.01% to 20%, or from 0.01% to 16%, or from 0.01% to 10%, or from 1% to 8%, or from 2% to 6% of hairstyling polymer.
Cosmetic, Dermatological or Pharmaceutical Compositions In at least one embodiment, the cosmetic, dermatological or pharmaceutical composition according to the invention comprise the one or more polymers (I) in a total amount of from 0.01 to 10 wt %, preferably from 0.1 to 5.0 wt %, even more preferably from 0.25 to 2.0 wt %. In at least one embodiment, the cosmetic, dermatological or pharmaceutical compositions comprise further from 0.5 wt % to 90 wt %, preferably from 1.0 wt % to 80 wt %, even more preferably from 5.0 wt % to 70 wt % of at least one carrier, solvent and/or diluent. Carriers, solvents and/or diluents are listed above. In at least one embodiment, the carrier, solvent and/or diluent is selected from the group consisting of water, glycols, ethanol, and combinations thereof.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

In at least one embodiment, the cosmetic, dermatological or pharmaceutical composition is for use on skin. In at least one embodiment, the composition is for use on the face, the neck, the body and/or around the eye area. In at least one embodiment, the composition is an emulsion or gel, preferably an oil-in-water (o/w), cream gel, hydro-alcoholic gel or hydrogel composition. In a preferred embodiment, the composition has a viscosity from 100 000 to 200 000 mPa·s, preferably from 1 000 to 100 000 mPa·s, even more preferably from 2 000 to 50 000 mPa·s and very preferably from 5 000 to 30 000 mPa·s (measured at 25° C., Brookfield RVT, T-C spindle at 20 revolutions per minute).

In at least one embodiment, the composition is a body or face care composition such as face creams, neck creams, body lotions, body milks, face serums, blemish balm creams, hand creams, foot creams, body butters, lip creams, eye creams, after-sun lotions, make-up removing lotions or body mists, diaper creams or baby lotions. Optionally the body or face care composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Emulsifiers, coemulsifiers and/or solubilizers are listed above. Optionally the body or face care composition comprises from 0.01 wt % to 40 wt %, preferably from 0.05 wt % to 30 wt %, even more preferably from 0.1 wt % to 20 wt % of at least one oily substance. Oily substances are listed above. Optionally the body or face care composition comprises from 0.01 wt % to 20 wt %, preferably from 0.05 wt % to 10 wt %, even more preferably from 0.1 wt % to 5.0 wt % of at least one wax. Waxes are listed above. Optionally the body or face care composition comprises from 0.01 wt % to 15 wt %, preferably from 0.1 wt % to 10 wt %, even more preferably from 0.3 wt % to 5.0 wt % of at least one viscosity modifier or thickening and/or gelling agent. Viscosity modifiers or thickening and/or gelling agents are listed above. Optionally the body or face care composition comprises from 0.001 wt % to 5.0 wt %, preferably from 0.05 wt % to 3.0 wt %, even more preferably from 0.1 wt % to 1.0 wt % of at least one skin conditioning agent. Skin conditioning agents are listed above. Optionally the body or face care composition comprises from 0.001 wt % to 10 wt %, preferably from 0.05 wt % to 5.0 wt %, even more preferably from 0.1 wt % to 3.0 wt %, most preferably from 0.05 wt % to 1.0 wt % of at least one antioxidant. Antioxidants are listed above. Optionally the body or face care composition comprises from 0.001 wt % to 5.0 wt %, preferably from 0.01 wt % to 3.0 wt %, even more preferably from 0.1 wt % to 2.0 wt % of at least one biogenic active substance. Optionally the body or face care composition comprises from 0.01 wt % to 4.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. Optionally the body or face care composition comprises from 0.01 wt % to 3.0 wt %, preferably from 0.05 wt % to 2.0 wt %, even more preferably from 0.1 wt % to 1.0 wt % of at least one perfume or fragrance ingredient. Perfume or fragrance ingredients or are listed above. Optionally the body or face care composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a skin-whitening composition. Optionally the skin-whitening composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Emulsifiers, coemulsifiers and/or solubilizers are listed above. Optionally the skin-whitening composition comprises from 0.01 wt % to 10 wt %, preferably from 0.1 wt % to 7.5 wt %, even more preferably from 0.3 wt % to 5.0 wt % of at least one viscosity modifier or thickening and/or gelling agent. Viscosity modifiers or thickening and/or gelling agents are listed above. Optionally the skin-whitening composition comprises from 0.01 wt % to 5.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. In a preferred embodiment, the skin-whitening composition has a pH value from 1.0 to 8.0, preferably from 2.0 to 7.0, even more preferably from 3.0 to 6.0.

In at least one embodiment, the composition is a self-tanning composition. Optionally the self-tanning composition comprises from 0.001 wt % to 40 wt %, preferably from 0.05 wt % to 30 wt %, even more preferably from 0.1 wt % to 20 wt % of at least one oily substance. Oily substances are listed above. Optionally the self-tanning composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a cleansing composition such as body washes, face washes, micellar waters or gels, body scrubs, face peeling, facial exfoliators, liquid soaps, bath additives, bubble baths, shower creams or milks, shower foams and face masks. Optionally the cleansing composition comprises from 0.5 wt % to 25 wt %, preferably from 1.0 wt % to 20 wt %, even more preferably from 2.0 wt % to 15 wt % of at least one surfactant. Surfactants are listed above. Optionally the cleansing composition comprises from 0.01 wt % to 15 wt %, preferably from 0.1 wt % to 10 wt %, even more preferably from 0.5 wt % to 5.0 wt % of at least one viscosity modifier or thickening agent. Viscosity modifier or thickening agents are listed above. Optionally the cleansing composition comprises from 0.01 wt % to 15 wt %, preferably from 0.05 wt % to 10 wt %, even more preferably from 0.5 wt % to 5.0 wt % of at least one particulate substance. Particulate substances are listed above. Optionally the cleansing composition comprises from 0.001 wt % to 30 wt %, preferably from 0.05 wt % to 20 wt %, even more preferably from 0.1 wt % to 10 wt % of at least one oily substance. Oily substances are listed above. Optionally the cleansing composition comprises from 0.05 wt % to 15 wt %, preferably from 0.1 wt % to 10 wt %, even more preferably from 0.5 wt % to 5.0 wt % of at least one functional acid or/and an active ingredient. Functional acids or/and an active ingredients are listed above. Optionally the cleansing composition comprises from 0.001 wt % to 5.0 wt %, preferably from 0.05 wt % to 3.0 wt %, even more preferably from 0.1 wt % to 1.0 wt % of at least one electrolyte. Electrolytes are listed above. Optionally the cleansing composition comprises from 0.01 wt % to 5.0 wt %, preferably from 0.1 wt % to 3.0 wt %, even more preferably from 0.4 wt % to 1.0 wt % of at least one preservative or preservation boosting ingredient. Optionally the cleansing composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a sun care composition such as sun sprays, sun milks, sun lotions, sun gels. Body and face care compositions with sun protection agents and/or UV filters such as day creams, hand creams, foundations, lip balms and face serums can also serve as sun care compositions. Optionally the sun care composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Optionally the sun care composition comprises from 0.001 wt % to 50 wt %, preferably from 0.05 wt % to 40 wt %, even more preferably from 0.1 wt % to 30 wt % of at least one oily substance. Oily substances are listed above. Optionally the sun care composition comprises from 0.001 wt % to 30 wt %, preferably from 0.05 wt % to 20 wt %, even more preferably from 0.1 wt % to 10 wt %, most preferably from 0.05 wt % to 5.0 wt % of at least one sun protection agent and/or UV filter. Sun protection agents and/or UV filters are listed above. Optionally the sun care composition comprises from 0.1 wt % to 10 wt %, preferably from 0.5 wt % to 7.5 wt %, even more preferably from 1.0 wt % to 5.0 wt % of at least one film former. Film formers are listed above. Optionally the sun care composition comprises from 0.01 wt % to 5.0 wt %, preferably from 0.1 wt % to 3. wt %, even more preferably from 0.4 wt % to 1.0 wt % of at least one preservative or preservation boosting ingredient. Preservatives or preservation boosting ingredients are listed above. Optionally the sun care composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a color cosmetic composition such as foundations, fluid Illuminators, eye brow products, primers, concealers, blushes, bronzers, eye shadows, eye lash products, eye liners, face powders, lipsticks, lip glosses, lip balms or nail polishes. Optionally the color cosmetic composition comprises from 0.01 wt % to 25 wt %, preferably from 0.1 wt % to 15 wt %, even more preferably from 0.5 wt % to 10 wt % of at least one dye or pigment. Dyes and pigments are listed above. Optionally the color cosmetic composition comprises from 0.01 wt % to 15 wt %, preferably from 0.05 wt % to 10 wt %, even more preferably from 0.5 wt % to 5.0 wt % of at least one particulate substance. Optionally the color cosmetic composition comprises from 0.001 wt % to 60 wt %, preferably from 0.05 wt % to 50 wt %, even more preferably from 0.1 wt % to 40 wt % of at least one oily substance. Oily substances are listed above. Optionally the color cosmetic composition comprises from 0.001 wt % to 30 wt %, preferably from 0.05 wt % to 20 wt %, even more preferably from 0.1 wt % to 10 wt % of at least one wax. Waxes are listed above. Optionally the color cosmetic composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Optionally the color cosmetics composition comprises from 0.01 wt % to 5.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. Optionally the color cosmetic composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a face toner. Optionally the face toner composition comprises from 0.001 wt % to 5.0 wt %, preferably from 0.05 wt % to 3.0 wt %, even more preferably from 0.1 wt % to 1.0 wt % of at least one skin conditioning agent. Skin conditioning agents are listed above. Optionally the face toner composition comprises from 0.01 wt % to 15 wt %, preferably from 0.1 wt % to 10 wt %, even more preferably from 0.5 wt % to 5.0 wt % of at least one viscosity modifier or thickening agent. Optionally the face toner composition comprises from 0.01 wt % to 5.0 wt %, preferably from 0.1 wt % to 3.0 wt %, even more preferably from 0.4 wt % to 1.0 wt % of at least one preservative or preservation boosting ingredient.

In at least one embodiment, the composition is a bar soap or syndet composition. Optionally the bar soap or syndet composition comprises from 1.0 wt % to 50 wt %, preferably from 2.0 wt % to 30 wt %, even more preferably from 5.0 wt % to 20 wt % of at least one surfactant. Surfactants are listed above. Optionally the bar soap or syndet composition comprises from 0.01 wt % to 20 wt %, preferably from 0.05 wt % to 15 wt %, even more preferably from 0.5 wt % to 10 wt % of at least one particulate substance. Particulate substances are listed above. Optionally the bar soap or syndet composition comprises from 0.001 wt % to 5.0 wt %, preferably from 0.05 wt % to 3.0 wt %, even more preferably from 0.1 wt % to 1.0 wt % of at least one electrolyte. Electrolytes are listed above. Optionally the bar soap or syndet composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a deodorizing and/or antiperspirant composition. In at least one embodiment, the composition is in the form of a cream, a roll-on, a solid, an aerosol or a gel. Optionally the deodorizing and/or antiperspirant composition comprises from 0.001 wt % to 10 wt %, or from 0.01 wt % to 9.0 wt %, or from 0.05 wt % to 8.0 wt %, or from 0.1 wt % to 5.0 wt % of at least one antiperspirant and/or deodorizing agent. Optionally the deodorizing and/or antiperspirant composition comprises 0.01 wt % to 3.0 wt %, preferably from 0.05 wt % to 2.0 wt %, even more preferably from 0.1 wt % to 1.0 wt % of at least one perfume or fragrance ingredient. Perfume or fragrance ingredients or are listed above. Optionally the deodorizing and/or antiperspirant composition comprises from 0.5 wt % to 60 wt %, preferably from 1.0 wt % to 50 wt %, even more preferably from 2.0 wt % to 40 wt % of at least one propellant. Propellants are listed above. Optionally the deodorizing and/or antiperspirant composition comprises from 0.01 wt % to 20 wt %, preferably from 0.1 wt % to 10 wt %, even more preferably from 0.5 wt % to 5.0 wt % of at least one further auxiliary. Auxiliaries are listed above.

In at least one embodiment, the composition is a depilating composition.

In at least one embodiment, the composition is a shaving composition.

In at least one embodiment, the composition is a fragrance composition.

In at least one embodiment, the composition is a hand sanitizing composition.

In at least one embodiment, the cosmetic, dermatological or pharmaceutical composition is for use on hair and/or scalp. In at least one embodiment, the composition is an emulsion or gel, preferably an oil-in-water (o/w), cream gel, hydro-alcoholic gel or hydrogel composition. In a preferred embodiment, the hair care composition has a viscosity from 100 000 to 150 000 mPa·s, preferably from 1 000 to 100 000 mPa·s, more preferably from 2 000 to 50 000 mPa·s and very preferably from 5 000 to 30 000 mPa·s (25° C., Brookfield RVT, T-C spindle at 20 revolutions per minute).

In at least one embodiment, the composition is a shampoo composition. Optionally the shampoo composition comprises from 0.5 wt % to 30 wt %, preferably from 1.0 wt % to 15 wt %, even more preferably from 2.0 wt % to 10 wt % of at least one surfactant. Surfactants are listed above. In at least one embodiment, the surfactant is selected from the group consisting of sodium laureth sulfate, sodium lauryl sulfate, ammonium lauryl sulfate, sodium lauroyl sarcosinate, sodium methyl cocoyl taurate, cocamidopropyl betaine, sodium cocoyl glutamate, lauryl glucoside, cocoyl methyl glucamide, and combinations thereof. Optionally the shampoo composition comprises from 0.1 wt % to 10 wt %, preferably from 0.5 wt % to 7.5 wt %, even more preferably from 1.0 wt % to 5.0 wt % of at least one cationic polymer. Optionally the shampoo composition comprises from 0.1 wt % to 15 wt %, preferably from 0.5 wt % to 10 wt %, even more preferably from 1.0 wt % to 5.0 wt % of at least one pearlizing agent. Optionally the shampoo composition comprises from 0.001 wt % to 5.0 wt %, preferably from 0.05 wt % to 3.0 wt %, even more preferably from 0.1 wt % to 1.0 wt % of at least one electrolyte. Optionally the shampoo composition comprises from 0.01 wt % to 15 wt %, preferably from 0.1 wt % to 10 wt %, even more preferably from 0.5 wt % to 5.0 wt % of at least one viscosity modifier or thickening agent. Viscosity modifier or thickening agents are listed above. Optionally the shampoo composition comprises from 0.01 wt % to 5.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. Optionally the shampoo composition comprises from 0.01 wt % to 20 wt %, preferably from 0.1 wt % to 10 wt %, even more preferably from 0.5 wt % to 5.0 wt % of at least one further auxiliary. Auxiliaries are listed above. In a preferred embodiment, the shampoo composition has a pH value of from 2.0 to 8.0, preferably from 3.0 to 7.0, even more preferably from 4.0 to 6.0.

In at least one embodiment, the composition is a hair conditioning and/or hair and/or scalp treatment composition such as leave-in and rinse-off conditioners, masks, lotions, combing creams, detangling creams, anti-frizz liquids, hair serums, scalp serums, color protection creams. Optionally the hair conditioning and/or hair and/or scalp treatment composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of cetearyl alcohol, cetrimonium chloride, behentrimonium chloride, steartrimonium chloride, cetyl alcohol, stearyl alcohol, stearic acid, isostearamidopropyl dimethylamine, and combinations thereof. Optionally the hair conditioning and/or hair and/or scalp treatment composition comprises from 0.01 wt % to 20 wt %, preferably from 0.05 wt % to 10 wt %, even more preferably from 0.1 wt % to 5.0 wt % of at least one oily substance. Oily substances are listed above. In at least one embodiment, the oily substance is selected from the group consisting of dimethicone, squalene, amodimethicone, argan oil, jojoba oil, cyclopentasiloxane, mineral oil, castor oil, shea butter, and combinations thereof. Optionally the hair conditioning and/or hair and/or scalp treatment composition comprises from 0.1 wt % to 10 wt %, preferably from 0.5 wt % to 7.5 wt %, even more preferably from 1.0 wt % to 5.0 wt % of at least one cationic polymer. Cationic polymers are listed above. In at least one embodiment, the cationic polymer is selected from the group consisting of polyquaternium-10, guar hydroxypropyltrimonium chloride, polyquaternium-7, polyquaternium-6, and combinations thereof. Optionally the hair conditioning and/or hair and/or scalp treatment composition comprises from 0.001 wt % to 5.0 wt %, preferably from 0.01 wt % to 3.0 wt %, even more preferably from 0.1 wt % to 2.0 wt % of at least one biogenic active substance. Biogenic active substances are listed above. In at least one embodiment, the biogenic active substance is selected from the group aloe collagen hydrolysates, bisabolol, allantoin, hydrolyzed wheat protein, hydrolyzed silk, hydrolyzed keratin, amino acids and its derivatives, glycoproteins, and combinations thereof. Optionally the hair conditioning and/or hair and/or scalp treatment composition comprises from 0.01 wt % to 5.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. In at least one embodiment, the preservative or preservation boosting ingredient is selected from the group consisting of sodium benzoate, methylparaben, phenoxyethanol, methylisothiazolinone, DMDM hydantoin, methylchloroisothiazolinone, pyrithione, octopirox, and combinations thereof. Optionally the hair conditioning and/or hair and/or scalp treatment composition comprises from 0.01 wt % to 20 wt %, preferably from 0.1 wt % to 10 wt %, even more preferably from 0.5 wt % to 5.0 wt % of at least one further auxiliary. Auxiliaries are listed above. In a preferred embodiment, the hair conditioning and/or hair and/or scalp treatment composition has a pH value from 2.0 to 8.0, preferably from 3.0 to 7.0, even more preferably from 4.0 to 6.0.

In at least one embodiment, the composition is a hair styling composition such as mousses, gels, sprays and waxes. Optionally the hair styling composition comprises from 0.1 wt % to 10 wt %, preferably from 0.5 wt % to 7.5 wt %, even more preferably from 1.0 wt % to 5.0 wt % of at least one film former or hairstyling polymer. Film formers and hairstyling polymers are listed above. In at least one embodiment, the film former is selected from the group consisting of PVP, VP/VA copolymer, styrene/acrylates copolymer, acrylates copolymer, butyl ester of PVM/MA copolymer, hydroxyethylcellulose, chitosan, polyquaternium-10, polypropylsilsesquioxane, polyurethane-64, and combinations thereof. Optionally the hair styling composition comprises from 0.1 wt % to 10 wt %, preferably from 0.5 wt % to 7.5 wt %, even more preferably from 1.0 wt % to 5.0 wt % of at least one cationic polymer. Cationic polymers are listed above. In at least one embodiment, the cationic polymer is selected from the group consisting of polyquaternium-10, guar hydroxypropyltrimonium chloride, polyquaternium-7, polyquaternium-6, and combinations thereof. Optionally the hair styling composition comprises from 0.5 wt % to 60 wt %, preferably from 1.0 wt % to 50 wt %, even more preferably from 2.0 wt % to 40 wt % of at least one propellant. Propellants are listed above. In at least one embodiment, the propellant is selected from the group consisting of nitrogen, carbon dioxide, pentane, n-butane, iso-butane, propane, and combinations thereof. Optionally the hair styling composition comprises from 0.01 wt % to 5.0 wt %, preferably from 0.1 wt % to 3.0 wt %, even more preferably from 0.4 wt % to 1.0 wt % of at least one preservative or preservation boosting ingredient. Preservatives or preservation boosting ingredients are listed above. In at least one embodiment, the preservative or preservation boosting ingredient is selected from the group consisting of sodium benzoate, methylparaben, phenoxyethanol, methylisothiazolinone, DMDM hydantoin, methylchloroisothiazolinone, pyrithione, octopirox, and combinations thereof. Optionally the hair styling composition comprises from 0.01 wt % to 20 wt %, preferably from 0.1 wt % to 10.0 wt %, even more preferably from 0.5 wt % to 5.0 wt % of at least one further auxiliary. Auxiliaries are listed above. In a preferred embodiment, the hair styling composition has a pH value from 2.0 to 9.0, preferably from 3.0 to 8.0, even more preferably from 4.0 to 7.0.

In at least one embodiment, the composition is a hair coloring/hair bleaching composition. Optionally the hair coloring/hair bleaching composition comprises from 0.5 wt % to 60 wt %, preferably from 1.0 wt % to 50 wt %, even more preferably from 2.0 wt % to 40 wt % of at least one direct dye. Direct dyes are listed above. Optionally the hair coloring/hair bleaching composition comprises from 00.001 wt % to 5.0 wt %, preferably from 0.05 wt % to 3.0 wt %, even more preferably from 0.1 wt % to 1.0 wt % of at least one oxidizing or reducing agent. Oxidizing or reducing agents are listed above. In at least one embodiment, the hair coloring/hair bleaching composition comprises a primary intermediate and a coupling agent. In at least one embodiment, the primary intermediate is selected from the group consisting of 2,4,5,6-tetraaminopyrimidine, 4-aminophenol, 4-amino-3-methylphonol, 2,5-diamino-toluene and 2-(2,5-diaminophenyl) ethanol, 2-methoxymethyl-1,4-benzenediamine, and combinations thereof. In at least one embodiment, the coupling agent is selected from the group consisting of 5-amino-4-chloro-o-cresol, 2,6-diaminopyridine, 2,6-dihydroxyethylaminotoluene, resorcinol, 2-methyl resorcinol, 4-amino-2-methylphenol, and combinations thereof. Optionally the hair coloring/hair bleaching composition comprises from 0.1 wt % to 15 wt %, preferably from 0.5 wt % to 10 wt %, even more preferably from 1.0 wt % to 5.0 wt % of at least one emulsifier, coemulsifier and/or solubilizer. Optionally the hair coloring/hair bleaching composition comprises from 0.001 wt % to 5.0 wt %, preferably from 0.01 wt % to 3.0 wt %, even more preferably from 0.1 wt % to 1.0 wt % of at least one alkalizing or pH adjusting agent. Alkalizing or pH adjusting agents are listed above. Optionally the hair coloring/hair bleaching composition comprises from 0.01 wt % to 20 wt %, preferably from 0.1 wt % to 10.0 wt %, even more preferably from 0.5 wt % to 5.0 wt % of at least one further auxiliary. Auxiliaries are listed above. In a preferred embodiment, the hair coloring/hair bleaching composition has a pH value from 6.0 to 14.0, preferably from 7.0 to 13.0, even more preferably from 8.0 to 12.0.

In at least one embodiment, the cosmetic, dermatological or pharmaceutical composition is for use on mucous membranes. In at least one embodiment, the composition is an emulsion, gel or paste, preferably an oil-in-water (o/w), cream gel or hydrogel composition. In a preferred embodiment, the composition suitable for mucous membranes has a viscosity from 100 000 to 300 000 mPa·s, preferably from 1 000 to 200 000 mPa·s, more preferably from 2 000 to 100 000 mPa·s and very preferably from 5 000 to 30 000 mPa·s (25° C., Brookfield RVT, T-C spindle at 20 revolutions per minute).

In at least one embodiment, the composition is a toothpaste composition. In at least one embodiment, the composition is a mouthwash composition.

In at least one embodiment, the composition is a lubricant composition.

Example Embodiments of the Second Aspect

In a preferred embodiment, the second aspect relates to a cosmetic, dermatological or pharmaceutical composition comprising:
(I) a polymer; and
(II) a cosmetically acceptable component;
  wherein the polymer is crosslinked or non-crosslinked, characterized in that the polymer comprises:
  (a) from 90 mol-% to 99.9 mol-%, preferably from 95 mol-% to 99.5 mol-% of repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

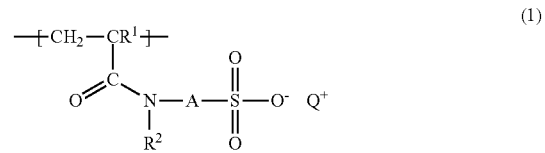

wherein:
  $R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof;
  (b) optionally from 0.01 mol-% to 10 mol-%, preferably from 0.01 mol-% to 5 mol-% of crosslinking or branching units, wherein the crosslinking or branching units result from the incorporation of a monomer comprising at least two olefinically unsaturated double bonds.

In at least one embodiment, the polymer comprises from 96 mol-% to 99.7 mol-%, preferably from 97 mol-% to 99.5 mol-% units (a) and from 0.3 mol-% to 4 mol-%, preferably from 0.5 mol-% to 3 mol-% units (b). In at least one embodiment, the polymer comprises units (a) and (b), such that the sum thereof is at least 99 mol-%, by total weight of the polymer.

In a preferred embodiment, the second aspect relates to a cosmetic, dermatological or pharmaceutical composition comprising:
(I) a polymer; and
(II) a cosmetically acceptable component;
  wherein the polymer is crosslinked or non-crosslinked, characterized in that the polymer comprises:
  (a) from 40 mol-% to 98 mol-%, preferably from 55 mol-% to 98 mol-% repeating units according to Formula (1) wherein at least 10 wt.-%, preferably at least 20 wt.-% of the repeating units comprises from 28 wt.-% to 100 wt.-% bio-based carbon content, relative to the total mass of carbon in the repeating unit according to Formula (1), measured according to standard ASTM D6866-12, Method B;

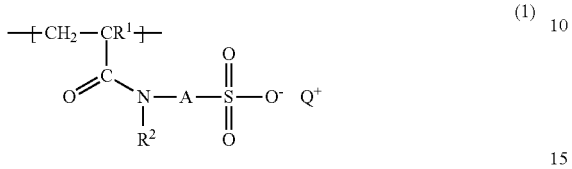

(1)

wherein:

R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof;

(b) optionally from 0.01 mol-% to 5 mol-%, preferably from 0.01 mol-% to 3 mol-% crosslinking or branching units, wherein the crosslinking or branching units result from the incorporation of a monomer comprising at least two olefinically unsaturated double bonds;

(c) optionally from 0.99 mol-% to 59.99 mol-%, preferably from 1.99 mol-% to 44.99 mol-% of repeating neutral structural units wherein at least 10 wt.-%, preferably at least 20 wt.-% of the neutral structural units comprises from 0 wt.-% to 100 wt.-% bio-based carbon content, relative to the total mass of carbon in the repeating unit, measured according to standard ASTM D6866-12, Method B.

In at least one embodiment, the polymer comprises from 45 mol-% to 97 mol-%, preferably from 65 mol-% to 96 mol-% units (a), from 0.25 mol-% to 4 mol-%, preferably from 0.3 mol-% to 3 mol-% units (b), from 2 mol-% to 54.7 mol-%, preferably from 2.5 mol-% to 34.5 mol-% units (c). In at least one embodiment, the polymer comprises units (a), (b) and (c) such that the sum thereof is at least 99 mol-%, by total weight of the polymer.

In at least one embodiment, the polymer comprises from 70 mol-% to 98 mol-%, preferably from 73 mol-% to 96 mol-% units (a), from 0.6 mol-% to 2.5 mol-%, preferably from 0.75 mol-% to 2 mol-% units (b), from 1.4 mol-% to 54.7 mol-%, preferably from 2.5 mol-% to 34.5 mol-% units (c). In at least one embodiment, the polymer comprises units (a), (b) and (c) such that the sum thereof is at least 99 mol-%, by total weight of the polymer.

In a preferred embodiment, the second aspect relates to a cosmetic, dermatological or pharmaceutical composition comprising:

(I) a polymer; and
(II) a cosmetically acceptable component;
wherein the polymer is crosslinked or non-crosslinked, characterized in that the polymer comprises:

(a) from 9.49 mol-% to 98 mol-%, preferably from 27.5 mol-% to 97.4 mol-% repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

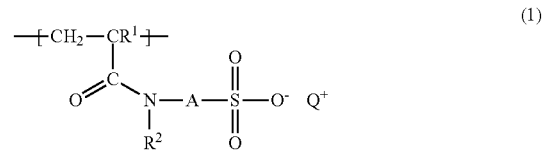

(1)

wherein:

R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof;

(b) optionally from 0.01 mol-% to 5 mol-%, preferably from 0.01 mol-% to 4 mol-% crosslinking or branching units, wherein the crosslinking or branching units result from the incorporation of a monomer comprising at least two olefinically unsaturated double bonds;

(c) optionally from 0.01 mol-% to 88.52 mol-%, preferably from 0.05 mol-% to 72.4 mol-% of repeating neutral structural units, preferably wherein at least 10 wt.-%, preferably at least 20 wt.-% of the repeating neutral structural units comprises from 0 wt.-% to 100 wt.-% bio-based carbon content, relative to the total mass of carbon in the repeating neutral structural unit, measured according to standard ASTM D6866-12, Method B;

(d) optionally from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units are different from units (a) and preferably wherein at least 10 wt.-%, preferably at least 20 wt.-% of the repeating anionic structural units comprise from 0 wt.-% to 100 wt.-% bio-based carbon content, relative to the total mass of carbon in the repeating anionic structural unit, measured according to standard ASTM D6866-12, Method B;
and wherein the polymer has a weight average molecular weight of at least 700 g/mol, preferably from 700 g/mol to 10 million g/mol.

In at least one embodiment, the polymer comprises from 37 mol-% to 96.4 mol-%, preferably from 43 mol-% to 95.3 mol-% units (a), from 0.1 mol-% to 3 mol-%, preferably from 0.2 mol-% to 2 mol-% units (b), from 0.1 mol-% to 59.3 mol-%, preferably from 0.5 mol-% to 52.8 mol-% units (c), and from 3.5 mol-% to 16 mol-%, preferably from 4 mol-% to 14 mol-% units (d). In at least one embodiment, the polymer comprises units (a), (b), (c) and (d) such that the sum thereof is at least 99 mol-%, by total weight of the polymer.

In at least one embodiment, the polymer comprises from 70 mol-% to 94.5 mol-%, units (a), from 0.35 mol-% to 1.5 mol-%, units (b), from 0.65 mol-% to 25.65 mol-% units (c), and from 4.5 mol-% to 12 mol-% units (d). In at least one embodiment, the polymer comprises units (a), (b), (c) and (d) such that the sum thereof is at least 99 mol-%, by total weight of the polymer.

In a preferred embodiment, the second aspect relates to a cosmetic, dermatological or pharmaceutical composition comprising:
(I) a polymer; and
(II) a cosmetically acceptable component;
wherein the polymer is crosslinked or non-crosslinked, characterized in that the polymer consists of:
(a) from 9.49 mol-% to 98 mol-%, preferably from 27.5 mol-% to 97.4 mol-% repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

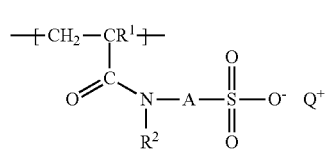

(1)

wherein:
R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof;
(b) optionally from 0.01 mol-% to 5 mol-%, preferably from 0.01 mol-% to 4 mol-% crosslinking or branching units, wherein the crosslinking or branching units result from the incorporation of a monomer comprising at least two olefinically unsaturated double bonds;
(c) optionally from 0.01 mol-% to 88.52 mol-%, preferably from 0.05 mol-% to 72.4 mol-% of repeating neutral structural units, preferably wherein at least 10 wt.-%, preferably at least 20 wt.-% of the repeating neutral structural units comprises from 0 wt.-% to 100 wt.-% bio-based carbon content, relative to the total mass of carbon in the repeating neutral structural unit, measured according to standard ASTM D6866-12, Method B;
(d) optionally from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units are different from units (a) and preferably wherein at least 10 wt.-%, preferably at least 20 wt.-% of the repeating anionic structural units comprise from 0 wt.-% to 100 wt.-% bio-based carbon content, relative to the total mass of carbon in the repeating anionic structural unit, measured according to standard ASTM D6866-12, Method B;
(e) optionally at least one optional unit.

Third Aspect

A third aspect of the invention relates to a process of formulating a cosmetic, dermatological or pharmaceutical composition comprising incorporating a polymer into the composition, wherein the polymer is crosslinked or non-crosslinked, characterized in that the polymer comprises at least 9.49 mol-% of repeating units (a) according to Formula (1) wherein at least 10 wt.-%, preferably at least 20 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method B;

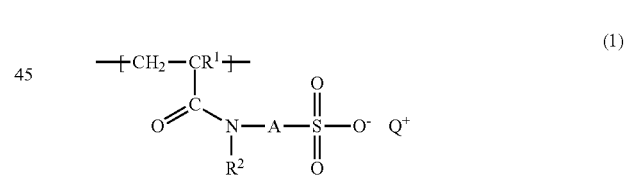

(1)

wherein:
R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof.

In at least one embodiment of the third aspect, the cosmetic, dermatological or pharmaceutical composition is according to the second aspect.

In at least one embodiment of the third aspect, the composition comprises a cosmetically acceptable component. In at least one embodiment, the polymer is mixed with the cosmetically acceptable component. In at least one embodiment, the composition comprises a plurality of cosmetically acceptable components.

Suitable cosmetically acceptable components are mentioned in the second aspect—such cosmetically acceptable components are compatible and combinable with the third aspect. In at least one embodiment, the cosmetically acceptable component is selected from the group consisting of surfactants, auxiliaries, hair conditioning agents, hairstyling polymers, and combinations thereof. Surfactants, auxiliaries, hair conditioning agents and hairstyling polymers are disclosed in the second aspect—such cosmetically acceptable components are compatible and combinable with the third aspect.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

In at least one embodiment, the composition comprises at least 0.1 wt.-%, or at least 0.2 wt.-%, or at least 0.3 wt.-%, or at least 0.4 wt.-%, or at least 0.5 wt.-%, or at least 0.6 wt.-%, or at least 0.7 wt.-%, or at least 0.8 wt.-%, or at least 0.9 wt.-%, or at least 1.0 wt.-%, or at least 1.1 wt.-%, or at least 1.2 wt.-%, or at least 1.3 wt.-%, or at least 1.4 wt.-%, or at least 1.5 wt.-%, or at least 1.6 wt.-%, or at least 1.5 wt.-%, or at least 1.6 wt.-%, or at least 1.7 wt.-%, or at least 1.8 wt.-%, or at least 1.9 wt.-%, or at least 2.0 wt.-% of the polymer.

In at least one embodiment, the polymer is a crosslinked or non-crosslinked homopolymer. In at least one embodiment, the polymer is a crosslinked or non-crosslinked copolymer. Preferably the polymer is crosslinked.

In at least one embodiment, the polymer has a weight average molecular weight of at least 700 g/mol, preferably from 700 g/mol to 10 million g/mol.

In at least one embodiment, the polymer is obtained by polymerising at least one compound according to Formula (3), wherein the compound comprises from 28 wt.-% to 100 wt.-%, preferably from 40 wt.-% to 100 wt.-%, bio-based carbon content, relative to the total mass of carbon in the compound, measured according to standard ASTM D6866-12, Method B;

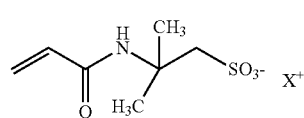

and wherein $X^+$ is a proton. In at least one embodiment, the compound is neutralised with a base prior to polymerisation.

In at least one embodiment, the polymer has been neutralized following polymerization using a base. In at least one embodiment, the repeating units according to Formula (1) have a degree of neutralisation of between 0 mol-% and 100 mol-%. In at least one embodiment, the repeating units according to Formula (1) have a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80 mol-%, more preferably more than 90 mol-%, even more preferably more than 95 mol-%.

In at least one embodiment, the polymer is substantially free of units not being those according to Formula (1), wherein $R^1$ and $R^2$ are H; A is —C(CH$_3$)$_2$—H$_2$C; and $Q^+$ is a cation. In at least one embodiment, the polymer is a homopolymer.

In at least one embodiment, the polymer is a copolymer of units according to those according to Formula (1), wherein $R^1$ and $R^2$ are H; A is —C(CH$_3$)$_2$—H$_2$C; and $Q^+$ is a cation, and at least one further unit.

In at least one embodiment, the polymer is a rheology modifier or a thickening agent, or is suitable for use therefor.

Fourth Aspect

A fourth aspect relates to a method for treating keratinous material, comprising applying the composition according to the second aspect to the keratinous material. In at least one embodiment of the fourth aspect, the composition is a cosmetic composition.

In at least one embodiment, the keratinous material is keratin fibres. In at least one embodiment, the keratinous material is selected from human skin and/or human hair.

In at least one embodiment of the fourth aspect, the composition comprises a cosmetically acceptable component. In at least one embodiment, the composition comprises a plurality of cosmetically acceptable components.

Suitable cosmetically acceptable components are mentioned in the second aspect—cosmetically acceptable components are compatible and combinable with the fourth aspect. In at least one embodiment, the cosmetically acceptable component is selected from the group consisting of surfactants, auxiliaries, hair conditioning agents, hairstyling polymers, and combinations thereof. Surfactants, auxiliaries, hair conditioning agents and hairstyling polymers are disclosed in the second aspect—such cosmetically acceptable components are compatible and combinable with the fourth aspect.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

In at least one embodiment, the composition comprises at least 0.1 wt.-%, or at least 0.2 wt.-%, or at least 0.3 wt.-%, or at least 0.4 wt.-%, or at least 0.5 wt.-%, or at least 0.6 wt.-%, or at least 0.7 wt.-%, or at least 0.8 wt.-%, or at least 0.9 wt.-%, or at least 1.0 wt.-%, or at least 1.1 wt.-%, or at least 1.2 wt.-%, or at least 1.3 wt.-%, or at least 1.4 wt.-%, or at least 1.5 wt.-%, or at least 1.6 wt.-%, or at least 1.5 wt.-%, or at least 1.6 wt.-%, or at least 1.7 wt.-%, or at least 1.8 wt.-%, or at least 1.9 wt.-%, or at least 2.0 wt.-% of the polymer.

In at least one embodiment, the polymer is a crosslinked or non-crosslinked homopolymer. In at least one embodiment, the polymer is a crosslinked or non-crosslinked copolymer.

In at least one embodiment, the polymer has a weight average molecular weight of at least 700 g/mol, preferably from 700 g/mol to 10 million g/mol.

Fifth Aspect

A fifth aspect relates to a product comprising the composition according to the second aspect. In at least one embodiment, the product comprises a receptacle comprising the composition according to the second aspect. In at least one embodiment, the product comprises an opening for dispensing the composition. In at least one embodiment, the opening is equipped with a closure. In at least one embodiment, the receptacle comprises plastics.

Monomer

International patent application PCT/EP2017/064977 (claiming priority from European patent application 16175218.3 filed on 20 Jun. 2016) in the name of Clariant International Ltd, the disclosure of which is incorporated herein by reference, discloses the synthesis of bio-based acryloyldimethyltaurate, which can be used as a monomer for the polymer according to the present invention.

Isobutene Samples Used:

The composition of petroleum-based isobutene is different from bio-based isobutene. Bio-based isobutene contains exclusively contemporary carbon and hence has a different distribution of carbon isotopes as compared to fossil, petrochemical-based carbon. Fossil carbon was cut off from the natural carbon equilibrium for millions of years and all the natural $^{14}C$ has already degraded, and hence the concentration of $^{14}C$ is zero in fossil carbon sources. Contemporary carbon, produced by living organisms is part of the atmospheric carbon isotope equilibrium. $^{14}C$ or radiocarbon is constantly being created in the atmosphere by the interaction of cosmic rays with atmospheric nitrogen. The resulting radiocarbon combines with atmospheric oxygen to form radioactive carbon dioxide, which is incorporated into plants by photosynthesis; animals then acquire $^{14}C$ by eating the plants. When the animal or plant dies, it stops exchanging carbon with its environment, and from that point onwards the amount of $^{14}C$ it contains begins to decrease as the $^{14}C$ undergoes radioactive decay. Therefore, in contemporary carbon the concentration of $^{14}C$ is in the order of 10-10%. Masao Kunioka recently described "Measurement Methods of Biobased Carbon Content for Biomass-based Chemicals and Plastics" in *Radioisotopes*, 62, 901-925 (2013).

Interestingly enough, also the chemical composition of bio-based and petrochemical-based isobutene is different in several aspects. Table 1 shows differences in the composition for the isobutene samples used in the present invention. Petrochemical-based isobutene contains small amounts of petrochemical by-products such as propane, propene, butane and isobutane, but it does not contain any traces of metabolic products (Type Petro, IB1). In contrast to the petrochemical isobutene, the bio-based samples contain carbon dioxide and small quantities of ethanol as metabolic products from the microorganisms (Type Bio, samples IB2 to IB5). The bio-based isobutene samples do not contain any propane, propene, butane or isobutane.

TABLE 1

| Isobutene-sample units | type | Isobutene m/v % | $N_2$ m/v % | $CO_2$ m/v % | $H_2O$ m/v % | ethanol m/v % | propane m/v % | Propene m/v % | Isobutane m/v % | n-butane m/v % |
|---|---|---|---|---|---|---|---|---|---|---|
| IB1 | Petro | 99.873 | ND | ND | 0.06 | ND | 0.0003 | 0.0018 | 0.0639 | 0.001 |
| IB2 | Bio | 99.72 | 0.1 | 0.3 | 0.03 | 0.002 | ND | ND | ND | ND |
| IB3 | Bio | 92.07 | 3.2 | 4.7 | 0.03 | 0.005 | ND | ND | ND | ND |
| IB4 | Bio | 21.94 | 60 | 18 | 0.05 | 0.008 | ND | ND | ND | ND |
| IB5 | Bio | 97.7 | 2 | 0.26 | 0.03 | 0.002 | ND | ND | ND | ND |

KEY: ND = not detected.

Sixth Aspect

A sixth aspect relates to kit comprising the product of the fifth aspect and a further product or implement.

EXAMPLES

The examples which follow are intended to illustrate the subject matter of the invention, without restricting it thereto.

Compared with the quality of petrochemically acquired isobutene, the amount of impurities in the bio-based isobutene are significantly higher and the composition is different. Especially IB4 contains only 21.94% isobutene and 18% carbon dioxide. Surprisingly it was found that it was possible to synthesize ACDMT with high purity based on the isobutene with high levels of impurities.

TABLE 2

Acrylonitrile sample qualities used

| Acrylonitrile sample Units | Type | Acrylonitrile | $H_2O$ as is | $H_2O$ after drying | 4-methoxy-phenol Ppm |
|---|---|---|---|---|---|
| AN1 | Petro | 99.2 | 0.41 | 19 | 43 |
| AN2 | Bio | 99.1 | 0.53 | 21 | 56 |

Acrylonitrile ≥99%, from Sigma-Aldrich contains 35-45 ppm monomethyl ether hydroquinone as inhibitor, contained 0.41% water before drying. It was dried by adding 50 g molecular sieve 0.4 nm from Merck Millipore, Merck KGaA. The residual water content of the acrylonitrile was 19 ppm, measured by Karl-Fischer titration (DIN 51777). The biologically acquired acrylonitrile was relatively similar in chemical composition as compared to the petrochemical one. The used acrylonitrile was obtained in two steps via oxidative decarboxylation of glutamic acid and subsequent decarbonylation elimination of 3-cyanopropionic acid to form acrylonitrile using the method described in *Green Chemistry*, 2011, 13, 807.

Monomer Comparative Example 1 (MCompEx1),
Using Conventional Petrochemical Raw Materials
in a Batch Process The reactor was a 5 neck 250 ml round bottom flask, equipped with an overhead agitator, thermocouple, sub surface gas injection pipe, intensive condenser and dropping funnel with pressure compensation. The head of the condenser was equipped with a dry tube containing 50 g of 4 Angstrom molecular sieve. A PTFE plate stirrer with precision glass joint seal was connected to the overhead stirrer. 150 ml dry acrylonitrile was dosed to the reactor. Under stirring at 150 rpm the acrylonitrile was cooled with a bath consisting of a mixture of 300 g ice and 100 g NaCl. As soon as the reactor temperature reaches −10° C., 39.30 g of 100% sulfuric acid was slowly dosed. The temperature was kept in a range of −10° C. to −7.5° C. The time for dosing the sulfuric acid was 40 minutes. The liquid stayed clear.

Then the ice bath was removed and replaced by a water bath at 21° C. Subsequently 9.9 L of isobutene was dosed at a rate of 10 L/h. The temperature was allowed to climb quickly, but controlled to be stable at 40° C. for the course of the dosage. After approximately 35 min., fine white crystals started to precipitate. After dosage was completed the reaction mixture was stirred for one hour at 40° C. Then the reaction mixture was cooled under agitation for 30 min to 20° C. The reaction mixture was a fine white suspension. The solid was separated by vacuum filtration over glass fiber filter, stirred with 50 g fresh acrylonitrile in a 250 ml Erlenmeyer-flask for 10 minutes using a magnetic stirrer, PTFE coated stirrer bar and covered with a glass lid. The solids of the suspension was removed again by vacuum filtration over a glass fiber filter (Whatman Grade GF/D). The solid was dried for 4 hours in a laboratory rotation evaporator at a bath temperature of 60° C., starting at a pressure of 300 mbar. After 30 minutes the pressure was ramped down to 10 mbar in 3 h.

With a yield of 85 wt.-% ACDMT was isolated with a purity of 95.9 wt.-%. And 0.3 wt.-% acrylonitrile, 0.6 wt.-% acrylamide, 2.9 wt.-% tert. butylacrylamide and 0.3 wt.-% 2-methylprop-2-en-1-sulfonic acid were detected.

The Monomer Comparative Examples MCompEx2 to MCompEx3 were carried out in the same way, but the sulfur trioxide excess was increased. Please see Table 3.

Monomer Comparative Example 4 (MCompEx4)
(See US2010/0274048, which is Incorporated
Herein by Reference) for a Continuous Process
with Conventional Petrochemical Raw Materials Two glass reactors each provided with a stirrer, an inlet pipe and an outlet pipe were connected to each other. Acrylonitrile and sulfuric acid were fed by peristaltic pumps into the first reactor. With a flow rate of 47.1 g/h sulfuric acid and 22.36 g/h 20% commercial fuming sulfuric acid and 161.1 g/h dry acrylonitrile was pumped. The sulfuric acid was 97% concentrated. The concentration of sulfur trioxide in fuming sulfuric acid was chosen to compensate for the water carried by the raw materials acrylonitrile and isobutene. The temperature of the reaction mixture in the first reactor was kept at −10±2.5° C. The average residence time was 90 minutes. Sulfonic acid and acrylonitrile were mixed and the mixed fluid thereof was fed into the second reactor. The second reactor was a three neck 250 ml round bottom reactor, modified with a side neck to allow overflow of the reactor to a beaker. It was connected with an overhead stirrer, glass stirrer with PTFE stirrer blades and an intensive condenser. In the second reactor, isobutylene gas (IB1) was blown sub surface with a flow rate of 30.8 g/h into the mixed fluid to synthesize ACDMT. The reaction (synthesis) was conducted continuously with an average residence time of 90 minutes at a temperature of 40±2.5° C. After 11 h continuously conducted reaction a sample of the reaction mixture was taken and analyzed.

The ACDMT slurry obtained in the above production was suction-filtered using a glass filter to obtain a cake on the glass filter. Acrylonitrile of an amount (mass) shown in Table 5, relative to the mass of the cake was poured onto the cake. Suction filtering was conducted again to wash the cake with acrylonitrile.

The washed cake was dried for 360 minutes at a temperature of 80° C. with a rotational evaporator at reduced pressure. A vacuum of 400 mbar was applied for 30 minutes. Then the pressure was ramped down to 10 mbar in 2 hours and maintained at 10 mbar until drying was completed.

The yield determined was related to the sample size drawn. The ACDMT powder obtained was analyzed by HPLC to measure the concentrations of acrylonitrile (abbreviated as AN), acrylamide (abbreviated as AM), tert.-butylacrylamide (abbreviated as tBAM), 2-methyl-2-propenyl-1-sulfonic acid (abbreviated as IBSA). The results of the comparative experiment is shown in Table 6.

Monomer Example 1

The reactor was a 5 neck 250 ml round bottom flask, equipped with an overhead agitator, thermocouple, subsurface gas injection pipe, intensive condenser and dropping funnel with pressure compensation. The head of the condenser was equipped with a dry tube containing 50 g of 4 Angstrom molecular sieve. A PTFE plate stirrer with precision glass joint seal was connected to the overhead stirrer. 150 ml dry acrylonitrile was dosed to the reactor. Under stirring at 150 rpm the acrylonitrile was cooled with a bath consisting of a mixture of 300 g ice and 100 g NaCl. Alternatively the mixture could be cooled down with a combination of acetone and dry ice. As soon as the reactor temperature reaches −10° C., 49.30 g 100% sulfuric acid was slowly dosed. The access of sulfur trioxide was controlled to compensate for the water content of the raw materials isobutene and acrylonitrile. The variation of the process conditions are documented in Table 3.

The temperature was kept in a range of −10° C. to −7.5° C. The time for dosing the sulfuric acid was 40 minutes. The liquid stays clear.

Then the ice bath was removed and replaced by a water bath at 21° C. 9.9 L of bio-based isobutene was dosed at a rate of 10 L/h. The temperature was kept allowed to climb quickly, but controlled to stay at 40° C. for the course of the dosage. After approximately 25 min., fine white crystals started to precipitate. After dosage was completed the reaction mixture was stirred for one hour at 40° C. Then the reaction mixture was cooled under agitation for 30 min. to 20° C. The reaction mixture was a fine white suspension. The solid was separated by vacuum filtration over glass fiber filter, stirred with 50 g fresh acrylonitrile in a 250 ml Erlenmeyer-flask for 10 minutes using a magnetic stirrer, PTFE coated stirrer bar and covered with a glass lid. The solids of the suspension was removed again by vacuum filtration over a glass fiber filter (Whatman Grade GF/D). The solid was dried for 4 hours in a laboratory rotation evaporator at a bath temperature of 80° C., starting at a pressure of 300 mbar, after 30 minutes the pressure was ramped down to 10 mbar in 3 h.

bio-based ACDMT. Surprisingly, the purity of the bio-based ACDMT is higher as compared to the monomer comparative experiments 1 to 3. In particular the impurities t-BAM and IBSA were reduced. The potential side products IBSA and IBDSA act to moderate (control) the molecular weight in the radical polymerization. Hence a person skilled in the art would expect the molecular weight of a polymer in the presence of a larger amount of a moderator to be lower as compared to one polymerized under the same conditions with a lesser amount of moderator. As an IBDSA standard was not available the amount of IBDSA was not quantified.

A surprising advantage of the invention is that bio-based isobutene can be used in the ACDMT production process with a lower quality as compared to petrochemically-manufactured isobutene to produce an as good or better quality of ACDMT.

To test the bio-based content, three samples were investigated according to ASTM D6866-12, Method B. MCompEx1 was made with conventional, petrochemical raw materials. Therefore it is to be expected that all carbon is fossil carbon. Consequently no $^{14}C$ should be found and the bio-based carbon content should be zero. In this experiment, the investigation indeed returned a bio-based carbon content

TABLE 3

Reaction conditions for batch reactions

| Experiment Unit | AN [g] | Material | $H_2SO_4$, 100% [g] | Oleum 20% $SO_3$ [g] | Isobutene [g] | Material | Flow rate [L/h] | T1 [° C.] | T2 [° C.] |
|---|---|---|---|---|---|---|---|---|---|
| MCompEx1 | 150 | AN1 | 49.3 | 0.0 | 28.1 | IB1 | 10 | −10 | 40 |
| MCompEx2 | 150 | AN1 | 49.1 | 0.10 | 28.1 | IB1 | 10 | −10 | 40 |
| MCompEx3 | 150 | AN1 | 48.9 | 0.2 | 28.1 | IB1 | 10 | −10 | 40 |
| M1 | 150 | AN1 | 49.2 | 0.08 | 28.1 | IB2 | 10 | −10 | 40 |
| M2 | 150 | AN1 | 49.2 | 0.09 | 30.5 | IB3 | 11 | −10 | 40 |
| M3 | 150 | AN1 | 48.6 | 0.56 | 128 | IB4 | 23 | −10 | 40 |
| M4 | 150 | AN1 | 49.2 | 0.08 | 28.8 | IB5 | 10 | −10 | 40 |
| M5 | 50 | AN2 | 16.4 | 0.03 | 9.6 | IB5 | 10 | −10 | 40 |

The results of the comparative experiments and the experiments describing the invention are summarized in Table 4.

The experiments demonstrate that the precipitation of ACDMT starts earlier with the bio-based isobutene as compared to the petro-chemical produced isobutene. Also it was found that the use of bio-based isobutene was suitable make of 0 wt.-%. In Experiment 1, a sample of bio-based isobutene (IB2) was used. As four of the seven ACDMT carbon atoms were replaced by bio-based carbon, in theory 57 wt.-% bio-based carbon should be found. The experiment delivers a bio-based carbon content of 55 wt.-%. The deviation of the theoretical value can be explained by the impurity of the material and the analytical error of 2% of the method.

TABLE 4

Results of the examples using the batch process

| Experiment | Yield [g] | Yield [%] | ACDMT [wt.-%] | AM [wt.-%] | AN [wt.-%] | t-BAM [wt.-%] | IBSA [wt.-%] | Bio-based content [wt.-%] |
|---|---|---|---|---|---|---|---|---|
| MCompEx1 | 91.1 | 88 | 95.9 | 0.6 | 0.3 | 2.9 | 0.3 | 0 |
| MCompEx2 | 93.5 | 90 | 97.1 | 0.3 | 0.3 | 2.1 | 0.2 | ND |
| MCompEx3 | 91.6 | 88.5 | 96.2 | 0.3 | 0.3 | 1.9 | 0.4 | ND |
| M1 | 98.4 | 95 | 99.4 | 0.07 | 0.06 | 0.45 | 0.05 | 55 |
| M2 | 98.2 | 95 | 98.9 | 0.08 | 0.09 | 0.51 | 0.03 | ND |
| M3 | 97.3 | 94 | 98.2 | 0.1 | 0.09 | 0.49 | 0.06 | 56 |
| M4 | 98.3 | 95 | 99.5 | 0.05 | 0.04 | 0.39 | 0.02 | ND |
| M5 | 33.0 | 95.5 | 99.2 | 0.04 | 0.04 | 0.41 | 0.03 | 99 |

KEY: ND = not detected; ACDMT = acryloyldimethyltaurate; AM = acrylamide; AN = acrylonitrile; tBAM = tert.-butyl acrylamide; IBSA = isobutene sulfonic acid.

The use of bio-based isobutene achieve high yields of ACDMT as well as high purities of ACDMT. Indeed, the use of bio-isobutene leads to a purer ACDMT as compared to petrochemical ACDMT.

Polymer

Polymerization experiments show especially that ACDMT samples with lower content of IBSA lead to higher molecular weight polymers as compared to ACDMT samples with higher IBSA content.

Polymerization Process A1: General Precipitation Polymerization Procedure in Tert.-Butanol Dose in a 1-Liter Quickfit round bottom flask equipped with a refux condenser, sub surface gas inlet tubing, inner temperature sensor and overhead agitator 400 g tert.-butanol with a water content of 2.5 wt.-%. Charge 100 g bio-based ACDMT. Neutralize the ACDMT to a pH of 7 to 8 by injection of gaseous ammonia above the surface. Keep the temperature below 40° C. Dose a 1.45 g TMPTA as a crosslinker according to Polymer Table A1. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.3 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymerization Process B1: General Precipitation Polymerization Procedure in Tert.-Butanol/Dimethylketone Mixture Dose in a 1-Liter Quickfit round bottom flask equipped with a refux condenser, sub surface gas inlet tubing, inner temperature sensor and overhead agitator 200 g tert.-butanol and 200 g dimethylketon with a water content of 3 wt.-%. Charge 100 g bio-based ACDMT. Neutralize the ACDMT by charging 40.5 g sodium hydrogen carbonate. Keep the temperature below 40° C. Dose 1.45 g TMPTA, as a crosslinker and according to Polymer Table B1. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.3 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymer Table A1):
Polymers according to polymerization process A1:

| Polymer example name | ACDMT in g | ACDMT in mol-% | Crosslinker Name | g | mol-% | Initiator Name | g |
|---|---|---|---|---|---|---|---|
| A1/1 | 100.0 | 99.0 | TMPTA | 1.45 | 1.00 | DLP | 1.30 |
| A1/2 | 100.0 | 98.7 | TMPTA | 1.81 | 1.25 | DLP | 2.00 |
| A1/3 | 100.0 | 99.0 | TMPTA | 2.17 | 1.50 | DLP | 1.30 |
| A1/4 | 100.0 | 97.1 | TMPMTA | 4.50 | 2.94 | V-601 | 1.10 |
| A1/5 | 100.0 | 98.5 | TMPMTA | 2.30 | 1.52 | V-601 | 1.10 |
| A1/6 | 100.0 | 98.0 | TMPMTA | 3.05 | 2.01 | V-601 | 1.10 |
| A1/7 | 100.0 | 99.0 | PEG 600 DMA | 2.80 | 1.01 | V-601 | 1.10 |
| A1/8 | 100.0 | 98.5 | PEG 600 DMA | 4.25 | 1.52 | DLP | 2.00 |
| A1/9 | 100.0 | 98.8 | PEG 600 DMA | 3.48 | 1.25 | DLP | 2.00 |
| A1/10 | 100.0 | 97.0 | GPTA | 6.30 | 2.96 | V-601 | 1.10 |
| A1/11 | 100.0 | 98.0 | GPTA | 4.20 | 1.99 | V-601 | 1.10 |
| A1/12 | 100.0 | 98.8 | GPTA | 2.60 | 1.24 | V-601 | 1.10 |
| A1/13 | 100.0 | 99.0 | PEAS | 2.50 | 1.00 | V-601 | 1.10 |
| A1/14 | 100.0 | 98.5 | PEAS | 3.80 | 1.52 | V-601 | 1.10 |
| A1/15 | 100.0 | 98.8 | PEAS | 3.10 | 1.24 | V-601 | 1.10 |

ACDMT = acryloyldimethyltaurate, NVP = N-vinylpyrollidone, DMAAm = dimethylacrylamide, TMPTA = trimethylolpropantriacrylate, TMPTA = trimethylolpropantriacrylate, TMPTMA = trimethylolpropantrimethacrylate, GPTA = glycerinpropoxylate triacrylate, PEAS = pentaerythritoldiacrylate monostearate, DLP = dilauryl peroxide, V-601 = dimethyl-2,2'-azobis(2-methylpropionate), PEG 600 DMA = polyethylene glycol dimethacrylate (600 g/mol).

Polymer Table B1):
Polymers according to polymerization process B1:

| Polymer example name | ACDMT g | mol-% | Neutralization reagent Name | /g | Crosslinker Name | g | mol-% | Initiator Name | g |
|---|---|---|---|---|---|---|---|---|---|
| B1/1 | 100.0 | 99.0 | NaHCO$_3$ | 40.5 | TMPTA | 1.45 | 1.00 | DLP | 1.30 |
| B1/2 | 100.0 | 98.7 | NaHCO$_3$ | 40.5 | TMPTA | 1.81 | 1.25 | DLP | 2.00 |
| B1/3 | 100.0 | 98.5 | NaHCO$_3$ | 40.5 | TMPTA | 2.17 | 1.50 | DLP | 2.00 |
| B1/4 | 100.0 | 97.0 | KHCO$_3$ | 48 | TMPTA | 4.35 | 2.95 | V-601 | 1.10 |
| B1/5 | 100.0 | 97.0 | LiHCO$_3$ | 32.6 | TMPTA | 2.17 | 1.50 | V-601 | 1.10 |
| B1/6 | 100.0 | 99.0 | NaHCO$_3$ | 40.5 | TMPMTA | 1.50 | 1.00 | V-601 | 1.10 |
| B1/7 | 100.0 | 98.7 | NaHCO$_3$ | 40.5 | TMPMTA | 1.89 | 1.25 | V-601 | 1.10 |

Polymer Table B1):
Polymers according to polymerization process B1:

| Polymer example name | ACDMT g | ACDMT mol-% | Neutralization reagent Name | Neutralization reagent /g | Crosslinker Name | Crosslinker g | Crosslinker mol-% | Initiator Name | Initiator g |
|---|---|---|---|---|---|---|---|---|---|
| B1/8 | 100.0 | 98.5 | NaHCO₃ | 40.5 | TMPMTA | 2.30 | 1.52 | DLP | 2.00 |
| B1/9 | 100.0 | 98.5 | KHCO₃ | 48 | TMPMTA | 2.30 | 1.52 | DLP | 2.00 |
| B1/10 | 100.0 | 98.5 | LiHCO₃ | 32.6 | TMPMTA | 2.30 | 1.52 | DLP | 2.00 |
| B1/11 | 100.0 | 97.0 | LiHCO₃ | 32.6 | PEG 600 DMA | 8.50 | 3.00 | DLP | 2.00 |
| B1/12 | 100.0 | 98.0 | NaHCO₃ | 40.5 | PEG 600 DMA | 5.60 | 2.00 | DLP | 2.00 |
| B1/13 | 100.0 | 98.8 | NaHCO₃ | 40.5 | PEG 600 DMA | 3.48 | 1.25 | DLP | 2.00 |
| B1/14 | 100.0 | 98.8 | NaHCO₃ | 40.5 | PEG 600 DMA | 3.48 | 1.25 | DLP | 2.00 |
| B1/15 | 100.0 | 98.8 | NaHCO₃ | 40.5 | GPTA | 2.60 | 1.24 | V-601 | 1.10 |
| B1/16 | 100.0 | 99.0 | Na₂CO₃ | 25.5 | GPTA | 2.06 | 0.99 | DLP | 2.00 |
| B1/17 | 100.0 | 98.5 | NaHCO₃ | 40.5 | GPTA | 3.15 | 1.50 | V-601 | 1.10 |
| B1/18 | 100.0 | 98.8 | Na₂CO₃ | 25.5 | GPTA | 2.60 | 1.24 | V-601 | 1.10 |
| B1/19 | 100.0 | 97.0 | NaHCO₃ | 40.5 | PEAS | 7.60 | 2.99 | V-601 | 1.10 |
| B1/20 | 100.0 | 98.5 | NaHCO₃ | 40.5 | PEAS | 3.75 | 1.50 | V-601 | 1.10 |

ACDMT = acryloyldimethyltaurate, NVP = N-vinylpyrollidone, DMAAm = dimethylacrylamide, TMPTA = trimethylolpropane triacrylate, TMPTA = trimethylolpropane triacrylate, TMPTMA = trimethylolpropane trimethacrylate, GPTA = glycerinpropoxylattriacrylate, PEAS = pentaerythritoldiacrylate monostearate, DLP = dilaurylperoxide, V-601 = dimethyl 2,2'-azobis(2-methylpropionate), PEG 600 DMA = polyethylene glycol dimethacrylate (600 g/mol).

Polymerization Process A2: General Precipitation Polymerization Procedure in Tert.-Butanol Dose in a 1-Liter Quickfit round bottom flask equipped with a refux condenser, sub surface gas inlet tubing, inner temperature sensor and overhead agitator 400 g tert.-butanol with a water content of 2.5 wt.-%. Charge 80 g bio-based ACDMT. Neutralize the ACDMT to a pH of 7 to 8 by injection of gaseous ammonia above the surface. Keep the temperature below 40° C. Dose a 0.63 g TMPTA as a crosslinker and 4.3 g NVP as a neutral monomer according to Polymer Table A2. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymerization Process B2: General Precipitation Polymerization Procedure in Tert.-Butanol/Dimethylketone Mixture Dose in a 1-Liter Quickfit round bottom flask equipped with a refux condenser, sub surface gas inlet tubing, inner temperature sensor and overhead agitator 200 g tert.-butanol and 200 g dimethylketone with a water content of 3 wt.-%. Charge 80 g bio-based ACDMT. Neutralize the ACDMT by charging 32.8 g sodium hydrogen carbonate. Keep the temperature below 40° C. Dose 1.27 g TMPTA, as a crosslinker and a 0.44 g methyl acrylate as a neutral monomer according to Polymer Table B2. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymer Table A2):
Polymers according to polymerization process A2:

| Polymer example name | ACDMT /g | ACDMT /mol-% | Neutral Monomer Name | Neutral Monomer /g | Neutral Monomer /mol-% | Crosslinker Name | Crosslinker g | Crosslinker mol-% | Initiator Name | Initiator g |
|---|---|---|---|---|---|---|---|---|---|---|
| A2/1 | 80.0 | 90.4 | NVP | 4.3 | 9.1 | TMPTA | 0.63 | 0.50 | DLP | 1.0 |
| A2/2 | 80.0 | 89.8 | NVP | 4.3 | 9.0 | TMPTA | 1.59 | 1.25 | V-601 | 1.1 |
| A2/3 | 80.0 | 89.1 | NVP | 4.3 | 8.9 | TMPTA | 2.57 | 2.00 | DLP | 1.0 |
| A2/4 | 80.0 | 89.7 | NVP | 4.3 | 9.0 | TMPMTA | 1.66 | 1.25 | V-601 | 1.1 |
| A2/5 | 80.0 | 89.7 | NVP | 4.3 | 9.0 | PEAS | 2.75 | 1.25 | V-601 | 1.1 |
| A2/6 | 80.0 | 93.7 | NVP | 2.3 | 5.0 | GPTA | 2.21 | 1.25 | V-601 | 1.1 |
| A2/7 | 80.0 | 96.0 | NVP | 1.1 | 2.5 | PEAS | 3.07 | 1.50 | V-601 | 1.1 |
| A2/8 | 80.0 | 91.0 | NVP | 3.55 | 7.5 | PEAS | 3.26 | 1.50 | V-601 | 1.1 |
| A2/9 | 70.0 | 82.3 | NVP | 6.85 | 15.0 | PEG 600 DMA | 6.20 | 2.65 | DLP | 1.0 |
| A2/10 | 80.0 | 89.8 | NVP | 4.3 | 9.0 | GPTA | 2.30 | 1.25 | V-601 | 1.1 |
| A2/11 | 80.0 | 97.0 | DMAAm | 1.0 | 2.5 | GPTA | 0.85 | 0.50 | V-601 | 1.0 |
| A2/12 | 80.0 | 94.0 | DMAAm | 2.1 | 5.0 | GPTA | 1.75 | 1.00 | V-601 | 1.0 |
| A2/13 | 80.0 | 74.0 | DMAAm | 12.9 | 25.0 | TMPTA | 1.55 | 1.00 | V-601 | 1.20 |
| A2/14 | 80.0 | 74.0 | DMAAm | 12.9 | 25.0 | PEG 600 DMA | 2.98 | 1.00 | V-601 | 1.20 |

Polymer Table A2): Polymers according to polymerization process A2:

| Polymer example name | ACDMT /g | /mol-% | Neutral Monomer Name | /g | /mol-% | Crosslinker Name | g | mol-% | Initiator Name | g |
|---|---|---|---|---|---|---|---|---|---|---|
| A2/15 | 81.5 | 89.0 | N-isopropylacrylamide | 5.0 | 10.0 | TMPMTA | 1.36 | 1.00 | V-601 | 1.00 |
| A2/16 | 80.0 | 95.8 | Behenylpolyethoxy-(25)-methacrylate | 21.0 | 3.5 | TMPTA | 0.90 | 0.75 | DLP | 1.75 |
| A2/17 | 80.0 | 95.3 | Behenylpolyethoxy-(25)-methacrylate | 21.0 | 3.5 | TMPTA | 1.50 | 1.25 | DLP | 1.75 |
| A2/18 | 80.0 | 96.3 | Behenylpolyethoxy-(25)-methacrylate | 18.0 | 3.0 | PEG$_{600}$ DMA | 1.60 | 0.70 | DLP | 1.75 |
| A2/19 | 80.0 | 91.5 | Laurylpoly-ethoxy-(7)-methacrylate | 20.1 | 8.5 | TMPTA | 0.01 | 0.01 | DLP | 3.60 |
| A2/20 | 80.0 | 91.5 | Laurylpoly-ethoxy-(7)-methacrylate | 20.1 | 8.5 | TMPTA | 0.01 | 0.01 | DLP | 3.60 |
| A2/21 | 80.0 | 91.5 | Laurylpoly-ethoxy-(7)-methacrylate | 20.1 | 8.5 | TMPTA | 0.01 | 0.01 | DLP | 3.60 |
| A2/22 | 80.0 | 93.0 | Stearylpoly-ethoxy-(8)-methacrylate | 19.5 | 7.0 | TMPTA | 0.01 | 0.01 | DLP | 3.90 |
| A2/23 | 80.0 | 93.0 | Stearylpoly-ethoxy-(8)-methacrylate | 19.5 | 7.0 | TMPTA | 0.01 | 0.01 | DLP | 3.90 |
| A2/24 | 80.0 | 93.0 | Stearylpoly-ethoxy-(8)-methacrylate | 19.5 | 7.0 | TMPTA | 0.01 | 0.01 | DLP | 3.90 |

ACDMT = acryloyldimethyltaurate, NVP = N-vinylpyrrollidone, DMAAm = dimethylacrylamide, TMPTA = trimethylolpropane triacrylate, TMPTA = trimethylolpropane triacrylate, TMPTMA = trimethylolpropane trimethacrylate, GPTA = glycerinpropoxylate triacrylate, PEAS = pentaerythritoldiacrylate monostearate, DLP = dilaurylperoxide, V-601 = dimethyl 2,2'-azobis(2-methylpropionate), PEG 600 DMA = polyethylene glycol dimethacrylate (600 g/mol).

Polymer Table B2): Polymers according to polymerization process B2:

| Polymer example name | ACDMT /g | /mol-% | Neutralization reagent Name | /g | Neutral Monomer Name | /g | /mol-% | Crosslinker Name | g | mol-% | Initiator Name | g |
|---|---|---|---|---|---|---|---|---|---|---|---|---|
| B2/1 | 80.0 | 90.0 | NaHCO$_3$ | 32.8 | NVP | 4.3 | 9.0 | TMPTA | 1.27 | 1.00 | DLP | 1.0 |
| B2/2 | 80.0 | 89.5 | NaHCO$_3$ | 32.8 | NVP | 4.3 | 9.0 | TMPTA | 1.92 | 1.50 | V-601 | 1.1 |
| B2/3 | 80.0 | 89.8 | NaHCO$_3$ | 32.8 | NVP | 4.3 | 9.0 | GPTA | 2.30 | 1.25 | DLP | 1.0 |
| B2/4 | 80.0 | 89.7 | NaHCO$_3$ | 32.8 | NVP | 4.3 | 9.0 | PEG 600 DMA | 3.07 | 1.25 | V-601 | 1.1 |
| B2/5 | 80.0 | 96.3 | NaHCO$_3$ | 32.8 | NVP | 1.1 | 2.5 | GPTA | 2.15 | 1.25 | V-601 | 1.1 |
| B2/6 | 80.0 | 91.2 | NaHCO$_3$ | 32.8 | NVP | 3.55 | 7.5 | GPTA | 2.27 | 1.25 | V-601 | 1.1 |
| B2/7 | 80.0 | 93.5 | NaHCO$_3$ | 32.8 | NVP | 2.3 | 5.0 | PEAS | 3.16 | 1.50 | V-601 | 1.1 |
| B2/8 | 80.0 | 87.5 | NaHCO$_3$ | 32.8 | NVP | 4.9 | 10.0 | PEG 600 DMA | 6.28 | 2.50 | DLP | 1.0 |
| B2/9 | 70.0 | 77.5 | NaHCO$_3$ | 28.6 | NVP | 9.7 | 20.0 | PEG 600 DMA | 6.20 | 2.50 | DLP | 1.0 |
| B2/10 | 80.0 | 89.8 | NaHCO$_3$ | 32.8 | NVP | 4.3 | 9.0 | TMPTA | 1.59 | 1.25 | DLP | 1.0 |
| B2/11 | 80.0 | 54.4 | NaHCO$_3$ | 32.8 | DMAAm | 31.5 | 44.8 | GPTA | 2.27 | 0.75 | V-601 | 1.0 |
| B2/12 | 80.0 | 68.9 | NaHCO$_3$ | 32.8 | DMAAm | 16.6 | 29.9 | GPTA | 3.00 | 1.25 | V-601 | 1.0 |
| B2/13 | 80.0 | 74.0 | NaHCO$_3$ | 32.8 | DMAAm | 12.9 | 25.0 | TMPMTA | 1.60 | 1.00 | V-601 | 1.20 |
| B2/14 | 81.5 | 89.0 | NaHCO$_3$ | 32.8 | N-Isopropylacrylamide | 5.0 | 10.0 | TMPTA | 1.31 | 1.00 | V-601 | 1.00 |
| B2/15 | 81.5 | 89.0 | NaHCO$_3$ | 32.8 | N-Isopropylacrylamide | 5.0 | 10.0 | PEG600 DMA | 2.51 | 1.00 | V-601 | 1.00 |
| B2/16 | 80.0 | 95.5 | NaHCO$_3$ | 32.8 | Behenylpolyethoxy-(25)-methacrylate | 21.0 | 3.5 | TMPTA | 1.20 | 1.00 | DLP | 1.75 |
| B2/17 | 80.0 | 96.3 | NaHCO$_3$ | 32.8 | Behenylpolyethoxy-(25)-methacrylate | 18.0 | 3.0 | PEG$_{600}$ DMA | 1.60 | 0.70 | DLP | 1.75 |
| B2/18 | 80.0 | 96.3 | NaHCO$_3$ | 32.8 | Behenylpolyethoxy-(25)-methacrylate | 18.0 | 3.0 | PEG$_{600}$ DMA | 1.60 | 0.70 | DLP | 1.75 |
| B2/19 | 80.0 | 91.5 | NaHCO$_3$ | 32.8 | Laurylpoly-ethoxy-(7)-methacrylate | 20.1 | 8.5 | TMPTA | 0.01 | 0.01 | DLP | 3.60 |
| B2/20 | 80.0 | 91.5 | NaHCO$_3$ | 32.8 | Laurylpoly-ethoxy-(7)-methacrylate | 20.1 | 8.5 | TMPTA | 0.01 | 0.01 | DLP | 3.60 |
| B2/21 | 80.0 | 91.5 | NaHCO$_3$ | 32.8 | Laurylpoly-ethoxy-(7)-methacrylate | 20.1 | 8.5 | TMPTA | 0.01 | 0.01 | DLP | 3.60 |
| B2/22 | 80.0 | 91.5 | NaHCO$_3$ | 32.8 | Laurylpoly-ethoxy-(7)-methacrylate | 20.1 | 8.5 | TMPTA | 0.01 | 0.01 | DLP | 3.60 |
| B2/23 | 80.0 | 93.0 | NaHCO$_3$ | 32.8 | Stearylpoly-ethoxy-(8)-methacrylate | 19.5 | 7.0 | TMPTA | 0.01 | 0.01 | DLP | 3.90 |

Polymer Table B2):
Polymers according to polymerization process B2:

| Polymer example name | ACDMT /g | /mol-% | Neutralization reagent Name | /g | Neutral Monomer Name | /g | /mol-% | Crosslinker Name | g | mol-% | Initiator Name | g |
|---|---|---|---|---|---|---|---|---|---|---|---|---|
| B2/24 | 80.0 | 93.0 | NaHCO$_3$ | 32.8 | Stearylpoly-ethoxy-(8)-methacrylate | 19.5 | 7.0 | TMPTA | 0.01 | 0.01 | DLP | 3.90 |
| B2/25 | 80.0 | 93.0 | NaHCO$_3$ | 32.8 | Stearylpoly-ethoxy-(8)-methacrylate | 19.5 | 7.0 | TMPTA | 0.01 | 0.01 | DLP | 3.90 |

ACDMT = acryloyldimethyltaurate, NVP = N-vinylpyrrolidone, DMAAm = dimethylacrylamide, TMPTA = trimethylolpropane triacrylate, TMPTA = trimethylolpropane triacrylate, TMPTMA = trimethylolpropane trimethacrylate, GPTA = glycerinpropoxylate triacrylate, PEAS = pentaerythritol diacrylate monostearate, DLP = dilaurylperoxide, V-601 = dimethyl 2,2'-azobis(2-methylpropionate), PEG 600 DMA = polyethylene glycol dimethacrylate (600 g/mol).

Polymerization Process A3: General Precipitation Polymerization Procedure in Tert.-Butanol Dose in a 1-Liter Quickfit round bottom flask equipped with a refux condenser, sub surface gas inlet tubing, inner temperature sensor and overhead agitator 400 g tert.-butanol with a water content of 3 wt.-%. Charge 69 g bio-based ACDMT and 9.2 g carboxyethyl acrylate. Neutralize the ACDMT to a pH of 7 to 8 by injection of gaseous ammonia above the surface. Keep the temperature below 40° C. Dose 0.93 g GPTA as a crosslinker and 3.71 g methyl acrylate as a neutral monomer according to Polymer Table A3. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.1 g V-601.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymerization Process B3: General Precipitation Polymerization Procedure in Tert.-Butanol/Dimethylketone Mixture Dose in a 1-Liter Quickfit round bottom flask equipped with a refux condenser, sub surface gas inlet tubing, inner temperature sensor and overhead agitator 200 g tert.-butanol and 200 g dimethylketone with a water content of 2.5 wt.-%. Charge 90 g bio-based ACDMT and 8.25 g carboxyethyl acrylate. Neutralize the ACDMT and the carboxyethyl acrylate by charging 41.3 g sodium hydrogen carbonate. Keep the temperature below 40° C. Dose 0.88 g GPTA, as a crosslinker and a 0.44 g methyl acrylate as a neutral monomer according to Polymer Table B3. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.1 g V-601.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

Polymer Table A3):
Polymers to polymerization process A3:

| Polymer example name | ACDMT/ Mol-% | Anionic monomer Name | /Mol-% | Neutral Monomer Name | /Mol-% | Optional Unit Name | /Mol-% | Crosslinker Name | /Mol-% | Initiator Name | /g |
|---|---|---|---|---|---|---|---|---|---|---|---|
| A3/1 | 75.3 | Carboxyethy acrylate | 14.5 | Methyl acrylate | 9.7 | — | — | GPTA | 0.49 | V-601 | 1.10 |
| A3/2 | 66.8 | Carboxyethy acrylate | 18.0 | DMAAm | 14.7 | — | — | PEAS | 0.50 | DLP | 1.60 |
| A3/3 | 88.0 | Carboxyethy acrylate | 11.59 | Methyl acrylate | 0.01 | — | — | GPTA | 0.40 | V-601 | 1.10 |
| A3/4 | 83.3 | Carboxyethy acrylate oligo | 10.5 | Stearylpoly-ethoxy-(8)-methacrylate | 6.2 | — | — | TMPTA | 0.01 | DLP | 1.80 |
| A3/5 | 89.4 | Carboxyethy acrylate oligo | 10.0 | Methyl acrylate | 0.1 | — | — | TMPMTA | 0.50 | V-601 | 1.10 |
| A3/6 | 88.9 | Carboxyethy acrylate oligo | 9.9 | Methyl acrylate | 0.1 | — | — | PEG 600 DMA | 1.01 | V-601 | 1.10 |
| A3/7 | 76. | Methacrylic acid | 2.6 | DMAAm | 20.7 | — | — | GPTA | 0.52 | V-601 | 1.40 |
| A3/8 | 74.0 | Methacrylic acid | 5.0 | DMAAm | 20.1 | — | — | GPTA | 0.85 | V-601 | 1.50 |
| A3/9 | 73.8 | Methacrylic acid | 5.0 | DMAAm | 20.1 | — | — | PEAS | 1.18 | V-601 | 1.50 |
| A3/10 | 90.5 | Methacrylic acid | 5.4 | Behenylpoly-ethoxy-(25)-methacrylate | 3.3 | — | — | TMPTA | 0.75 | DLP | 1.75 |
| A3/11 | 84.6 | Methacrylic acid | 9.0 | Stearylpoly-ethoxy-(8)-methacrylate | 6.3 | — | — | TMPTA | 0.01 | DLP | 1.80 |
| A3/12 | 74.0 | Methacrylic acid | 5.0 | DMAAm | 20.1 | — | — | GPTA | 0.85 | V-601 | 1.50 |
| A3/13 | 90.5 | Methacrylic acid | 5.4 | Behenylpoly-ethoxy-(25)-methacrylate | 3.3 | — | — | TMPTA | 0.75 | DLP | 1.75 |
| A3/14 | 86.0 | Acrylic acid | 6.0 | Laurylpoly-ethoxy-(7)-methacrylate | 8.0 | — | — | PEAS | 0.01 | DLP | 1.80 |

-continued

Polymer Table A3):
Polymers to polymerization process A3:

| Polymer example name | ACDMT/ Mol-% | Anionic monomer Name | /Mol-% | Neutral Monomer Name | /Mol-% | Optional Unit Name | /Mol-% | Crosslinker Name | /Mol-% | Initiator Name | /g |
|---|---|---|---|---|---|---|---|---|---|---|---|
| A3/15 | 93.4 | Acrylic acid | 6.0 | Methyl acrylate | 0.1 | — | — | GPTA | 0.45 | V-601 | 1.10 |
| A3/16 | 93.1 | Acrylic acid | 6.0 | Methyl acrylate | 0.5 | — | — | GPTA | 0.45 | V-601 | 1.10 |
| A3/17 | 87.6 | 2-ethylacrylic acid | 11.5 | Methyl acrylate | 0.5 | — | — | PEAS | 0.42 | V-601 | 1.10 |
| A3/18 | 94.4 | Itaconic acid | 5.0 | Methyl acrylate | 0.1 | — | — | GPTA | 0.46 | V-601 | 1.10 |
| A3/19 | 91.0 | Itaconic acid | 1.0 | Laurylpoly-ethoxy-(7)-methacrylate | 8.0 | — | — | TMPTA | 0.01 | DLP | 1.80 |
| A3/20 | 94.0 | Itaconic acid | 5.0 | Methyl acrylate | 0.5 | — | — | GPTA | 0.46 | V-601 | 1.10 |
| A3/21 | 80 | Carboxyethy acrylate | 5 | DMAAm | 4.5 | NVP | 5 | GPTA | 0.5 | V-601 | 1.10 |
| A3/22 | 74.25 | Methacrylic acid | 5 | Laurylpoly-ethoxy-(7)-methacrylate | 10 | DMAAm | 10 | TMPTA | 0.75 | DLP | 1.80 |
| A3/23 | 85 | Acrylic acid | 5 | DMAAm | 4.5 | NVP | 5 | PEAS | 0.5 | V-601 | 1.10 |
| A3/24 | 89 | 2-ethylacrylic acid | 5 | DMAAm | 2.5 | Methyl acrylate | 2.5 | TMPMTA | 1 | V-601 | 1.10 |
| A3/25 | 88.5 | Itaconic acid | 5 | DMAAm | 1.5 | NVP | 3.5 | PEG 600 DMA | 1.5 | V-601 | 1.10 |

ACDMT = acryloyldimethyltaurate, NVP = N-vinylpyrollidone, DMAAm = dimethylacrylamide, TMPTA = trimethylolpropantriacrylate, TMPTA = trimethylolpropane triacrylate, TMPTMA = trimethylolpropane trimethacrylate, GPTA = glycerinpropoxylate triacrylate, PEAS = pentaerythritoldiacrylate monostearate, DLP = dilaurylperoxide, V-601 = dimethyl 2,2'-azobis(2-methylpropionate), PEG 600 DMA = polyethylene glycol dimethacrylate (600 g/mol).

Polymer Table B3):
Polymers according to polymerization process B3:

| Polymer example name | ACDMT/ Mol-% | Anionic Monomer Name | /Mol-% | NaHCO₃ /Mol-% | Neutral Monomer Name | /Mol-% | Optional units Name | /Mol-% | Crosslinker Name | /Mol-% | Initiator Name | /g |
|---|---|---|---|---|---|---|---|---|---|---|---|---|
| B3/1 | 87.1 | Carboxyethy acrylate | 11.5 | 41.3 | Methyl acrylate | 1.0 | — | — | GPTA | 0.41 | V-601 | 1.10 |
| B3/2 | 83.3 | Carboxyethy acrylate | 10.5 | 36.5 | Stearylpoly-ethoxy-(8)-methacrylate | 6.2 | — | — | TMPTA | 0.01 | DLP | 1.80 |
| B3/3 | 83.0 | Carboxyethy acrylate | 9.0 | 35.9 | Laurylpoly-ethoxy-(7)-methacrylate | 8.0 | — | — | PEAS | 0.01 | DLP | 1.80 |
| B3/4 | 88.0 | Carboxyethy acrylate | 11.59 | 41.3 | Methyl acrylate | 0.01 | — | — | GPTA | 0.40 | V-601 | 1.10 |
| B3/5 | 88.5 | Carboxyethy acrylate oligo | 9.9 | 40.5 | Methyl acrylate | 0.1 | — | — | GPTA | 1.50 | V-601 | 1.10 |
| B3/6 | 67.9 | Carboxyethy acrylate oligo | 8.5 | 36.5 | DMAAm | 23.1 | — | — | GPTA | 0.50 | DLP | 1.30 |
| B3/7 | 79.0 | Methacrylic acid | 10.2 | 50.3 | DMAAm | 10.1 | — | — | PEAS | 0.70 | V-601 | 1.50 |
| B3/8 | 74.0 | Methacrylic acid | 5.0 | 43.3 | DMAAm | 20.1 | — | — | GPTA | 0.85 | V-601 | 1.50 |
| B3/9 | 90.9 | Methacrylic acid | 8.5 | 39.9 | Methyl acrylate | 0.1 | — | — | GPTA | 0.44 | V-601 | 1.10 |
| B3/10 | 89.0 | Methacrylic acid | 3.0 | 33.5 | Laurylpoly-ethoxy-(7)-methacrylate | 8.0 | — | — | TMPTA | 0.01 | DLP | 1.80 |
| B3/11 | 74.0 | Meth acrylic acid | 5.0 | 43.3 | DMAAm | 20.1 | — | — | GPTA | 0.9 | V-601 | 1.50 |
| B3/12 | 90.6 | Meth acrylic acid | 8.5 | 39.9 | Methyl acrylate | 0.5 | — | — | GPTA | 0.44 | V-601 | 1.10 |
| B3/13 | 89.7 | Acrylic acid | 6.0 | 34.6 | Behenylpoly-ethoxy-(25)-methacrylate | 3.3 | — | — | TMPTA | 1.02 | DLP | 1.75 |
| B3/14 | 87.5 | Acrylic acid | 6.0 | 34.6 | Stearylpoly-ethoxy-(8)-methacrylate | 6.5 | — | — | PEAS | 0.01 | DLP | 1.80 |
| B3/15 | 93.0 | Acrylic acid | 3.0 | 33.5 | Behenylpoly-ethoxy-(25)-methacrylate | 3.3 | — | — | TMPTA | 0.65 | DLP | 1.75 |
| B3/16 | 90.4 | 2-propylacrylic acid | 9.0 | 40.1 | Methyl acrylate | 0.1 | — | — | GPTA | 0.44 | V-601 | 1.10 |
| B3/17 | 90 | Carboxyethy acrylate | 2 | 35.9 | DMMAA | 4.5 | NVP | 3 | GPTA | 0.5 | DLP | 1.75 |
| B3/18 | 85 | Carboxyethy acrylate oligo | 7 | 35.9 | Stearylpoly-ethoxy-(8)-methacrylate | 3 | NVP | 4 | TMPTA | 1 | V-601 | 1.10 |
| B3/19 | 86.8 | Acrylic acid | 7 | 36.5 | Laurylpoly-ethoxy-(7)-methacrylate | 3 | NVP | 2.7 | TMPTA | 0.5 | DLP | 1.75 |
| B3/20 | 86.8 | Methacrylic acid | 7 | 36.5 | Behenylpoly-ethoxy-(25)-methacrylate | 3.3 | NVP | 2.2 | GPTA | 0.7 | V-601 | 1.10 |

ACDMT = acryloyldimethyltaurate, NVP = N-vinylpyrollidone, DMAAm = dimethylacrylamide, TMPTA = trimethylolpropane triacrylate, TMPTA = trimethylolpropane triacrylate, TMPTMA = trimethylolpropane trimethacrylate, GPTA = glycerinpropoxylate triacrylate, PEAS = pentaerythritoldiacrylate monostearate, DLP = dilaurylperoxide, V-601 = dimethyl 2,2'-azobis(2-methylpropionate), PEG 600 DMA = polyethylene glycol dimethacrylate (600 g/mol).

Polymerization Process X: Solution Homopolymer of ACDMT in Water.

In a 1-L 5-neck round bottom flask, equipped with an overhead stirrer and an anchor type stirrer, a pH probe, sub-surface nitrogen inlet, dropping funnel, intensive condenser and a gas out let valve 450 g distilled water was filled. 50 g bio-based ACDMT (the ACDMT generated in Monomer Example 1) was dissolved. The agitator was set to rotate with 200 rpm. Cooling with a water bath at 20° C. the solution was neutralized with approximately 19 g 50% sodium hydroxide solution to a pH value of 7±0.5. After the neutralization the reaction mixture was heated to 50° C.±0.5° C. temperature. During the heating phase nitrogen was purged through the solution with a flow rate of 60 l/h. The temperature was stabilized and the nitrogen purge continued for 60 minutes. After this 60 minutes the nitrogen was dosed above the liquid surface and the polymerization was initiated by addition of 0.10 g 2,2'-azobis(2-methylpropionamidine)dihydrochloride (V-50 by Wako Specialty Chemicals).

10 minutes after the reaction was started the purge was reduced to 6 l/h. After the temperature maximum was reached the bath temperature was maintained at 50° C. for one hour. Then the bath temperature was increased to 80° C. for 2 h, then cooled to room temperature. The Brookfield viscosity of the solution as was measured at 25° C., 20 rpm, using a spindle delivering a value of 20 to 80% of the maximum scale.

Also the Fickenscher k-Value was determined.

Polymerization Process Y: Homopolymer of ACDMT by Precipitation Polymerization in Tert.-Butanol In a 1-Liter Quickfit round bottom flask equipped with a refux condenser, sub surface gas inlet tubing, inner temperature sensor and overhead agitator 400 g tert.-butanol was dosed. 100 g bio-based ACDMT was charged and was neutralized to a pH of 7 to 8 by injection of gaseous ammonia above the surface. The temperature was kept below 40° C. At agitation of 200 rpm nitrogen was inject subsurface for 1 h. During this time the temperature of the reaction mixture was raised and stabilized to 60° C. with help of a water bath. At 60° C. the pH was readjusted to a pH of 7 to 8. Then the reaction was initiated by the dosage of 1.0 g of 2,2'-azobis(isobutyronitrile).

After a few minutes the polymerization start became obvious by a raising temperature and the precipitation of a polymer. After the temperature maximum was reached the reaction mixture was heated to a gentle reflux for two hours. Then the polymer was cooled to room temperature and dried at 60° C. under a vacuum of 150 mbar.

The resulting polymer powder was dissolved 0.5% in water and the Fickenscher k-value was measured.

Polymerization Process Z: Synthesis of a Co-Polymer of ACDMT and Acrylamide by Precipitation Polymerisation in Tert.-Butanol.

In a 1-Liter Quickfit round bottom flask equipped with a refux condenser, sub surface gas inlet tubing, inner temperature sensor and overhead agitator 400 g tert.-butanol was dosed. 70 g bio-based ACDMT was charged. The ACDMT was neutralized to a pH of 7 to 8 by injection of gaseous ammonia above the surface. The temperature was kept below 40° C., then 30 g of acrylamide was dissolved in the reaction mixture. At agitation of 200 rpm nitrogen was inject subsurface for 1 h. during this time the temperature of the reaction mixture was raised and stabilized to 60° C. with help of a water bath. At 60° C. the pH was readjusted to a pH of 7 to 8. Then the reaction was initiated by the dosage of 1.0 g of 2,2'-azobis(isobutyronitrile).

After a few minutes the polymerization start becomes obvious by a raising temperature and the precipitation of a polymer. After the temperature maximum was reached the reaction mixture was heated to a gentle reflux for two hours. Then the polymer was cooled to room temperature and dried at 60° C. under a vacuum of 150 mbar.

The resulting polymer powder was dissolved 0.5% in water and the Fickenscher k-value was measured.

Drying Acrylonitrile 500 ml acrylonitrile ≥99%, contained 35-45 ppm monomethyl ether hydroquinone as inhibitor from Sigma-Aldrich, contained 0.41% water before drying. It was dried by adding 50 g molecular sieve 0.4 nm from Merck Millipore, Merck KGaA. The residual water content of the acrylonitrile was 19 ppm, measured by Karl-Fischer titration (DIN 51777).

Analytical Methods

Determination of the Fickenscher k-Value:

This method was used to determine the k-value of certain polymers according to DIN EN ISO 1628-1.

A k-value measurement was a way to indirectly analyze the molecular weight/size of a polymer. A comparatively higher K-value corresponds to a larger molecular weight/size as compared to a polymer with the same composition and made by the same process.

By measuring the measuring the pass-through time of a solvent ($t^0$) and the pass-through time of a polymer solution ($t^c$) through the capillary of an Ubbelhode viscometer the relative viscosity was determined.

$$Z = \frac{t_c}{t_0} + \frac{\eta_c}{\eta_0}$$

From the relative viscosity z the k-value can be calculated according to $$\lg z = \left[\frac{75\ k^2}{1 + 150\ k \times c} + k\right] \times 1$$

In this case $$k = \frac{1.51\ \lg z - 1 \pm \sqrt{1 + \left(\frac{2}{c} + 2 + 1.5\ \lg z\right) 1.5\ \lg z}}{150 + 300\ c}$$

$k$-value = 1000 k

Here in it was defined:

$$Z = \frac{t_c}{t_0} = \frac{\eta_c}{\eta_0}$$

relative Viscosity,
$\eta_c$ dynamic viscosity of the solution,
$\eta_o$ dynamic viscosity of the solvent and
$\eta$ c mass concentration of polymer in solution in in g/cm³

Alternatively the k-value can be evaluated from lists provided by the manufacturer of the equipment.

After determination of the mass concentration of the polymer solution by microwave drying with a CEM Smart 5 at 120° C., 20 ml of a 0.5% polymer solution was prepared. 16 to 18 ml of the solution was measured in an Ubbelhode capillary viscometer at 25° C. The Ubbelhode viscometer was chose to have a pass-through time of 100 to 120 s. It was measured in a Schott AVS viscometer, combined with a CT 1150 Thermostate and flow cooler CK 100.

The IT unit calculated the k-value.

Brookfield Viscosity in 1% Solution:

Brookfield viscosity was determined with a Brookfield viscometer model LV, RVT DV-II or LVT DV-II.

In a 600 ml beaker, 4 g dry polymer was dissolved in 394 g distilled water. The solution was stirred for 2 h at 20° C. with a finger stirrer driven by an overhead agitator at 200 rpm. Then the polymer solution, free of entrapped air, was tempered for 16 h at 20° C. The spindle was chosen to measure between 20 to 80% of the scale at 20 rpm.

Brookfield Viscosity in Solution as is.

Brookfield viscosity was determined with a Brookfield viscometer model LV, RVT DV-II or LVT DV-II.

In a 600 ml beaker, the polymer solution, free of entrapped air, was tempered for 2 h at 20° C. The spindle was chosen to measure between 20 to 80% of the scale at 20 rpm.

Analytical procedure for determination of bio-based content according to ASTM 6866-12, Method B:

The provided sample material did not undergo any pre-treatment procedure and was converted to graphite as was using the following procedure.

Depending on the estimated amount of carbon content, typically a few milligram of sample material was being combusted in an Elemental Analyzer (EA). The resulting gas mixture was being cleaned and $CO_2$ was automatically separated by the EA using the purge and trap technology.

The remaining $CO_2$ was transferred into a custom-made graphitization system, converted into carbon (graphite) catalytically using $H_2$ and an iron-powder catalyst.

The carbon-14 determination of the graphite was performed at the Klaus-Tschira-Archaeomtrie-Center using an accelerator mass-spectrometer (AMS) of the type MICADAS (developed at the ETH Zurich, Switzerland).

Composition Examples

The following composition examples comprise the polymer according to the present invention e.g. as Polymer X. Polymer X can relate to any of Polymers A1/1 to A1/15, B1/1 to B1/20, A2/1 to A2/24, B2/1 to B2/25, A3/1 to A3/25 and to B3/1 to B3/20 (see above Polymer Tables for their respective compositions).

Example Composition 1: After-Sun Cream Gel

| | |
|---|---|
| Mineral Oil | 3.00% |
| Isopropyl Palmitate | 3.00% |
| Cetearyl Isononanoate | 3.00% |
| Jojoba Oil | 3.00% |
| Walnut Oil | 3.00% |
| Tocopheryl Acetate | 1.00% |
| Polymer X | 1.20% |
| Water | ad 100% |
| Glycerin | 3.00% |
| Allantoin (Clariant) | 0.20% |
| Nipaguard ® POM (Clariant) | 1.00% |
| Phenoxyethanol, Methylparaben, Piroctone Olamine | |
| Panthenol | 1.00% |
| Collagen nativ 1% | 3.00% |
| Ethanol | 1.50% |

Example Composition 2: Sun Milk SPF 15

| | |
|---|---|
| Ethylhexyl Stearate | 7.00% |
| Decyl Oleate | 5.00% |
| Plantasens ® Natural Emulsifier HE 20 (Clariant) Cetearyl Glucoside (and) Sorbitan Olivate | 3.00% |
| Dimethicone | 2.00% |
| Octocrylene | 7.00% |
| Butyl Methoxydibenzoylmethane | 2.50% |
| Ethylhexyl Salicylate | 4.50% |
| Water | Ad 100% |
| Glycerin | 3.00% |
| Polymer X | 1.00% |
| Nipaguard ® POM (Clariant) Phenoxyethanol (and) Piroctone Olamine (and) Methylparaben | 1.00% |
| Citric Acid | q.s. |

Example Composition 3: Liquid Soap

| | |
|---|---|
| Water | Ad 100% |
| Glycerin | 3.00% |
| 1,2-Propanediol | 2.00% |
| Polymer X | 2.00% |
| Genapol ® LRO liquid (Clariant) Sodium Laureth Sulfate | 20.00% |
| Genagen ® CAB 818 (Clariant) Cocamidopropyl Betaine | 4.00% |
| GlucoTain ® Clear (Clariant) Capryloyl/Caproyl Methyl Glucamide | 2.00% |
| Nipaguard ™ DMDMH (Clariant) DMDM Hydantoin | 0.40% |
| Fragrance | 0.20% |
| Sodium Cloride | 0.50% |

Example Composition 4: Effect Shower Gel

| | |
|---|---|
| Genapol ® LRO liquid (Clariant) Sodium Laureth Sulfate | 30.00% |
| Genagen ® CAB 818 (Clariant) Cocamidopropyl Betaine | 6.00% |
| Hostapon ® KCG (Clariant) Sodium Cocoyl Glutamate | 5.00% |
| Water | Ad 100% |
| Polymer X | 1.40% |
| Nipaguard ® DMDMH (Clariant) DMDM Hydantoin | 0.50% |
| Cirebelle 104 Blue Sythetic Wax | 1.00% |

Example Composition 5: Facial Cleanser

| | |
|---|---|
| Water | Ad 100% |
| Polymer X | 1.80% |
| Genapol ® LRO paste (Clariant) Sodium Laureth Sulfate | 4.50% |
| Medialan ® LD (Clariant) Sodium Lauroyl Sarcosinate | 13.50% |
| Genagen ® CAB 818 (Clariant) Cocamidopropyl Betaine | 3.00% |
| Citric Acid | q.s. |
| Benzoic Acid | 0.50% |

Example Composition 6: Mascara

| | |
|---|---|
| Hydroxyethylcellulose | 0.50% |
| Polymer X | 0.50% |
| 1,2-Propyleneglycol | 1.00% |
| Magnesium Aluminium Silicate | 1.00% |
| Triethanolamine 99% | 1.50% |
| Water | Ad 100% |
| Stearic Acid | 3.00% |
| SilCare ® Silicone 41M15 (Clariant) Caprylyl Methicone | 1.00% |
| SilCare ® Silicone 31M50 (Clariant) Caprylyl Trimethicone | 2.00% |
| Tego ® Care 450 Polyglyceryl-3 Methylglucose Distearate | 4.00% |
| Polybutene. | 2.00% |
| Beeswax | 2.50% |
| Plantasens ® Olive Wax S51 (Clariant) Hydrogenated Olive Oil | 2.50% |
| Microcrystalline Wax | 3.50% |
| Iron Oxides | 10.0% |
| Phenonip ™ ME (Clariant) Phenoxyethanol, Methylparaben, Ethylparaben | 1.00% |
| Baycusan ® C 1004 Polyurethane-35 | 2.00% |

Example Composition 7: BB Cream SPF 15

| | |
|---|---|
| Water | Ad 100% |
| Glycerin | 2.00% |
| Polymer X | 1.00% |
| Hostaphat ® KW 340 D (Clariant) Triceteareth-4 Phosphate | 3.00% |
| Cetearyl Alcohol | 2.00% |
| Octocrylene | 7.00% |
| Butyl Methoxydibenzoylmethane | 2.50% |
| Ethylhexyl Salicylate | 4.50% |
| Plantasens ® Olive LD (Clariant) Hydrogenated Ethylhexyl Olivate (and) Hydrogenated Olive Oil Unsaponifiables | 2.00% |
| 12-15 Alkyl Benzoate | 8.00% |
| Plantasens ® Olive Squalane (Clariant) Squalane | 2.00% |
| Plantasens ® Shea Butter (Clariant) Butyrospermum Parkii (Shea) Butter | 1.00% |
| XIAMETER ® PMX-200 Silicone Fluid 200 CS Dimethicone | 2.00% |
| Chroma-Lite ® Black Mica (and) Bismuth Oxychloride (and) Iron Oxides | 0.05% |
| Chroma-Lite ® Red Mica (and) Bismuth Oxychloride (and) Iron Oxides | 0.20% |
| Chroma-Lite ® Yellow Mica (and) Bismuth Oxychloride (and) Iron Oxides | 0.60% |
| Titanium Dioxide | 5.00% |
| Butylene Glycol | 4.00% |
| Plantasens ® Natural Vitamin E (Clariant) Tocopherol | 1.00% |
| Panthenol | 0.50% |
| Sodium Hyaluronate | 0.40% |
| Fragrance | 0.20% |
| Nipaguard ® POB (Clariant) Phenoxyethanol (and) Piroctone Olamine (and) Benzoic Acid | 0.80% |
| Citric Acid | q.s. |

Example Composition 8: O/W Foundation

| | |
|---|---|
| Water | Ad 100% |
| Polymer X | 1.00% |
| Magnesium Aluminium Silicate | 1.00% |
| Plantasens ® Natural Emulsifier HP10 (Clariant) Sucrose Polystearate, Cetearyl Alcohol, Olea Europaea (Olive) Oil Unsaponifiables | 4.50% |
| SilCare ® Silicone 31M50 (Clariant) Caprylyl Trimethicone | 2.00% |
| XIAMETER ® PMX-200 Silicone Fluid 100 CS Dimethicone | 2.00% |
| Caprylic/Capric Triglyceride | 5.00% |
| Plantasens ® Olive Wax S51 (Clariant) Hydrogenated Vegetable Oil | 1.50% |
| Chroma-Lite ® Black Mica (and) Bismuth Oxychloride (and) Iron Oxides | 0.10% |
| Chroma-Lite ® Red Mica (and) Bismuth Oxychloride (and) Iron Oxides | 0.40% |
| Chroma-Lite ® Yellow Mica (and) Bismuth Oxychloride (and) Iron Oxides | 1.20% |
| Titanium Dioxide | 7.00% |
| Dicaprylyl Carbonate | 4.00% |
| Butylene Glycol | 3.00% |
| Plantasens ® Natural Vitamin E (Clariant) Tocopherol | 1.00% |
| Orgasol ® 4000 EXD NAT COS Caresse Nylon-6/12 | 1.00% |
| Fragrance | 0.20% |
| Nipaguard ® POB (Clariant) Phenoxyethanol (and) Piroctone Olamine (and) Benzoic Acid | 0.80% |

Example Composition 9: Liquid Highlighter

| | |
|---|---|
| Water | Ad 100% |
| Bentonite | 1.00% |
| Polymer X | 1.00% |
| Liquiwax ™ PolyIPL Stearyl/PPG-3 Myristyl Ether Dimer Dilinoleate | 2.00% |
| Plantasens ® Olive Wax S51 (Clariant) Hydrogenated Olive Oil | 2.00% |
| Stearic Acid | 1.20% |
| Isostearic Acid | 0.90% |
| Water | 5.00% |
| Sodium Hydroxide | 0.12% |
| Orgasol ® 4000 EXD NAT COS Caresse Nylon-6/12 | 1.50% |
| Timiron ® Super Gold Mica, Titanium Dioxide | 2.50% |
| Xirona ® Indian Summer Silica (and) Iron Oxides | 2.50% |
| Panthenol | 0.50% |
| Cyclopentasiloxane | 7.50% |
| Phenonip ™ ME (Clariant) Phenoxyethanol, Methylparaben, Ethylparaben | 1.00% |
| Tocopheryl Acetate | 1.00% |

Example Composition 10: Lipstain

| | |
|---|---|
| Water | Ad 100% |
| Glycerin | 30.00% |
| Polymer X | 3.00% |
| FD&C Red No. 40 CI16035 | 0.15% |
| Emulsogen ® HCO 040 (Clariant) PEG-40 Hydrogenated Castor Oil | 0.50% |
| Phenonip ™ ME (Clariant) Phenoxyethanol, Methylparaben, Ethylparaben | 1.00% |
| Flavour | 0.20% |

Example Composition 11: Eyeliner Gel

| | |
|---|---|
| Water | Ad 100% |
| Glycerin | 1.00% |
| Polymer X | 2.00% |
| Phenonip ™ ME (Clariant) Phenoxyethanol, Methylparaben, Ethylparaben | 1.00% |
| PVP | 1.50% |
| Water | 10.00% |
| Timiron ® Super Gold Mica, CI77891, Titanium Dioxide | 12.00% |

Example Composition 12: After-Shave Balm

| | |
|---|---|
| Hostaphat ® KL 340 D (Clariant) Trilaureth-4 Phosphate | 2.00% |
| Octopirox ® (Clariant) Piroctone Olamine | 0.05% |
| Plantasens ® Abyssinian Oil (Clariant) Crambe Abyssinica Seed Oil | 2.00% |
| Isopropyl Isostearate | 3.00% |
| Plantasens ® Inca Inchi Serum (Clariant) Plukenetia Volubilis Seed Oil (and) Phytosterols (and) Olea Europaea (Olive) Oil Unsaponifiables (and) Beeswax | 1.00% |
| Water | Ad 100% |
| Polyglykol 400 (Clariant) PEG-8 | 3.00% |
| Allantoin | 0.30% |
| Polymer X | 1.50% |
| Dimethicone | 1.00% |
| Citric Acid | q.s. |
| Phenonip ™ ME (Clariant) Phenoxyethanol, Methylparaben, Ethylparaben | 1.00% |

Example Composition 13: Sprayable Body Milk

| | |
|---|---|
| Hostaphat ® KL 340 D (Clariant) Trilaureth-4 Phosphate | 1.00% |
| Mineral Oil | 8.00% |
| Isopropyl Palmitate | 3.00% |
| Cetearyl Alcohol | 0.50% |
| Caprylic/Capric Triglyceride | 2.00% |
| Glyceryl Stearate | 0.50% |
| SilCare ® Silicone 41M15 (Clariant) Caprylyl Methicone | 1.00% |
| Polymer X | 1.00% |
| Water | ad 100% |
| Glycerin | 5.00% |
| Ethanol | 5.00% |
| Tocopheryl Acetate | 1.00% |
| Nipaguard ® POM (Clariant) Phenoxyethanol, Methylparaben, Piroctone Olamine | 1.00% |

Example Composition 14: Body Lotion for Men

| | |
|---|---|
| Caprylic/Capric Triglyceride | 3.50% |
| Plantasens ® Olive LD (Clariant) Hydrogenated Ethylhexyl Olivate (and) Hydrogenated Olive Oil Unsaponifiables | 3.00% |
| Myristyl Myristate | 2.50% |
| Cetearyl Alcohol | 2.00% |
| Octyldodecanol | 1.00% |
| Glyceryl Stearate Citrate | 1.50% |
| Polymer X | 1.20% |
| Water | ad 100% |
| Glycerin | 5.00% |
| Ethanol | 3.00% |
| Tocopheryl Acetate | 1.00% |
| Aloe Barbadensis Leaf Juice | 1.00% |
| Nipaguard ® POM (Clariant) Phenoxyethanol, Methylparaben, Piroctone Olamine | 1.00% |
| Fragrance | 0.20% |
| Sodium Hydroxide | q.s. |

Example Composition 15: Anti-Ageing Cream Gel

| | |
|---|---|
| Caprylic/Capric Triglyceride | 5.00% |
| Dicaprylyl Ether | 5.00% |
| Cetearyl Alcohol | 2.00% |
| Nipaguard ® POB (Clariant) Phenoxyethanol (and) Piroctone Olamine (and) Benzoic Acid | 0.80% |
| Ubiquinone | 0.10% |
| Aristoflex ® HMB (Clariant) Ammonium Acryoyldimethyltaurate/ Beheneth-25 Methacrylate Crosspolymer | 0.40% |
| Polymer X | 0.40% |
| Sodium Hyaluronate | 0.30% |
| Water | Ad 100% |
| Tocopheryl Acetate | 0.30% |
| Fragrance | 0.30% |

Example Composition 16: Light Day Cream

| | |
|---|---|
| Water | Ad 100% |
| Polymer X | 0.75% |
| Glycerin | 3.00% |
| Plantasens ® Natural Emulsifier HE20 (Clariant) Cetearyl Glucoside, Sorbitan Olivate | 1.20% |
| Aristoflex ® AVC (Clariant) Ammonium Acryloyldimethyltaurate/VP Copolymer | 0.10% |
| Plantasens ® Abyssinian Oil (Clariant) Crambe Abyssinica Seed Oil | 3.00% |
| Octyldodecanol | 5.00% |
| Isodecyl Neopentanoate | 3.00% |
| Plantasens ® Natural Vitamin E (Clariant) Tocopherol | 0.50% |
| Nipaguard ® SCP (Clariant) Phenoxyethanol (and) Sorbitan Caprylate | 1.00% |

Example Composition 17: Caring Night Cream

| | |
|---|---|
| Water | Ad 100% |
| Glycerin | 2.00% |
| Polymer X | 1.00% |
| Hostaphat ® KW 340 D (Clariant) | 2.00% |
| Triceteareth-4 Phosphate | |
| Plantasens ® Oat Serum (Clariant) | 3.00% |
| *Avena Sativa* (Oat) Kernel Oil (and) | |
| Phytosterols (and) *Olea Europaea* (Olive) Oil | |
| Unsaponifiables (and) Beeswax | |
| Plantasens ® Shea Butter (Clariant) | 7.00% |
| *Butyrospermum Parkii* (Shea) Butter | |
| Isopropyl Palmitate | 5.00% |
| *Macadamia Integrifolia* Seed Oil | 4.00% |
| *Cera Alba* (Beeswax) | 3.00% |
| Nipaguard ® SCP (Clariant) | 1.00% |
| Phenoxyethanol (and) Sorbitan Caprylate | |
| Fragrance | 0.30% |
| Sodium Hydroxide | 0.10% |

Example Composition 18: Sprayable Hair Styling Gel

| | |
|---|---|
| Polymer X | 0.90% |
| Water | Ad 100% |
| Genapol ® LA-230 (Clariant) | 4.00% |
| Laureth-23 | |
| Diaformer ® Z-632N (Clariant) | 4.50% |
| Acrylates/Stearyl Acrylate/Ethylamine Oxide Methacrylate Copolymer | |
| Dipropylene Glycol | 1.00% |
| Polyglykol 400 | 0.50% |
| PEG-8 | |
| Nipaguard ™ DMDMH (Clariant) | 0.50% |
| DMDM Hydantoin | |
| Panthenol | 0.50% |
| Emulsogen ® HCO 040 (Clariant) | 0.50% |
| PEG-40 Hydrogenated Castor Oil | |
| Fragrance | 0.30% |

Example Composition 19: Conditioning Shampoo

| | |
|---|---|
| Water | Ad 100% |
| Polymer X | 1.10% |
| Genapol ® LRO liquid (Clariant) | 30.00% |
| Sodium Laureth Sulfate | |
| Genagen ® CAB 818 (Clariant) | 6.00% |
| Cocamidopropyl Betaine | |
| XIAMETER ® PMX-200 Silicone Fluid 50 CS | 0.25% |
| Dimethicone | |
| Water | 10.00% |
| Jaguar ® C-162 | 0.20% |
| Hydroxypropyl Guar (and) Hydroxypropyl Guar Hydroxypropyltrimonium Chloride | |
| Citric Acid | q.s. |
| Water | 4.00% |
| Sodium Benzoate | 0.45% |
| Sodium Chloride | 0.50% |

Example Composition 20: Nail Varnish Remover Gel

| | |
|---|---|
| Water | Ad 100% |
| Ethanol | 27.00% |
| Polyglykol ® 400 (Clariant) | 3.00% |
| PEG-8 | |
| Glycerin | 3.00% |
| Aristoflex ® TAC (Clariant) | 0.20% |
| Ammonium Acryloyldimethyltaurate/ Carboxyethyl Acrylate Crosspolymer | |
| Polymer X | 1.00% |
| Ethyl Acetate | 30.00% |

Example Composition 21: Skin-Whitening Gel

| | |
|---|---|
| Genapol ® T 250 (Clariant) | 2.00% |
| Ceteareth-25 | |
| Genapol ® DAT 100 (Clariant) | 1.10% |
| PEG-150 Polyglyceryl-2 Tristearate | |
| Water | Ad 100% |
| Ascorbic Acid 2- Glucoside | 3.00% |
| Polymer X | 1.50% |
| Nipaguard ™ DMDMH Plus (Clariant) | 2.00% |
| DMDM Hydantoin | |

Example Composition 22: Self-Tanning Cream

| | |
|---|---|
| Hostaphat ® CC 100 (Clariant) | 1.00% |
| Cetyl Phosphate | |
| Glyceryl Stearate | 0.50% |
| Cetearyl Alcohol | 0.50% |
| Mineral Oil | 8.00% |
| Isopropyl Palmitate | 7.00% |
| Tocopheryl Acetate | 1.00% |
| SilCare ® Silicone 41M15 (Clariant) | 1.00% |
| Caprylyl Methicone | |
| Polymer X | 2.00% |
| Water | ad 100% |
| Hostapon ® KCG (Clariant) | 0.50% |
| Sodium Cocoyl Glutamate | |
| Glycerin | 5.00% |
| Fragrance | 0.20% |
| Phenonip ™ ME (Clariant) | 1.00% |
| Phenoxyethanol, Methylparaben, Ethylparaben | |
| Dihydroxyacetone | 5.00% |
| Water | 8.00% |
| Sodium Hydroxide | q.s. |

Example Composition 23: Make-Up Remover

| | |
|---|---|
| Water | ad 100% |
| Glycerin | 3.00% |
| Polymer X | 0.80% |
| Hostaphat ® KL 340 D (Clariant) | 3.00% |
| Trilaureth-4 Phosphate | |
| Cetearyl Alcohol | 1.50% |
| Plantasens ® Olive LD (Clariant) | 2.00% |
| Hydrogenated Ethylhexyl Olivate (and) Hydrogenated Olive Oil Unsaponifiables | |
| Isostearyl Isostearate | 4.00% |
| Isohexadecane | 4.00% |

| | |
|---|---|
| Sodium Hydroxide | q.s. |
| Nipaguard ® SCP (Clariant) | 1.00% |
| Phenoxyethanol (and) Sorbitan Caprylate | |
| Fragrance | 0.20% |

Example Composition 24: Insect Repellent Lotion

| | |
|---|---|
| Diethyl Toluamide | 10.00% |
| DEET | |
| Hostaphat ® KL 340 D (Clariant) | 1.00% |
| Trilaureth-4 Phosphate | |
| Isohexadecan | 5.00% |
| C12-15 Alkyl Benzoate | 5.00% |
| Cyclopentasiloxane | 2.00% |
| Polymer X | 1.00% |
| Water | Ad 100% |
| Ethanol | 10.00% |
| Fragrance | 0.30% |
| Nipaguard ® POB (Clariant) | 0.80% |
| Phenoxyethanol (and) Piroctone Olamine (and) Benzoic Acid | |

Example Composition 25: Facial Toner

| | |
|---|---|
| Water | ad 100% |
| Glycerin | 5.00% |
| Butylene Glycol | 3.00% |
| Alcohol | 5.00% |
| Polymer X | 0.20% |
| Emulsogen ® HCO 040 (Clariant) | 0.40% |
| PEG-40 Hydrogenated Castor Oil | |
| Fragrance | 0.30% |
| Tocopheryl Acetate | 0.50% |
| Panthenol | 0.30% |
| Nipaguard ® SCP (Clariant) | 1.00% |
| Phenoxyethanol (and) Sorbitan Caprylate | |
| Citric acid | q.s. pH 5.5 |

Example Composition 26: Depilating Cream

| | |
|---|---|
| Cetyl Alcohol | 4.00% |
| Ceteareth-20 | 3.00% |
| Cetearyl Alcohol | 2.00% |
| Caprylic/Capric Triglyceride | 5.00% |
| Mineral Oil | 2.00% |
| Water | ad 100% |
| Tetrasodium EDTA | 0.10% |
| Polymer X | 3.00% |
| Potassium Hydroxide (50% sol) | 2.00% |
| Calcium Hydroxide | 5.00% |
| Potassium Thioglycolate | 10.0% |
| Fragrance | 0.30% |
| Tocopheryl Acetate | 0.50% |
| Panthenol | 0.30% |

Example Composition 27: Face Mask

| | |
|---|---|
| Water | ad 100% |
| Polymer X | 2.00% |
| Glycerin (85%) | 5.00% |
| Glucotain ® Care (Clariant) | 2.00% |
| Cocoyl Methyl Glucamide | |
| Plantasens ® Grape Seed Serum (Clariant) | 1.00% |
| Vegetable Oil (and) Phytosterols (and) *Olea Europaea* (Olive) Oil Unsaponifiables | |
| Plantasens ® Abyssinian Oil (Clariant) | 3.00% |
| *Crambe Abyssinica* Seed Oil | |
| Hostacerin ® SFO (Clariant) | 2.00% |
| Sunflower Seed Oil Sorbitol Esters | |
| Kaolin | 4.00 |
| Green Clay | 4.00 |
| Titanium Dioxide | 2.00 |
| Nipaguard ® POM (Clariant) | 1.00 |
| Phenoxyethanol (and) Piroctone Olamine (and) Methylparaben | |
| Sodium Acetate | 0.10 |
| Citric Acid | q.s. |

Example Composition 28: Micellar Gel

| | |
|---|---|
| Water | ad 100% |
| Polymer X | 1.00% |
| Glycerin (85%) | 3.00% |
| GlucoTain ® Clear (Clariant) | 4.00% |
| Capryloyl/Caproyl Methyl Glucamide | |
| Propylene Glycol | 2.00% |
| Sodium Citrate | 0.10% |
| Emulsogen ® HCO 40 (Clariant) | 1.00% |
| PEG-40 Hydrogenated Castor Oil | |
| Nipaguard ® POM (Clariant) | 1.00% |
| Phenoxyethanol, Methylparaben, Piroctone Olamine | |
| Citric Acid | q.s. |

Example Composition 29: Lubricating Gel

| | |
|---|---|
| Water | ad 100% |
| Polymer X | 0.50% |
| Glycerin (85%) | 5.00% |
| Polyglycol 300 | 3.00% |
| PEG-6 | |
| *Aloe Barbadensis* Leaf Juice | 0.30% |

Example Composition 30: Emulsion for Wet Wipes

| | |
|---|---|
| Emulsogen ® CCT Green (Clariant) | 2.50% |
| Caprylic/Capric Triglyceride, Water, Lauryl Glucoside, Glycerin, Sodium Lauroyl Lactylate, Glyceryl Stearate, Cetearyl Alcohol, Sodium Stearoyl Lactylate | |
| Isopropyl Stearate | 5.00% |
| Plantasens ® Abyssinian Oil (Clariant) | 0.50% |
| *Crambe Abyssinica* Seed Oil | |
| Tocopheryl Acetate | 0.10% |
| Fragrance | 0.20% |
| Water | ad 100% |
| Polymer X | 0.10% |
| Panthenol | 0.10% |
| Nipaguard ® SCE (Clariant) | 1.50% |
| Sorbitan Caprylate (and) Propanediol (and) Benzoic Acid | |

Example Composition 31: Antiperspirant for Roll-Ons

| | |
|---|---|
| Hydroxyethyl cellulose | 0.30% |
| Alcohol | 25.0% |
| Water | ad 100% |
| Polymer X | 0.50% |
| Locron ® LIC (Clariant) | 25.0% |
| Aluminium Chlorodydrate | |
| Propylene Glycol | 2.00% |
| Panthenol | 0.10% |
| Emulsogen ® HCO 40 (Clariant) | 1.00% |
| PEG-40 Hydrogenated Castor Oil | |
| Fragrance | 0.30% |

Example Composition 32: Shaving Gel

| | |
|---|---|
| Water | ad 100% |
| Glycerin | 5.00% |
| Polymer X | 1.50% |
| Genapol ® LT (Clariant) | 1.00% |
| PEG-150 Polyglyceryl-2 Tristearate (and) Laureth-3 (and) Dipropylene Glycol | |
| Genagen ® SC 15 (Clariant) | 6.00% |
| Sodium Laureth Sulfate (and) Cocamide MEA (and) Aqua | |
| Genagen ® CAB 818 (Clariant) | 3.00% |
| Cocamidopropyl Betaine | |
| Sodium Hydroxide (50% sol) | 0.50% |
| Panthenol | 0.10% |
| Allantoin | 0.20% |
| Polyglycol 300 (Clariant) | 0.50% |
| PEG-6 | |
| Phenonip ® ME (Clariant) | 0.90% |
| Phenoxyethanol, Methylparaben, Ethylparaben | |
| Fragrance | 0.30% |

Example Composition 33: Hand Sanitizer

| | |
|---|---|
| Water | ad 100% |
| Glycerin | 2.00% |
| Polymer X | 0.50% |
| Ethanol | 70.0% |
| XIAMETER ® OFX-5324 Fluid | 6.00% |
| PEG-12 Dimethicone | |
| *Aloe Barbadensis* Leaf Extract | 0.30% |

Example Composition 34: Hair Serum

| | |
|---|---|
| Water | ad 100% |
| Glycerin | 5.00% |
| Propylene Glycol | 3.00% |
| Polymer X | 2.00% |
| XIAMETER ® PMX-200 (50cs) | 2.00% |
| Dimethicone | |
| XIAMETER ® PMX-0245 | 3.00% |
| Cyclopentasiloxane | |
| Polysorbate-20 | |
| Sodium Hyaluronate | 1.00% |
| Nipaguard ® POM (Clariant) | 1.00% |
| Phenoxyethanol (and) Piroctone Olamine (and) Methylparaben | |
| Fragrance | 0.50% |

Example Composition 35: Hair Detangling Cream

| | |
|---|---|
| Water | ad 100% |
| Glycerin | 3.00% |
| Polymer X | 1.50% |
| Hostacerin ® SFO (Clariant) | 2.00% |
| Sunflower Seed Oil Sorbitol Esters | |
| Plantasens ® Sweet Almond Oil (Clariant) | 3.00% |
| *Prunus Amygdalus Dulcis* (Sweet Almond) Oil | |
| Plantasens ® Avocado Oil (Clariant) | 2.00% |
| *Persea Gratissima* (Avocao) Oil | |
| Isopropyl Palmitate | 5.00% |
| SilCare ® Silicone SEA (Clariant) | 0.80% |
| Trideceth-9 PG-Amodimethicone and Trideceth-12 | |
| Panthenol | 0.50% |
| Fragrance | 0.30% |
| Tocopheryl Acetate | 0.30% |
| Nipaguard ® SCE (Clariant) | 1.20% |
| Sorbitan Caprylate, Propanediol, Benzoic Acid | |

Example Composition 36: Effect Shower Gel pH=5.0, 510 mPa·s (Brookfield RVDV-1, 20° C., 20 rpm, S04)

| | |
|---|---|
| Genapol ® LRO liquid (Clariant) | 30.00% |
| Sodium Laureth Sulfate | |
| Genagen ® CAB 818 (Clariant) | 6.00% |
| Cocamidopropyl Betaine | |
| Hostapon ® KCG (Clariant) | 5.00% |
| Sodium Cocoyl Glutamate | |
| Water | Ad 100% |
| Polymer-A1/2 | 1.40% |
| (according to polymerization process A1) | |
| Nipaguard ® DMDMH (Clariant) | 0.50% |
| DMDM Hydantoin | |
| Cirebelle 104 Blue | 1.00% |
| Sythetic Wax | |

Example Composition 37: O/W Foundation pH=6.0, 18650 mPa·s (Brookfield RVDV-1, 20° C., 20 rpm, S06)

| | |
|---|---|
| Water | Ad 100% |
| Polymer-A1/2 | 1.00% |
| (according to polymerization process A1) | |
| Magnesium Aluminium Silicate | 1.00% |
| Plantasens ® Natural Emulsifier HP10 (Clariant) | 4.50% |
| Sucrose Polystearate, Cetearyl Alcohol, *Olea Europaea* (Olive) Oil Unsaponifiables | |
| SilCare ® Silicone 31M50 (Clariant) | 2.00% |
| Caprylyl Trimethicone | |
| XIAMETER ® PMX-200 Silicone Fluid 100 CS | 2.00% |
| Dimethicone | |
| Caprylic/Capric Triglyceride | 5.00% |
| Plantasens ® Olive Wax S51 (Clariant) | 1.50% |
| Hydrogenated Vegetable Oil | |
| Chroma-Lite ® Black | 0.10% |
| Mica (and) Bismuth Oxychloride (and) Iron Oxides | |
| Chroma-Lite ® Red | 0.40% |
| Mica (and) Bismuth Oxychloride (and) Iron Oxides | |
| Chroma-Lite ® Yellow | 1.20% |
| Mica (and) Bismuth Oxychloride (and) Iron Oxides | |

Example Composition 38: Anti-Ageing Cream Gel pH=5.1, 1580 mPa·s (Brookfield RVDV-1, 20° C., 20 rpm, S04)

| | |
|---|---|
| Titanium Dioxide | 7.00% |
| Dicaprylyl Carbonate | 4.00% |
| Butylene Glycol | 3.00% |
| Plantasens ® Natural Vitamin E (Clariant) Tocopherol | 1.00% |
| Orgasol ® 4000 EXD NAT COS Caresse Nylon-6/12 | 1.00% |
| Fragrance | 0.20% |
| Nipaguard ® POB (Clariant) Phenoxyethanol (and) Piroctone Olamine (and) Benzoic Acid | 0.80% |

Example Composition 38: Anti-Ageing Cream Gel pH=5.1, 1580 mPa·s (Brookfield RVDV-1, 20° C., 20 rpm, S04)

| | |
|---|---|
| Caprylic/Capric Triglyceride | 5.00% |
| Dicaprylyl Ether | 5.00% |
| Cetearyl Alcohol | 2.00% |
| Nipaguard ® POB (Clariant) Phenoxyethanol (and) Piroctone Olamine (and) Benzoic Acid | 0.80% |
| Ubiquinone | 0.10% |
| Aristoflex ® HMB (Clariant) Ammonium Acryoyldimethyltaurate/ Beheneth-25 Methacrylate Crosspolymer | 0.40% |
| Polymer-A1/2 (according to polymerization process A1) | 0.40% |
| Sodium Hyaluronate | 0.30% |
| Water | Ad 100% |
| Tocopheryl Acetate | 0.30% |
| Fragrance | 0.30% |

Example Composition 39: Caring Night Cream pH=5.8, 22450 mPa*s (Brookfield RVDV-1, 20° C., 20 rpm, S06)

| | |
|---|---|
| Water | Ad 100% |
| Glycerin | 2.00% |
| Polymer-A1/2 (according to polymerization process A1) | 1.00% |
| Hostaphat ® KW 340 D (Clariant) Triceteareth-4 Phosphate | 2.00% |
| Plantasens ® Oat Serum (Clariant) Avena Sativa (Oat) Kernel Oil (and) Phytosterols (and) Olea Europaea (Olive) Oil Unsaponifiables (and) Beeswax | 3.00% |
| Plantasens ® Shea Butter (Clariant) Butyrospermum Parkii (Shea) Butter | 7.00% |
| Isopropyl Palmitate | 5.00% |
| Macadamia Integrifolia Seed Oil | 4.00% |
| Cera Alba (Beeswax) | 3.00% |
| Nipaguard ® SCP (Clariant) Phenoxyethanol (and) Sorbitan Caprylate | 1.00% |
| Fragrance | 0.30% |
| Sodium Hydroxide | 0.10% |

Example Composition 40: Hand Sanitizer pH=5.4, 30600 mPa*s (Brookfield RVDV-1, 20° C., 20 rpm, S06)

| | |
|---|---|
| Water | ad 100% |
| Glycerin | 2.00% |
| Polymer-A1/2 (according to polymerization process A1) | 0.50% |
| Ethanol | 70.0% |
| XIAMETER ® OFX-5324 Fluid PEG-12 Dimethicone | 6.00% |
| Aloe Barbadensis Leaf Extract | 0.30% |

Method of Use

Example Methods of Use:

Example Composition 19 is applied to wet hair in an amount of about 2 ml per 2 gram of hair (dry weight). Tap water is employed to create a lather and spread the composition throughout the hair and scalp. The composition is immediately rinsed from the hair. The hair may further be conditioned.

Example Compositions 1, 2, 12, 13, 14, 15, 16, 17, 22, 24, and 37 to 39 are applied to human skin and left on the skin to sink in, and the skin allowed to dry.

EXPERIMENTAL

Experimental Example 1: Polymers According to Polymerization Process B1: Viscosity Dependence on Polymer Concentration The following example comprises a polymer according to the present invention as Polymer B1/16 compared with Polymer B1/16 #. Polymer B1/16 # being a comparative example in that is the same as Polymer B1/16 but with common building blocks derived from petrochemicals.

See FIG. 1: The viscosity measurements in dependence of polymer concentration with Polymer B1/16 (solid line) and Polymer B1/16 # (broken line) showed very similar results, therefore Polymer B1/16 and Polymer B1/16 # are interchangeable with one another.

Experimental Example 2: Polymers According to Polymerization Process B1: Viscosity Dependence on pH The following example comprises a polymer according to the present invention as Polymer B1/16 compared with Polymer B1/16 #. Polymer B1/16 # being a comparative example in that is the same as Polymer B1/16 but with common building blocks derived from petrochemicals.

Figure 2:
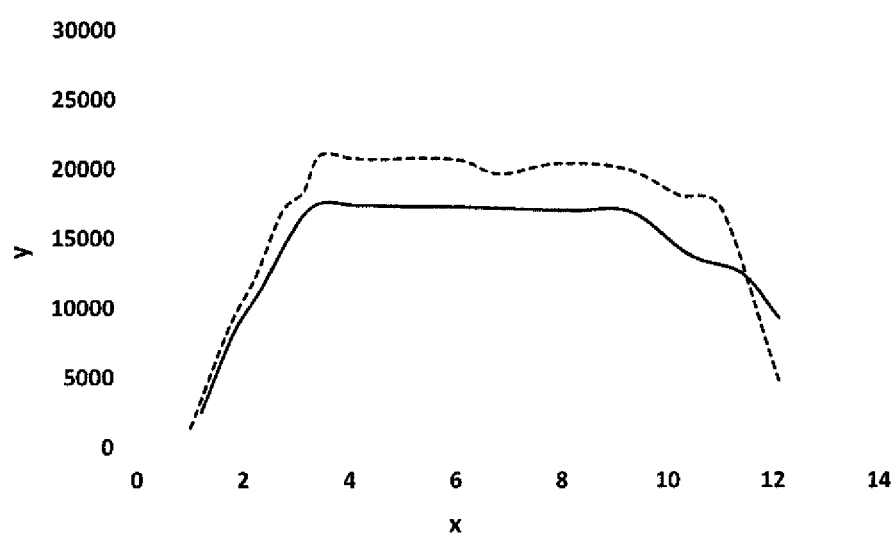
FIG. 2: Viscosity dependence on pH; 1.0 wt. % polymer measured in deionized water (Brookfield RVDV-1, 20° C., 20 rpm). The x-axis shows the pH. The y-axis shows the viscosity in mPa·s. Polymer B1/16 (according to the invention; solid line) and a comparative polymer B1/16 # are compared (broken line).

See FIG. 2: The viscosity measurements and their dependence on pH with Polymer B1/16 and Polymer B1/16 # showed very similar results, therefore Polymer B1/16 and Polymer B1/16 # are interchangeable with one another.

Experimental Example 3: Polymers According to Polymerization Process A3

The following example comprises a polymer according to the present invention as Polymer-A3/8 compared with Polymer-A3/8 #. Polymer A3/8 # being a comparative example in that is the same as Polymer-A3/8 but with common building blocks derived from petrochemicals.

Typical measurements of Polymer-A3/8 and Polymer-A3/8 # showed very similar results (Exp. Table 1), therefore Polymer-A3/8 and Polymer-A3/8 # are interchangeable with one another.

Exp. Table 1: Polymers according to polymerization process A3.
Viscosity measurement: Brookfield RVDV-1, 20° C., 20 rpm.

| Polymer | Viscosity/mPa · s | pH |
|---------|-------------------|-----|
| A3/8    | 18000             | 5.0 |
| A3/8#   | 19300             | 5.3 |

Experimental Example 4: Polymers According to Polymerization Process A1: Viscosity Dependence on pH The following example comprises a polymer according to the present invention as Polymer A1/2 compared with Polymer A1/2 #. Polymer A1/2 # being a comparative example in that is the same as Polymer A1/2 but with common building blocks derived from petrochemicals.

Figure 3:
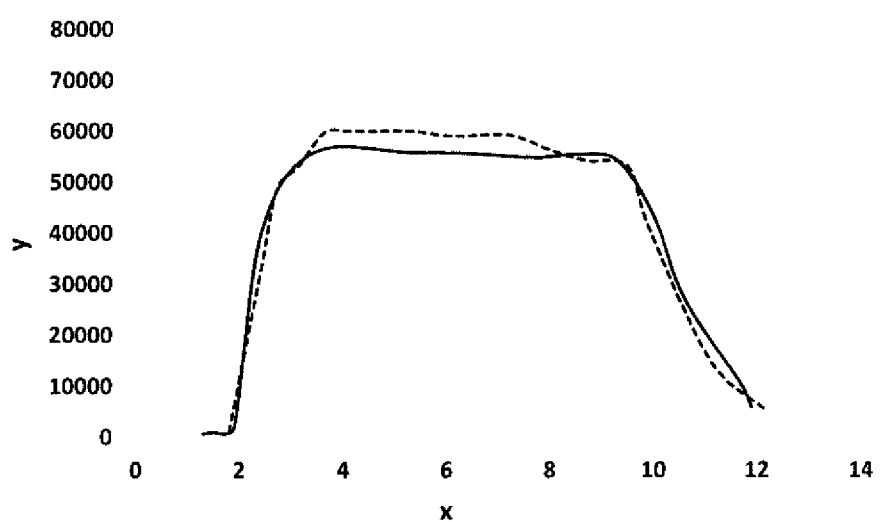
FIG. 3: Viscosity dependence on pH; 1.0 wt. % polymer measured in deionized water (Brookfield RVDV-1, 20° C., 20 rpm). The x-axis shows the pH. The y-axis shows the viscosity in mPa·s. Polymer A1/2 (according to the invention; solid line) and a comparative polymer A1/2 # are compared (broken line).

See FIG. 3: The viscosity measurements and their dependence on pH with Polymer A1/2 and Polymer A1/2 # showed very similar results, therefore Polymer A1/2 and Polymer A1/2 # are interchangeable with one another.

The invention claimed is:

1. A method for thickening or modifying a rheology in a cosmetic, dermatological or pharmaceutical composition comprising the step of adding at least one polymer to the cosmetic, dermatological or pharmaceutical composition, wherein the polymer is crosslinked, and comprises at least 9.49 mol % of repeating units (a) according to Formula (1) wherein at least 10 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

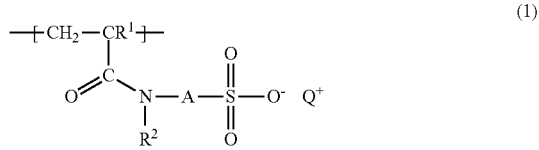

(1)

wherein:
R$^1$ and R$^2$ are H;
A is a linear or branched C$_4$-alkyl group; and Q$^+$ is NH$_4^+$, and
wherein the polymer of Formula (1) is crosslinked with trimethylolpropane triacrylate (TMPTA).

2. The method according to claim 1, wherein the cosmetic, dermatological or pharmaceutical composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

3. The method according to claim 1, wherein the cosmetic, dermatological or pharmaceutical composition further comprises:
(II) at least one cosmetically acceptable component.

4. The method according to claim 3, wherein the at least one cosmetically acceptable component is an auxiliary or mixture of auxiliaries, selected from the group consisting of oily substances, waxes, emulsifiers, coemulsifiers, solubilizers, cationic polymers, film formers, superfatting agents, refatting agents, foam stabilizers, stabilizers, active biogenic substances, preservatives, preservation boosting ingredients, anti-fungal substance, anti-dandruff agents, dyes or pigments, particulate substances, opacifiers, abrasives, absorbents, anticaking agents, bulking agents, pearlizing agents, direct dyes, perfumes or fragrances, carriers, solvents or diluents, propellants, functional acids, active ingredients, skin-brightening agents, self-tanning agents, exfoliants, enzymes, anti-acne agents, deodorants and anti-perspirants, viscosity modifiers, thickening and gelling agents, pH adjusting agents, buffering agents, anti-oxidants, chelants, astringents, sunscreens, sun protection agents, UV filters, skin conditioning agents, emollients, humectants, occlusive agents, pediculocides, anti-foaming agents, flavouring agents, electrolytes, oxidizing agents and reducing agents.

5. The method according to claim 1, wherein the polymer has a weight average molecular weight of at least 700 g/mol.

6. The method according to claim 3, wherein the cosmetic, dermatological or pharmaceutical composition is an emulsion or a gel.

7. The method according to claim 3, wherein the cosmetic, dermatological or pharmaceutical composition has a viscosity from 100 000 to 200 000 mPa·s, (measured at 25° C., Brookfield RVT, T-C spindle at 20 revolutions per minute).

8. The method according to claim 3, wherein the cosmetic, dermatological or pharmaceutical composition is a body or face care composition, and wherein the body or face care composition comprises from 0.1 wt % to 15 wt % of at least one emulsifier, coemulsifier and/or solubilizer, by total weight of the composition.

* * * * *